United States Patent
Boka et al.

(10) Patent No.: US 9,981,013 B2
(45) Date of Patent: May 29, 2018

(54) USE OF AVE0010 FOR THE TREATMENT OF DIABETES MELLITUS TYPE 2

(71) Applicant: SANOFI-AVENTIS DEUTSCHLAND GMBH, Frankfurt (DE)

(72) Inventors: Gabor Boka, Paris (FR); Patrick Miossec, Paris (FR); Louise Silvestre, Paris (FR)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days. days.

(21) Appl. No.: 15/237,285

(22) Filed: Aug. 15, 2016

(65) Prior Publication Data

US 2017/0119852 A1   May 4, 2017

Related U.S. Application Data

(63) Continuation of application No. 13/819,114, filed as application No. PCT/EP2010/062638 on Aug. 30, 2010, now abandoned.

(51) Int. Cl.
*A61K 38/22* (2006.01)
*C07K 14/575* (2006.01)
*A61P 3/10* (2006.01)
*A61P 3/08* (2006.01)
*A61P 3/04* (2006.01)
*A61K 38/26* (2006.01)
*C07K 14/46* (2006.01)

(52) U.S. Cl.
CPC ............ *A61K 38/26* (2013.01); *A61K 38/22* (2013.01); *C07K 14/463* (2013.01)

(58) Field of Classification Search
None
See application file for complete search history.

(56) References Cited

U.S. PATENT DOCUMENTS

| | | |
|---|---|---|
| 3,758,683 A | 9/1973 | Jackson |
| 3,868,358 A | 2/1975 | Jackson |
| 4,153,689 A | 5/1979 | Hirai et al. |
| 4,258,134 A | 3/1981 | Yoshida et al. |
| 4,367,737 A | 1/1983 | Kozam et al. |
| 4,608,364 A | 8/1986 | Grau |
| 4,614,730 A | 9/1986 | Hansen et al. |
| 4,644,057 A | 2/1987 | Bicker et al. |
| 4,689,042 A | 8/1987 | Sarnoff et al. |
| 4,701,440 A | 10/1987 | Grau |
| 4,731,405 A | 3/1988 | Kirsch et al. |
| 4,783,441 A | 11/1988 | Thurow |
| 4,839,341 A | 6/1989 | Massey et al. |
| 4,863,902 A | 9/1989 | Amagase et al. |
| 4,885,164 A | 12/1989 | Thurow |
| 4,923,162 A | 5/1990 | Fleming et al. |
| 4,959,351 A | 9/1990 | Grau |
| 4,960,702 A | 10/1990 | Rice et al. |
| 4,994,439 A | 2/1991 | Longenecker et al. |
| 5,008,241 A | 4/1991 | Markussen et al. |
| 5,034,415 A | 7/1991 | Rubin |
| 5,070,186 A | 12/1991 | Joergensen |
| 5,101,013 A | 3/1992 | Doerschug et al. |
| 5,177,058 A | 1/1993 | Doerschug |
| 5,187,177 A | 2/1993 | Garzaran |
| 5,227,293 A | 7/1993 | Stengelin et al. |
| 5,253,785 A | 10/1993 | Haber et al. |
| 5,272,135 A | 12/1993 | Takruri |
| 5,358,708 A | 10/1994 | Patel |
| 5,358,857 A | 10/1994 | Stengelin et al. |
| 5,370,629 A | 12/1994 | Michel et al. |
| 5,397,771 A | 3/1995 | Bechgaard et al. |
| 5,407,609 A | 4/1995 | Tice et al. |
| 5,424,286 A | 6/1995 | Eng |
| 5,428,006 A | 6/1995 | Bechgaard et al. |
| 5,473,049 A | 12/1995 | Obermeier et al. |
| 5,474,978 A | 12/1995 | Bakaysa et al. |
| 5,478,323 A | 12/1995 | Westwood et al. |
| 5,496,924 A | 3/1996 | Habermann et al. |
| 5,506,203 A | 4/1996 | Baeckstroem et al. |
| 5,509,905 A | 4/1996 | Michel |
| 5,514,646 A | 5/1996 | Chance et al. |
| 5,524,286 A | 6/1996 | Chiesa et al. |
| 5,534,488 A | 7/1996 | Hoffmann |
| 5,545,618 A | 8/1996 | Buckley et al. |
| 5,547,929 A | 8/1996 | Anderson, Jr. et al. |
| 5,559,094 A | 9/1996 | Brems et al. |
| 5,595,756 A | 1/1997 | Bally et al. |
| 5,597,796 A | 1/1997 | Brange |
| 5,614,219 A | 3/1997 | Wunderlich et al. |
| 5,614,492 A | 3/1997 | Habener |
| 5,631,224 A | 5/1997 | Efendic et al. |
| 5,654,008 A | 8/1997 | Herbert et al. |
| 5,656,722 A | 8/1997 | Doerschug |
| 5,663,291 A | 9/1997 | Obermeier et al. |
| 5,670,360 A | 9/1997 | Thorens |
| 5,693,608 A | 12/1997 | Bechgaard et al. |
| 5,700,662 A | 12/1997 | Chance et al. |
| 5,707,641 A | 1/1998 | Gertner et al. |
| 5,783,556 A | 7/1998 | Clark et al. |
| 5,824,638 A | 10/1998 | Burnside et al. |
| 5,846,747 A | 12/1998 | Thorens et al. |

(Continued)

FOREIGN PATENT DOCUMENTS

| | | |
|---|---|---|
| AU | 593274 B2 | 2/1990 |
| AU | 612324 B2 | 7/1991 |

(Continued)

OTHER PUBLICATIONS

Akbar, "Sub-Optimal postprandial blood glucose level in diabetics attending the outpatient clinic of a University Hospital" Saudi Med Journal, 24(10):1109-1112 (Oct. 2003).

(Continued)

*Primary Examiner* — Julie Ha
*Assistant Examiner* — Kristina M Hellman
(74) *Attorney, Agent, or Firm* — McDonnell Boehnen Hulbert & Berghoff LLP

(57) ABSTRACT

The present invention refers to the use of Lixisenatide or/and a pharmaceutically acceptable salt thereof, for the manufacture of a medicament for the treatment of diabetes mellitus type 2, for inducing weight loss in diabetes type 2 patients or/and for preventing weight gain in diabetes type 2 patients.

8 Claims, 6 Drawing Sheets

(56) References Cited

U.S. PATENT DOCUMENTS

Figure 1:
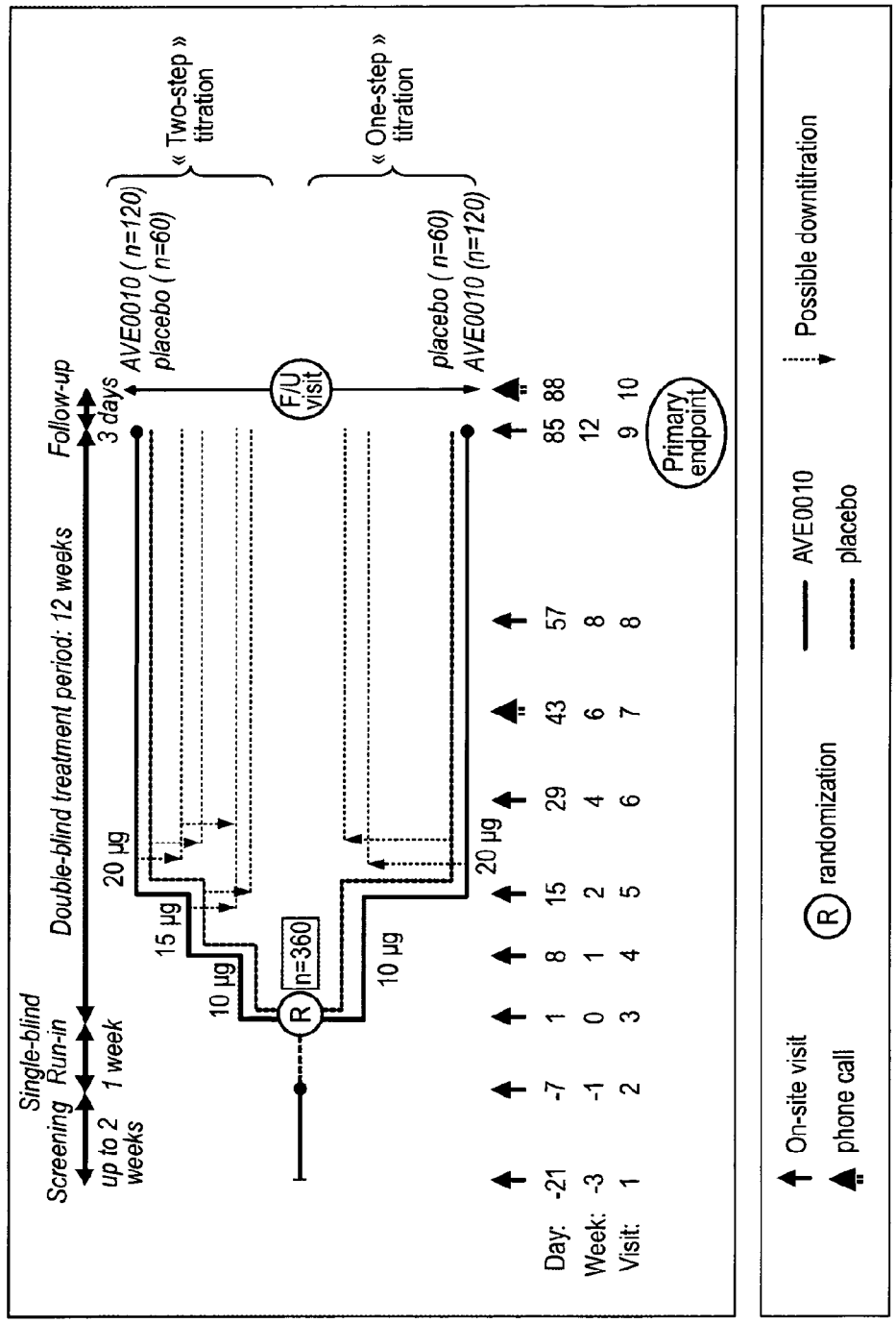

| | | |
|---|---|---|
| 5,846,937 A | 12/1998 | Drucker |
| 5,879,584 A | 3/1999 | Bianchetti et al. |
| 5,948,751 A | 9/1999 | Kimer et al. |
| 5,952,297 A | 9/1999 | De Felippis et al. |
| 5,985,309 A | 11/1999 | Edwards et al. |
| 5,986,048 A | 11/1999 | Rubroder et al. |
| 6,006,753 A | 12/1999 | Efendic |
| 6,034,054 A | 3/2000 | Defelippis et al. |
| 6,043,214 A | 3/2000 | Jensen et al. |
| 6,051,551 A | 4/2000 | Hughes et al. |
| 6,051,689 A | 4/2000 | Thorens |
| 6,100,376 A | 8/2000 | Doerschug |
| 6,110,703 A | 8/2000 | Egel-Mitani et al. |
| 6,174,856 B1 | 1/2001 | Langballe et al. |
| 6,191,102 B1 | 2/2001 | Dimarchi et al. |
| 6,197,926 B1 | 3/2001 | Gaur et al. |
| 6,211,144 B1 | 4/2001 | Havelund |
| 6,227,819 B1 | 5/2001 | Gettel et al. |
| 6,248,363 B1 | 6/2001 | Patel et al. |
| 6,267,981 B1 | 7/2001 | Okamoto et al. |
| 6,268,335 B1 | 7/2001 | Brader |
| 6,268,343 B1 | 7/2001 | Knudsen et al. |
| 6,271,241 B1 | 8/2001 | Desimone et al. |
| 6,284,725 B1 | 9/2001 | Coolidge et al. |
| 6,309,663 B1 | 10/2001 | Patel et al. |
| 6,310,038 B1 | 10/2001 | Havelund |
| 6,329,336 B1 | 12/2001 | Bridon et al. |
| 6,335,316 B1 | 1/2002 | Hughes et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,395,767 B2 | 5/2002 | Robl et al. |
| 6,410,508 B1 | 6/2002 | Isales et al. |
| 6,417,164 B1 | 7/2002 | Kolterman |
| 6,444,641 B1 | 9/2002 | Flora |
| 6,468,959 B1 | 10/2002 | Wunderlich et al. |
| 6,489,292 B1 | 12/2002 | Havelund et al. |
| 6,528,486 B1 | 3/2003 | Larsen et al. |
| 6,734,162 B2 | 5/2004 | Van Antwerp et al. |
| 6,767,887 B1 | 7/2004 | Hoffmann et al. |
| 6,818,738 B2 | 11/2004 | Havelund |
| 6,852,694 B2 | 2/2005 | Van Antwerp et al. |
| 6,875,589 B1 | 4/2005 | Doerschug et al. |
| 6,908,610 B1 | 6/2005 | Sato |
| 6,908,897 B2 | 6/2005 | Brandenburg et al. |
| 6,960,561 B2 | 11/2005 | Boderke |
| 6,969,702 B2 | 11/2005 | Bertilsson et al. |
| 7,022,674 B2 | 4/2006 | Defelippis et al. |
| 7,115,563 B2 | 10/2006 | Younis et al. |
| 7,119,086 B2 | 10/2006 | Di Malta et al. |
| 7,192,919 B2 | 3/2007 | Tzannis et al. |
| 7,205,276 B2 | 4/2007 | Boderke |
| 7,205,277 B2 | 4/2007 | Boderke |
| 7,238,663 B2 | 7/2007 | Defelippis et al. |
| 7,405,196 B2 | 7/2008 | Rosskamp et al. |
| 7,476,652 B2 | 1/2009 | Brunner-Schwarz et al. |
| 7,544,656 B2 | 6/2009 | Sabetsky |
| 7,544,657 B2 | 6/2009 | Ebbehoj et al. |
| 7,576,050 B2 | 8/2009 | Greig et al. |
| 7,713,930 B2 | 5/2010 | Brunner-Schwarz et al. |
| 7,803,763 B2 | 9/2010 | Thurow et al. |
| 7,807,242 B2 | 10/2010 | Soerensen et al. |
| 7,918,833 B2 | 4/2011 | Veasey et al. |
| 7,939,293 B2 | 5/2011 | Habermann et al. |
| 7,977,310 B2 | 7/2011 | Rosskamp et al. |
| 8,048,854 B2 | 11/2011 | Habermann et al. |
| 8,084,420 B2 | 12/2011 | Steiner et al. |
| 8,092,421 B2 | 1/2012 | Seiferlein et al. |
| 8,092,422 B2 | 1/2012 | Seiferlein et al. |
| 8,178,495 B2 | 5/2012 | Chilkoti |
| 8,574,214 B2 | 11/2013 | Kuehn et al. |
| 8,633,156 B2 | 1/2014 | Habermann et al. |
| 8,735,349 B2 | 5/2014 | Silvestre et al. |
| 2001/0012829 A1 | 8/2001 | Anderson et al. |
| 2001/0033868 A1 | 10/2001 | Rossling et al. |
| 2001/0039260 A1 | 11/2001 | Havelund |
| 2001/0047084 A1 | 11/2001 | Knudsen et al. |
| 2002/0107265 A1 | 8/2002 | Chen et al. |
| 2002/0132760 A1 | 9/2002 | Van Antwerp et al. |
| 2002/0177151 A1 | 11/2002 | Gimeno |
| 2002/0198140 A1 | 12/2002 | Havelund |
| 2003/0004096 A1 | 1/2003 | Boderke |
| 2003/0026872 A1 | 2/2003 | Dake et al. |
| 2003/0104983 A1 | 6/2003 | Defelippis et al. |
| 2003/0170691 A1 | 9/2003 | Gimeno |
| 2004/0037893 A1 | 2/2004 | Hansen et al. |
| 2004/0048783 A1 | 3/2004 | Brunner-Schwarz et al. |
| 2004/0092590 A1 | 5/2004 | Arteburn et al. |
| 2004/0097410 A1 | 5/2004 | Zheng et al. |
| 2004/0106547 A1 | 6/2004 | Larsen et al. |
| 2004/0186046 A1 | 9/2004 | Burgess et al. |
| 2004/0229774 A1 | 11/2004 | Rosskamp et al. |
| 2004/0235710 A1 | 11/2004 | Defelippis et al. |
| 2004/0242853 A1 | 12/2004 | Greig et al. |
| 2005/0014679 A1 | 1/2005 | Beals et al. |
| 2005/0079996 A1 | 4/2005 | Horiguchi et al. |
| 2005/0106147 A1 | 5/2005 | Jordan et al. |
| 2005/0171009 A1 | 8/2005 | Brunner-Schwarz et al. |
| 2005/0209142 A1 | 9/2005 | Bertilsson et al. |
| 2006/0004049 A1 | 1/2006 | Yao et al. |
| 2006/0014678 A1 | 1/2006 | Cowley et al. |
| 2006/0019347 A1 | 1/2006 | Cho et al. |
| 2006/0057137 A1 | 3/2006 | Steiness |
| 2006/0073213 A1 | 4/2006 | Hotamisligil et al. |
| 2006/0093576 A1 | 5/2006 | Chen et al. |
| 2006/0194719 A1 | 8/2006 | Ebbehoj et al. |
| 2006/0239933 A1 | 10/2006 | Nilsson et al. |
| 2006/0287221 A1 | 12/2006 | Knudsen et al. |
| 2007/0027063 A1 | 2/2007 | Boss et al. |
| 2007/0111940 A1 | 5/2007 | Larsen et al. |
| 2007/0128193 A1 | 6/2007 | O'Neil et al. |
| 2007/0135338 A1 | 6/2007 | O'Neil et al. |
| 2007/0155653 A1 | 7/2007 | Boderke |
| 2007/0191271 A1 | 8/2007 | Mayhew et al. |
| 2007/0237827 A1 | 10/2007 | Sung et al. |
| 2008/0064856 A1 | 3/2008 | Warne et al. |
| 2008/0146490 A1 | 6/2008 | Joabsson et al. |
| 2008/0234200 A1 | 9/2008 | Quay et al. |
| 2008/0248999 A1 | 10/2008 | Steiner |
| 2008/0260840 A1 | 10/2008 | Alessi et al. |
| 2008/0267907 A1 | 10/2008 | Poulsen |
| 2009/0082255 A1 | 3/2009 | Brunner-Schwarz et al. |
| 2009/0088369 A1 | 4/2009 | Steiness |
| 2009/0099064 A1 | 4/2009 | Lougheed |
| 2009/0142338 A1 | 6/2009 | Levetan |
| 2009/0175840 A1 | 7/2009 | Kashyap et al. |
| 2009/0176692 A1 | 7/2009 | Habermann et al. |
| 2009/0180953 A1 | 7/2009 | Gotthardt et al. |
| 2009/0186819 A1 | 7/2009 | Carrier et al. |
| 2009/0208565 A1 | 8/2009 | Ebbehoj et al. |
| 2009/0214468 A1 | 8/2009 | Lin et al. |
| 2009/0214657 A1 | 8/2009 | Qazi et al. |
| 2009/0304665 A1 | 12/2009 | Frost et al. |
| 2009/0312236 A1 | 12/2009 | Beals et al. |
| 2009/0324701 A1 | 12/2009 | Williams |
| 2010/0029558 A1 | 2/2010 | Bristow |
| 2010/0055049 A1 | 3/2010 | Kuo et al. |
| 2010/0057194 A1 | 3/2010 | Ryan |
| 2010/0069292 A1 | 3/2010 | Pohl et al. |
| 2010/0069293 A1 | 3/2010 | Bolotin et al. |
| 2010/0227816 A1 | 9/2010 | Flatt et al. |
| 2010/0279931 A1 | 11/2010 | Garibay et al. |
| 2010/0311112 A1 | 12/2010 | Rissom et al. |
| 2011/0020294 A1 | 1/2011 | Hammerman |
| 2011/0021423 A1 | 1/2011 | Olsen et al. |
| 2011/0077197 A1 | 3/2011 | Habermann et al. |
| 2011/0118178 A1 | 5/2011 | Silvestre et al. |
| 2011/0118180 A1 | 5/2011 | Silvestre et al. |
| 2011/0144008 A1 | 6/2011 | Larsen et al. |
| 2011/0152185 A1 | 6/2011 | Plum et al. |
| 2011/0173722 A1 | 7/2011 | Habermann et al. |
| 2011/0230402 A1 | 9/2011 | Johansen et al. |
| 2011/0236925 A1 | 9/2011 | Hazra et al. |

(56) References Cited

U.S. PATENT DOCUMENTS

| | | |
|---|---|---|
| 2011/0245165 A1 | 10/2011 | Larsen et al. |
| 2011/0281790 A1 | 11/2011 | Pohl et al. |
| 2011/0301081 A1 | 12/2011 | Becker et al. |
| 2012/0021978 A1 | 1/2012 | Werner et al. |
| 2012/0121611 A1 | 5/2012 | Lodie et al. |
| 2012/0122774 A1 | 5/2012 | Becker et al. |
| 2012/0183616 A1 | 7/2012 | Sprogoe et al. |
| 2012/0232002 A1 | 9/2012 | Schoettle et al. |
| 2012/0241356 A1 | 9/2012 | Pfenninger et al. |
| 2012/0252724 A1 | 10/2012 | Schoettle et al. |
| 2012/0277147 A1 | 11/2012 | Boka et al. |
| 2012/0283179 A1 | 11/2012 | Brunner-Schwarz et al. |
| 2012/0295846 A1 | 11/2012 | Hagendorg et al. |
| 2012/0316108 A1 | 12/2012 | Chen et al. |
| 2013/0005649 A1 | 1/2013 | Niemoeller et al. |
| 2013/0012433 A1 | 1/2013 | Rosskamp et al. |
| 2013/0023467 A1 | 1/2013 | Silvestre et al. |
| 2013/0040878 A1 | 2/2013 | Silvestre |
| 2013/0065828 A1 | 3/2013 | Ruus et al. |
| 2013/0079279 A1 | 3/2013 | Becker et al. |
| 2013/0085102 A1 | 4/2013 | Silvestre |
| 2013/0096059 A1 | 4/2013 | Stechl et al. |
| 2013/0096060 A1 | 4/2013 | Stechl et al. |
| 2013/0116179 A1 | 5/2013 | Hess et al. |
| 2013/0203666 A1 | 8/2013 | Niemoeller et al. |
| 2013/0284912 A1 | 10/2013 | Vogel et al. |
| 2013/0296236 A1 | 11/2013 | Silvestre |
| 2014/0148384 A1 | 5/2014 | Boka et al. |
| 2014/0206611 A1 | 7/2014 | Becker et al. |
| 2014/0221285 A1 | 8/2014 | Bley et al. |
| 2014/0248365 A1 | 9/2014 | Rademacher et al. |
| 2014/0371141 A1 | 12/2014 | Souhami et al. |

FOREIGN PATENT DOCUMENTS

| | | |
|---|---|---|
| CA | 1173388 A | 8/1984 |
| CA | 1258427 A | 8/1989 |
| CA | 1336329 C | 7/1995 |
| CA | 1341203 C | 3/2001 |
| CA | 2 662 084 | 3/2008 |
| CN | 1276731 A | 12/2000 |
| CN | CN 1413582 | 4/2003 |
| CN | 101366692 A | 2/2009 |
| CN | 101444618 A | 6/2009 |
| CN | 101454019 A | 6/2009 |
| CN | 101670096 A | 3/2010 |
| DE | 2219635 A1 | 11/1972 |
| DE | 3240177 A1 | 5/1983 |
| DE | 19637230 A1 | 3/1998 |
| DE | 102008003566 A1 | 7/2009 |
| DE | 102008003568 A1 | 7/2009 |
| DE | 10 2008 053048 | 4/2010 |
| EA | 006019 B1 | 8/2005 |
| EP | 0018609 B1 | 9/1983 |
| EP | 0046979 B1 | 9/1983 |
| EP | 0132769 A1 | 2/1985 |
| EP | 0140084 A1 | 5/1985 |
| EP | 0166529 A1 | 1/1986 |
| EP | 0180920 A2 | 5/1986 |
| EP | 0200383 A2 | 11/1986 |
| EP | 0211299 A2 | 2/1987 |
| EP | 0214826 A2 | 3/1987 |
| EP | 0224885 A1 | 6/1987 |
| EP | 0227938 A2 | 7/1987 |
| EP | 0229956 A1 | 7/1987 |
| EP | 0229998 A2 | 7/1987 |
| EP | 0254516 A2 | 1/1988 |
| EP | 0305760 A2 | 3/1989 |
| EP | 0368187 A2 | 5/1990 |
| EP | 0375437 A2 | 6/1990 |
| EP | 0383472 A2 | 8/1990 |
| EP | 0194864 B1 | 6/1992 |
| EP | 0419504 B1 | 1/1994 |
| EP | 0600372 A1 | 6/1994 |
| EP | 0668282 A1 | 8/1995 |
| EP | 0668292 A2 | 8/1995 |
| EP | 0678522 A1 | 10/1995 |
| EP | 0837072 A2 | 4/1998 |
| EP | 0845265 A1 | 6/1998 |
| EP | 0885961 A1 | 12/1998 |
| EP | 1076066 A1 | 2/2001 |
| EP | 1172114 A2 | 1/2002 |
| EP | 1222207 A1 | 7/2002 |
| EP | 1 196 444 | 4/2003 |
| EP | 1364029 A1 | 11/2003 |
| EP | 1523993 A1 | 4/2005 |
| EP | 1906991 A2 | 4/2008 |
| EP | 2 112 161 | 10/2009 |
| EP | 2187950 A1 | 5/2010 |
| EP | 2 324 853 | 5/2011 |
| EP | 2 329 848 | 6/2011 |
| EP | 2 389 945 | 11/2011 |
| EP | 0921812 B2 | 12/2011 |
| EP | 2387989 B1 | 7/2014 |
| FR | 2456522 A1 | 12/1980 |
| GB | 835638 A | 5/1960 |
| GB | 840870 A | 7/1960 |
| GB | 1527605 A | 10/1978 |
| GB | 1554157 A | 10/1979 |
| JP | S61212598 A | 9/1986 |
| JP | S6399096 A | 4/1988 |
| JP | H02218696 A | 8/1990 |
| JP | H02264798 A | 10/1990 |
| JP | H03504240 A | 9/1991 |
| JP | H06506444 A | 7/1994 |
| JP | 2001521004 A | 11/2001 |
| JP | 2002516880 A | 6/2002 |
| JP | 2003505347 A | 2/2003 |
| JP | 2005508895 A | 4/2005 |
| JP | 2005532365 A | 10/2005 |
| JP | 2006515267 A | 5/2006 |
| JP | 2006137678 A | 6/2006 |
| JP | 2007204498 A | 8/2007 |
| JP | 2009091363 A | 4/2009 |
| JP | 2009-519961 | 5/2009 |
| JP | 2012505852 A | 3/2012 |
| JP | 2012255040 A | 12/2012 |
| RU | 2008116057 A | 10/2009 |
| TW | 157005 B | 5/1991 |
| TW | 562806 B | 11/2003 |
| WO | WO-8300288 A1 | 2/1983 |
| WO | WO-8806599 A1 | 9/1988 |
| WO | WO-8910937 A1 | 11/1989 |
| WO | WO-9007522 A1 | 7/1990 |
| WO | WO-9011299 A1 | 10/1990 |
| WO | WO-9103550 A1 | 3/1991 |
| WO | WO-9116929 A1 | 11/1991 |
| WO | WO-9200321 A1 | 1/1992 |
| WO | WO-9212999 A1 | 8/1992 |
| WO | WO-9318786 A1 | 9/1993 |
| WO | WO-9414461 A1 | 7/1994 |
| WO | WO-9500550 A1 | 1/1995 |
| WO | WO-9524183 A1 | 9/1995 |
| WO | WO-9604307 A1 | 2/1996 |
| WO | WO-9607399 A1 | 3/1996 |
| WO | WO-9611705 A1 | 4/1996 |
| WO | WO-9632414 A1 | 10/1996 |
| WO | WO-9634882 A1 | 11/1996 |
| WO | WO-9641606 A2 | 12/1996 |
| WO | WO-9701331 A2 | 1/1997 |
| WO | WO-9748413 A1 | 12/1997 |
| WO | WO-9805351 A1 | 2/1998 |
| WO | WO-9808531 A1 | 3/1998 |
| WO | WO-9808871 A1 | 3/1998 |
| WO | WO-9808873 A1 | 3/1998 |
| WO | WO-9819698 A1 | 5/1998 |
| WO | WO-9830231 A1 | 7/1998 |
| WO | WO-9835033 A1 | 8/1998 |
| WO | WO-9839022 A1 | 9/1998 |
| WO | WO-9842749 A1 | 10/1998 |
| WO | WO-9856406 A1 | 12/1998 |
| WO | WO-9856418 A1 | 12/1998 |
| WO | WO-9907404 A1 | 2/1999 |
| WO | WO-9921573 A1 | 5/1999 |

(56) References Cited

FOREIGN PATENT DOCUMENTS

| | | |
|---|---|---|
| WO | WO-9921578 A1 | 5/1999 |
| WO | WO-9924071 A1 | 5/1999 |
| WO | WO-9925727 A2 | 5/1999 |
| WO | WO-9925728 A1 | 5/1999 |
| WO | WO-9940788 A1 | 8/1999 |
| WO | WO-9943708 A1 | 9/1999 |
| WO | WO-9946283 A1 | 9/1999 |
| WO | WO-9962558 A1 | 12/1999 |
| WO | WO-0023098 A1 | 4/2000 |
| WO | WO-0023099 A1 | 4/2000 |
| WO | WO-0029013 A1 | 5/2000 |
| WO | WO-0041546 A2 | 7/2000 |
| WO | WO-0066629 A1 | 11/2000 |
| WO | WO-0074736 A1 | 12/2000 |
| WO | WO-0100223 A2 | 1/2001 |
| WO | WO-0102039 A1 | 1/2001 |
| WO | WO-0112155 A1 | 2/2001 |
| WO | WO-0121154 A2 | 3/2001 |
| WO | WO 01/24814 | 4/2001 |
| WO | WO-0125278 A1 | 4/2001 |
| WO | WO-0128555 A1 | 4/2001 |
| WO | WO 01/32157 | 5/2001 |
| WO | WO-0137808 A1 | 5/2001 |
| WO | WO-0143762 A2 | 6/2001 |
| WO | WO-0151071 A2 | 7/2001 |
| WO | WO-0152937 A1 | 7/2001 |
| WO | WO-0193837 A2 | 12/2001 |
| WO | WO-0200243 A2 | 1/2002 |
| WO | WO-0224214 A2 | 3/2002 |
| WO | WO-02064115 A1 | 8/2002 |
| WO | WO-02065985 A2 | 8/2002 |
| WO | WO-02066628 A2 | 8/2002 |
| WO | WO-02068660 A1 | 9/2002 |
| WO | WO-02070722 A1 | 9/2002 |
| WO | WO-02076495 A1 | 10/2002 |
| WO | WO-02079250 A1 | 10/2002 |
| WO | WO-03002021 A2 | 1/2003 |
| WO | WO-03020201 A2 | 3/2003 |
| WO | WO-03035028 A1 | 5/2003 |
| WO | WO-03035051 A2 | 5/2003 |
| WO | WO-03044210 A2 | 5/2003 |
| WO | WO-03053339 A2 | 7/2003 |
| WO | WO-03066084 A1 | 8/2003 |
| WO | WO-03094951 A1 | 11/2003 |
| WO | WO-03094956 A1 | 11/2003 |
| WO | WO-03101395 A2 | 12/2003 |
| WO | WO-03105888 A1 | 12/2003 |
| WO | WO 2004/005342 | 1/2004 |
| WO | WO-2004035623 A2 | 4/2004 |
| WO | WO-2004045592 A2 | 6/2004 |
| WO | WO-2004050115 A2 | 6/2004 |
| WO | WO-2004064862 A1 | 8/2004 |
| WO | WO-2004078196 A1 | 9/2004 |
| WO | WO-2004078197 A1 | 9/2004 |
| WO | WO-2004078198 A1 | 9/2004 |
| WO | WO-2004080480 A1 | 9/2004 |
| WO | WO-2004096854 A2 | 11/2004 |
| WO | WO 2004/105781 | 12/2004 |
| WO | WO-2004107979 A1 | 12/2004 |
| WO | WO-2005021022 A2 | 3/2005 |
| WO | WO-2005023291 A2 | 3/2005 |
| WO | WO-2005028516 A2 | 3/2005 |
| WO | WO-2005046716 A1 | 5/2005 |
| WO | WO-2005048950 A2 | 6/2005 |
| WO | WO-2005112949 A1 | 12/2005 |
| WO | WO-2005117948 A1 | 12/2005 |
| WO | WO-2006000567 A2 | 1/2006 |
| WO | WO-2006015879 A1 | 2/2006 |
| WO | WO-2006029634 A2 | 3/2006 |
| WO | WO-2006051103 A2 | 5/2006 |
| WO | WO-2006051110 A2 | 5/2006 |
| WO | WO-2006058620 A2 | 6/2006 |
| WO | WO-2006110551 A2 | 10/2006 |
| WO | WO 2007/001150 | 1/2007 |
| WO | WO 2007/006307 | 1/2007 |
| WO | WO-2007024700 A2 | 3/2007 |
| WO | WO-2007028394 A2 | 3/2007 |
| WO | WO-2007031187 A1 | 3/2007 |
| WO | WO-2007035665 A1 | 3/2007 |
| WO | WO-2007036299 A2 | 4/2007 |
| WO | WO-2007037607 A1 | 4/2007 |
| WO | WO-2007044867 A2 | 4/2007 |
| WO | WO-2007050656 A2 | 5/2007 |
| WO | WO 2007/075534 | 7/2007 |
| WO | WO-2007081792 A2 | 7/2007 |
| WO | WO-2007081824 A2 | 7/2007 |
| WO | WO-2007082381 A1 | 7/2007 |
| WO | WO-2007095288 A2 | 8/2007 |
| WO | WO-2007104786 A1 | 9/2007 |
| WO | WO-2007109221 A2 | 9/2007 |
| WO | WO-2007113205 A1 | 10/2007 |
| WO | WO-2007120899 A2 | 10/2007 |
| WO | WO-2008006496 A1 | 1/2008 |
| WO | WO-2008013938 A2 | 1/2008 |
| WO | WO-2008021560 A2 | 2/2008 |
| WO | WO-2008023050 A1 | 2/2008 |
| WO | WO 2008/028914 | 3/2008 |
| WO | WO-2008034881 A1 | 3/2008 |
| WO | WO-2008124522 A2 | 10/2008 |
| WO | WO-2008133908 A2 | 11/2008 |
| WO | WO-2008145323 A1 | 12/2008 |
| WO | WO-2009004627 A2 | 1/2009 |
| WO | WO-2009030498 A2 | 3/2009 |
| WO | WO-2009030499 A1 | 3/2009 |
| WO | WO-2009039963 A1 | 4/2009 |
| WO | WO-2009048959 A1 | 4/2009 |
| WO | WO-2009056569 A1 | 5/2009 |
| WO | WO-2009063072 A2 | 5/2009 |
| WO | WO 2009/087082 | 7/2009 |
| WO | WO-2009087081 A2 | 7/2009 |
| WO | WO-2009089181 A1 | 7/2009 |
| WO | WO-2009098318 A1 | 8/2009 |
| WO | WO-2009102467 A2 | 8/2009 |
| WO | WO-2009134380 A2 | 11/2009 |
| WO | WO-2009143014 A1 | 11/2009 |
| WO | WO-2010030670 A2 | 3/2010 |
| WO | WO 2010/043566 | 4/2010 |
| WO | WO-2010044867 A1 | 4/2010 |
| WO | WO-2010089304 A1 | 8/2010 |
| WO | WO-2010092163 A2 | 8/2010 |
| WO | WO 2010/138671 | 12/2010 |
| WO | WO-2011012719 A1 | 2/2011 |
| WO | WO-2011017554 A2 | 2/2011 |
| WO | WO-2011029892 A2 | 3/2011 |
| WO | WO 2011/058082 | 5/2011 |
| WO | WO 2011/058083 | 5/2011 |
| WO | WO-2011089203 A1 | 7/2011 |
| WO | WO-2011103575 A1 | 8/2011 |
| WO | WO-2011122921 A2 | 10/2011 |
| WO | WO-2011128374 A1 | 10/2011 |
| WO | WO-2011144673 A2 | 11/2011 |
| WO | WO-2011144674 A2 | 11/2011 |
| WO | WO-2011147980 A1 | 12/2011 |
| WO | WO-2011157402 A1 | 12/2011 |
| WO | WO-2011160066 A1 | 12/2011 |
| WO | WO-2012012352 A2 | 1/2012 |
| WO | WO-2012028172 A1 | 3/2012 |
| WO | WO-2012055967 A2 | 5/2012 |
| WO | WO-2012065996 A2 | 5/2012 |
| WO | WO-2012066086 A1 | 5/2012 |
| WO | WO-2012080320 A1 | 6/2012 |
| WO | WO-2012104342 A1 | 8/2012 |
| WO | WO-2012125569 A2 | 9/2012 |
| WO | WO 2012/156296 | 11/2012 |
| WO | WO 2012/156299 | 11/2012 |
| WO | WO-2012177929 A2 | 12/2012 |
| WO | WO 2013/060850 | 5/2013 |
| WO | WO-2014017849 A1 | 1/2014 |
| WO | WO-2014118355 A1 | 8/2014 |

(56) References Cited

FOREIGN PATENT DOCUMENTS

| WO | WO-2014202483 A1 | 12/2014 |
|---|---|---|
| WO | WO 2015/059302 | 4/2015 |

OTHER PUBLICATIONS

Ahren et al., Abstract "Efficacy and Safety of Lixisenatide QD Morning and Evening Injections vs Placebo in T2DM Inadequately Controlled on Metformin (GetGoal-M)" Oral presentation O-0591 presented at the World Diabetes Congress in Dubai, Dec. 5-8, 2011, one page.
Arnolds et al., "Insulin Glargine (GLAR) plus Metformin (MET): An Efficacious and Safe Regimen that can be combined with Exenatide (EXE) or Sitagliptin (SITA)" Diabetes, 58(Suppl. 1): A141, Jun. 2009.
Barnett "Lixisenatide: evidence for its potential use in the treatment of type 2 diabetes." Core Evidence 6:67-79 (published online Sep. 8, 2011).
Barnett, "Insulin glargine in the treatment of type 1 and type 2 diabetes" Vascular Health and Risk Management 2:59-67 (published Jan. 25, 2006).
Bethel & Feinglos, "Basal insulin therapy in type 2 diabetes." J Am Board Fam Pract. 18(3):199-204 (May-Jun. 2005).
Bolen et al., "Systematic Review: Comparative Effectiveness and Safety of Oral Medications for Type 2 Diabetes Mellitus," Ann. Intern. Med. 147:386-399 (Epub Jul. 16, 2007).
Bolli et al., "Efficacy and safety of lixisenatide once-daily versus placebo in patients with type 2 diabetes mellitus insufficiently controlled on metformin (GetGoal-F1)." Presentation Abstract No. 784, EASD Meeting Sep. 12-16, 2014.
Bolli et al., "Efficacy and safety of lixisenatide once daily vs. placebo in people with Type 2 diabetes insufficiently controlled on metformin (GetGoal-F1)." Diabetic Medicine 31:176-184 (published online Oct. 24, 2013).
Byetta—Summary of Product Characteristics, updated Jan. 27, 2015, last accessed Apr. 18, 2015, pp. 1-12.
Charles et al., "Prevention of Type 2 Diabetes Role of Metformin" Review Article, Drugs 1999; 58 Suppl. 1:71-73 (Sep. 1999).
Childs et al., "Defining and Reporting Hypoglycemia in Diabetes," Diabetes Care 28(5):1245-9 (May 2005).
Christensen et al., "Lixisenatide for type 2 diabetes mellitus," Expert Opin. 20(4):549-57 (Epub Mar. 11, 2011).
Community register of medicinal products for human use, Chemical Subgroup A10BX, "Lyxumia" European Commision—Public Health, p. 1-2 (May 2, 2013).
Crapo et al., "Postprandial plasma-glucose and -insulin responses to different complex carbohydrates," Diabetes 26 (12):1178-83 (Dec. 1977).
Cryer "Hypoglycemia is the limiting factor in the management of diabetes," Diabetes Metab. Res. Rev. 15(1):42-46 (Jan.-Feb. 1999).
D'Alessio et al., "GLP-1 Receptor Agonists: Strategies for PPG Control," Medical Nursing Edu., 3:1-26 (Jan. 2011).
DeFronzo "Effects of Exenatide (Exendin-4) on Glycemic Control and Weight Over 30 Weeks in Metformin-Treated Patients with Type 2 Diabetes", Diabetes Care 28(5):1092-1100 (May 2005).
DeFronzo "Pathogenesis of Type 2 Diabetes Implications for Metformin" Short Communication, Drugs 1999; 58(Suppl 1):29-30 (Sep. 1999).
Distiller et al., Poster: "Pharmacokinetics and Pharmacodynamics of a New GLP-1 Agonist AVE0010 in Type 2 Diabetes Patients" Meeting: 68th Scientific Sessions (Jun. 2008) Poster No. 520-P.
Dormandy et al., "Secondary prevention of macrovascular events in patients with type 2 diabetes in the PROactive Study (PROspective pioglitAzone Clinical Trial in macrovascular Events): a randomised controlled trial," Lancet. 366(9493):1279-89 (Oct. 8, 2005).
Executive Summary, "Standards of Medical Care in Diabetes—2009" Diabetes Care,32(Suppl. 1):S6-S12 (Jan. 2009).
Gallwitz, "Liraglutide. GLP-1 Receptor Agonist Treatment of Type 2 Diabetes Treatment of Obesity," Drugs of the Future, 33(1):13-20 (Jan. 2008).
Gavin—Committee Report, "Report of the Expert Committee on the Diagnosis and Classification of Diabetes Mellitus," Diabetes Care, 20(7):1183-97 (Jul. 1997).
Gerich et al., "Monotherapy with GLP-1 receptor agonist, Lixisenatide, significantly improves glycaemic control in type 2 diabetic patients," Presentation abstract 830, 46th Annual Meeting of EASD, Stockholm, Sweden, pp. 1-3 (Sep. 2010).
Goldstein et al.. Tests of Glycemia in Diabetes. Diabetes Care 18(6):896-909 (Jun. 1995).
Hanas et al., "2010 Consensus Statement on the Worldwide Standardization of the Hemoglobin A1C Measurement." Diabetes Care 33(8):1903-04 (Aug. 2010).
Kapitza et al., Abstract "Pharmacodynamic Characteristics of Lixisenatide QD vs Liraglutide QD in Patients with T2DM Inadequately Controlled with Metformin" Abtract D-0740, presented at the World Diabetes Congress in Dubai, Dec. 5-8, 2011, one page.
Kanazawa et al., "Criteria and Classification of Obesity in Japan and Asia-Oceania", Asia Pacific J. Clin Nutr. 11 (Suppl. 7):S732-S737 (Dec. 2002).
Kendall et al., "Effets of Exenatide (Exendin-4) on Glycemic Control Over 30 Weeks in Patients With Type 2 Diabetes Treated With Metformin and a Sulfonylurea" Diabetes Care 28:1083-91 (May 2005).
NHSC—National Horizon Scanning Center, "AVE0010 (ZP10) for type 2 diabetes mellitus" University of Birmingham, England; pp. 1-6 (Dec. 2008).
Non-Final Rejection issued in U.S. Appl. No. 13/509,507; dated Dec. 8, 2015, pp. 1-14.
Search Report of the Intellectual Property Office of Singapore for Patent Application No. 10201500871T, dated Nov. 2, 2015, pp. 1-3.
Clinical Trials Archive for Trial No. NCT00688701 updated Sep. 30, 2012. Accessed at: https://clinicaltrials.gov/archive/NCT00688701/2012_09_30/changes Accessed on Jun. 2, 2016, pp. 1-5 submitted.
Clinical Trials History for Trial No. NCT00688701 last updated Mar. 25, 2014. Accessed at: https://clinicaltrials.gov/archive/NCT00688701 Accessed on Jun. 2, 2016, pp. 1-2 submitted.
International Search Report by the International Searching Authority for International Application No. PCT/EP2012/071271, dated Jan. 30, 2013, pp. 1-5.
International Search Report by the International Searching Authority for International Application No. PCT/EP2012/058779, dated Aug. 28, 2012, pp. 1-5.
International Search Report by the International Searching Authority for International Application No. PCT/EP2012/058745, dated Jul. 12, 2012, pp. 1-6.
International Search Report by the International Searching Authority for International Application No. PCT/EP2012/058749, dated Jul. 31, 2012, pp. 1-6.
International Search Report by the International Searching Authority for International Application No. PCT/EP2012/058747, dated Jul. 8, 2012, pp. 1-6.
International Search Report from the International Searching Authority for International Application No. PCT/EP2012/051670, dated Mar. 26, 2012, pp. 1-16.
International Search Report by the International Searching Authority for International Application No. PCT/EP2012/055660; dated May 10, 2012, pp. 1-6.
Non-Final Rejection issued in U.S. Appl. No. 13/363,956; dated Apr. 10, 2013, pp. 1-15.
Non-Final Rejection issued in U.S. Appl. No. 13/363,956; dated Nov. 20, 2013, pp. 1-10.
Final Rejection issued in U.S. Appl. No. 13/363,956; dated May 20, 2014, pp. 1-16.
Non-Final Rejection issued in U.S. Appl. No. 13/363,956; dated Feb. 11, 2015, pp. 1-18.
Non-Final-Rejection issued in U.S. Appl. No. 13/432,811; dated Apr. 8, 2013, pp. 1-7.
Non-Final-Rejection issued in U.S. Appl. No. 13/432,811; dated Jul. 29, 2014, pp. 1-8.

(56) References Cited

OTHER PUBLICATIONS

Final-Rejection issued in U.S. Appl. No. 13/432,811; dated Sep. 6, 2014, pp. 1-8.
Final-Rejection issued in U.S. Appl. No. 13/432,811; dated Dec. 12, 2014, pp. 1-8.
Final-Rejection issued in U.S. Appl. No. 13/432,811; dated Mar. 31, 2015, pp. 1-9.
Non-Final Rejection issued in U.S. Appl. No. 13/469,633; dated Mar. 27, 2013, pp. 1-39.
Non-Final Rejection issued in U.S. Appl. No. 13/469,633; dated Aug. 19, 2013, pp. 1-25.
Final Rejection issued in U.S. Appl. No. 13/469,633; dated Dec. 4, 2013, pp. 1-17.
Non-Final Rejection issued in U.S. Appl. No. 13/469,633; dated Aug. 22, 2014, pp. 1-23.
Final Rejection issued in U.S. Appl. No. 13/469,633; dated Jan. 23, 2015, pp. 1-12.
Non-Final Rejection issued in U.S. Appl. No. 13/467,707; dated Jul. 15, 2013, pp. 1-20.
Final Rejection issued in U.S. Appl. No. 13/467,707; dated Feb. 25, 2014, pp. 1-18.
Non-Final Rejection issued in U.S. Appl. No. 13/467,707; dated Jul. 25, 2014, pp. 1-22.
Final Rejection issued in U.S. Appl. No. 13/467,707; dated Jan. 7, 2015, pp. 1-8.
Non-Final Rejection issued in U.S. Appl. No. 13/467,757; dated Apr. 17, 2013, pp. 1-9.
Non-Final Rejection issued in U.S. Appl. No. 13/468,422; dated Mar. 27, 2013, pp. 1-27.
Non-Final Rejection issued in U.S. Appl. No. 13/468,422; dated Sep. 16, 2013, pp. 1-19.
Final Rejection issued in U.S. Appl. No. 13/468,422; dated Jan. 6, 2014, pp. 1-21.
Non-Final Rejection issued in U.S. Appl. No. 13/468,422; dated Jun. 4, 2014, pp. 1-24.
Final Rejection issued in U.S. Appl. No. 13/468,422; dated Jan. 23, 2015, pp. 1-27.
Final Rejection issued in U.S. Appl. No. 13/661,476, dated Oct. 2, 2014, pp. 1-33.
Non-Final Rejection issued in U.S. Appl. No. 13/661,476, dated Mar. 6, 2014, pp. 1-28.
Non-Final Rejection issued in U.S. Appl. No. 13/661,476, dated Dec. 4, 2013, pp. 1-11.
Non-Final Rejection issued in U.S. Appl. No. 13/661,476, dated Sep. 16, 2013, pp. 1-19.
Extended European Search Report for Application No. EP 11 15 3106, completed Jul. 6, 2011, pp. 1-12.
Extended European Search Report for European Application No. 11160270.2; dated Sep. 19, 2011, pp. 1-8.
Inpharma, Product News. "AVE0010 set to deliver in type 2 diabetes mellitus," Database Adisnews, retrieved from STN, Jun. 2008, pp. 1-3.
Insulinpraparat Wikipedia, http://de.wikipedia.org/wiki/Insulinpr%C3%A4parat, pp. 1-15 (Feb. 5, 2013).
Inzucchi et al. "Management of Hyperglycemia in Type 2 Diabetes: A Patient-Centered Approach" Diabetes Care, 35:1364-79 (Jun. 2012).
"Lixisenatide, Chemical Structure CID 16139342, Pubchem, accessed Feb. 5, 2015 at URLpubchem.ncbi.nlm.nih.gov/summary/summary.cgi?sid=135267128&viewopt=Deposited, pp. 1-3."
Liu & Ruus, Abstract "Pharmacokinetics and Safety of the GLP-1 Agonist AVE0010 in Patients with Renal Impairment," Diabetes 58 (Suppl. 1): Abstract 557-P for the 69th Scientific Session of the American Diabetes Association Jun. 5-9, 2009, New Orleans, Louisiana, pp. 1-2.
Medline Plus, "Obesity" available at http://www.nlm.nih.gov/medlineplus/obesity.html, Retrieved Aug. 22, 2013, one page.

Nauck et al., "Comparative evaluation of incretin-based antidiabetic medications and alternative therapies to be added to melformin in the case of monotherapy failure," Journal of Diabetes Investigation 1(1-2):24-36 (Feb.-Apr. 2010).
NCT00715624 Clinical Trials.gov "GLP-1 Receptor Agonist Lixisenatide in Patients With Type 2 Diabetes for Glycemic Control and Safety Evaluation, on Top of Basal Insulin (GETGOAL-L)" (2008-2014), p. 1-6 (Feb. 2011).
NCT00976937, ClinicalTrials.gov, "24-week Study Comparing Lixisenatide (AVE0010) to Sitagliptin as add-on to Metformin in Obese Type 2 Diabetic Patients Younger Than 50," May 6, 2011, Retrieved Nov. 7, 2011, pp. 1-4.
NCT00299871, ClinicalTrials.gov, "Dose Ranging Study of the GLP-1 Agonist AVE0010 in Metformin-Treated Subjects With Type 2 Diabetes Mellitus," Jun. 22, 2010, Retrieved Nov. 7, 2011, pp. 1-5.
NCT00975286, Clinical Trials.gov, "24-week Treatment with Lixisenalide in Type 2 Diabetes Insufficiently Controlled With Melformin and Insulin Glargine", Aug. 8, 2011, pp. 1-4.
EFC10780 (Sanofi study), "A randomized, double-blind, double-dummy, 2-arm parallel-group, multicenter 24-week study comparing the efficacy and safety of AVE0010 to sitagliptin as add-on to metformin in obese type 2 diabetic patients younger than 50 and not adequately controlled with metformin (EFC10780)" p. 1-4 (Jan. 29, 2014).
EFC10781 Clinical Trials, "24-week Treatment With Lixisenatide in Type 2 Diabetes Insufficiently Controlled With Metformin and Insulin Glargine" ClinicalTrials.gov; EFC10781 pp. 1-5 (Sep. 2009).
Park et al., "PPARalpha agonis fenofibrate improves diabetic nephropathy in db/db mice," Kidney International, 69:1511-17 (published online Mar. 1, 2006).
Pugeat et al., "Insulin Resistance, Polycystic Ovary Syndrome and Metformin" Review Article, Drugs 1999; 58(Suppl 1):41-46 (Sep. 1999).
Quianzon & Shomali, "Lixisentide-Once Daily Glucagon-like Peptide-1 receptor Agonist in the Management of Type 2 Diabetes", US Endocrinology, 7(2):104-9 (Winter 2011).
Ratner et al. Abstract 131 "Post-meal pharmacodynamics profile of AVE0010, a once-daily GLP-1 receptor agonist, in patiens with type 2 diabetes inadequately controlled on metformin" Diabetologia 52(Suppl. 1): S60, #131 (Sep. 2009).
Richter, von Margret, "Oldtimer as Newcomer" Pharmazie, pp. 1-9; http://www.pharmazeutische-zeitung.de/pza/2002-12/pharm1.htm (Feb. 2002).
Riddle et al., Contributions of Basal and Postprandial Hyperglycemia Over a Wide Range of A1C Levels Before and After Treatment Intensification in Type 2 Diabetes, Diabetes Care 34:2508-2514 (published online Oct. 25, 2011).
Riddle et al., "Adding Once-Daily Lixisenatide for Type 2 Diabetes Inadequately Controlled with Newly Initiated and Continuously Titrated Basal Insulin Glargine" Diabetes Care, pp. 2497-2503 (Sep. 2013).
Rosenstock et al., Abstract, "71st Scientific Sessions" http://www.call4abstracts.com/ada/ada11d11b/index.php 02:22:24 pp. 1-3, (Nov. 2011).
Rosenstock et al., Poster "Efficacy and safety of lixisenatide once daily vs exenatiide twice daily in type 2 DM inadequately controlled on metformin (GetGoal-X)." 71st Scientific Sessions (Nov. 2011).
Sanofi Press Release; "Lyxumia (lixisenatide) in Combination with Basal insulin plus Oral Anti-Diabetics Significantly Reduced HbA1c and Post-Prandial Glucose"; Paris, France (Jun. 9, 2012) pp. 1-6.
Sanofi-aventis Press Release, "Once Daily Lixisenatide (AVE 0010) Given as Monotherapy Successfully Meets Phase III Study Endpoints in Diabetes" Paris, France (Apr. 15, 2010) pp. 1-2.
Sanofi Press Release (Peron and Schaeffer), "Sanofi GetGoal Program on Lyxumia®, as an Add-on to Basal Insulin, Shows Significant Positive Phase III Results," Paris, France (May 31, 2011) pp. 1-2.
Sanofi Press release (Peron and Schaeffer); "Sanofi Reports Positive Results for Once-daily Lyxumia® (lixisenatide) in combination with Lantus® (insulin glargine) in Type 2 Diabetes" Paris, France (Dec. 6, 2011) pp. 1-3.

(56) References Cited

OTHER PUBLICATIONS

Sanoti-aventis Press Release (Gabriel), "New Diabetes Compound AVE0010 Showed Clear Dose Response Results With Once-A-Day Injection in Phase IIb Study" Paris, France (Jun. 7, 2008) pp. 1-2.
Sanoti-aventis Press Release (Peron and Schaeffer), "Sanofi-aventis Announces Positive Top-line Lixisentatide Phase III Results" Paris, France (Feb. 2, 2011) pp. 1-2.
Sanofi Press Release (Peron and Schaeffer), "Lyxumia® (lixisenatide) One-Step Regimen as Effective as Two-Step Regimen in Improving Glycemic Control in Type 2 Diabetes" Paris, France (Sep. 12, 2011) pp. 1-3.
Sanofi Press Release (Sigurd), "Lixisenatide Significantly Reduces HbA1c Without Increasing Hypoglycemia in Patients Uncontrolled on Sulfonylureas", Pressmeddelande (Apr. 12, 2011) pp. 1-2.
Sanofi and Zealand Pharma Press Release (Evaluate), "Additional Positive Results from Global Phase III Program With Lixisenatide for Type 2 Diabetes", (Apr. 12, 2011) pp. 1-3.
Sharplin et al., "Improved glycaemic control by switching from insulin NPH to insulin glargine: a retrospective observational study," Cardiovascular Diabetology, 8(3):1-8 (published Jan. 19, 2009).
St. John Providence Health Center, "Preventing Obesity" http://www.stjohnprovidence.org/HealthInfolib/swarticle.aspx?type=85&id= P07863, Retrieved Aug. 22, 2013, pp. 1-2.
Summary of Product Characteristics Lyxumia 10 micrograms solution for injection, pp. 1-93, with European Medicines Agency product information, p. 94, published Mar. 14, 2013.
Tews et al., "Enhanced protection against cytokine- and fatty acid-induced apoptosis in pancreatic beta cells by combined treatment with glucagon-like peptide-1 receptor agonists and insulin analogues." Horm Metab Res. 40(3):172-80 (Mar. 2008).
UK Prospective Diabetes Study (UKPDS) Group "Intensive blood-glucose control with sulphonylureas or insulin compared with conventional treatment and risk of complications in patients with type 2 diabetes (UKPDS 33)" The Lancet vol. 352 p. 837-853 (Sep. 12, 1998).
WHO Drug Information vol. 22(2), list 99, p. 142 (lixisenatide) (Jul. 2008).
Wiernsperger, et al. "The Antihyperglycaemic Effect of Metformin Therapeutic and Cellular Mechanisms" Review Article, Drugs 1999:58(Suppl 1):31-39 (Sep. 1999).
Yki-Jarvinen et al., "Insulin glargine or NPH combined with metformin in type 2 diabetes: the LANMET study." Diabetologia 49(3):442-51 (Mar. 2006).
Yki-Jarvin et al., "Thiazolidinediones," N Engl J Med. 351(11):1106-18 (Sep. 2004).
Zimmet, et al. "Clinical Efficacy of Metformin against Insulin Resistance Parameters, Sinking the Iceberg" Review Article, Drugs 1999: 58(Suppl 1):21-28 (Sep. 1999).
American Diabetes Association, "Standards of Medical Care in Diabetes-2011 ", Diabetes Care, 34 (Supplement 1): S11-S61 (Jan. 2011).
Aquiliante, "Sulfonylurea pharmacogenomics in type 2 diabetes: the influence of drug target and diabetes risk polymorphisms" Expert Rev Cardiovasc Ther. 8(3):359-72 (Mar. 2010).
Canadian Cardiovascular Society Grading of Angina Pectoris. From http://www.sscts.org/pages/classificationanginaccs.aspx. Accessed May 27, 2016, one page.
Cannon et al. For the Pravastatin or Atorvastatin Evaluation and Infection Therapy-Thrombolysis in Myocardial Infarction Investigators. "Intensive versus Moderate Lipid Lowering with Statins after Acute Coronary Syndromes." N Engl J Med 350(15):1495-504 (Apr. 2004; Epub Mar. 8, 2004).
Das et al., "The British Cardiac Society Working group definition of myocardial infarction: implications for practice." Heart 92(1):21-6 (Jan. 2006; Epub Apr. 14, 2005).
DCCT, Diabetes Control and Complications Trial/ Epidemiology of Diabetes Interventions and Complications Research Group: Intensive diabetes therapy and carotid intima-media thickness in type 1 diabetes. N Engl J Med 348 (23):2294-303 (Jun. 2003).
DCCT, Diabetes Control and Complications Trial/ Epidemiology of Diabetes Interventions and Complications Research Group: Intensive diabetes treatment and cardiovascular disease in patients with type 1 diabetes. N Engl J Med. 353 (25):2643-59 (Dec. 2005).
Definition of Phase, Clinical Trials.gov NIH, accessed Mar. 16, 2016, one page.
European Medicines Agency, Committee for Medicinal Products for Human Use (CHMP), "Assessment report—Lyxumia", pp. 1-81 (Nov. 28, 2012).
EMA—European Medicines Agency, "Note for guidance on non-clinical safety studies for the conduct of human clinical trials and marketing authorization for pharmaceuticals" pp. 1-22 (Jul. 2008).
FDA—Food and Drug Administration, CFR—Code of Federal Regulations Title 21, Chapter 1, Subchapter D, Part 312.21, "Phases of an investigation" pp. 1-2, Apr. 1, 2015.
Forman et al., "Higher levels of albuminuria within the normal range predict incident hypertension." J Am Soc Nephrol 19(10):1983-88 (Oct. 2008).
Hinnen, "Therapeutic Options for the Management of Postprandial Glucose in Patients With Type 2 Diabetes on Basal Insulin" Clinical Diabetes 33(4):175-80 (2015).
IDF, International Diabetes Federation Guideline Development Group, "Guideline for management of postmeal glucose in diabetes" Diabetes Res Clin Pract, pp. 1-13, (2012).
Johnson et al., "Diabetes, Insulin Resistance, and Metabolic Syndrome in Horses" Journal of Diabetes Science and Technology, 6(3):534-40 (May 2012).
Kelly et al., "Systematic review: glucose control and cardiovascular disease in type 2 diabetes." Ann Intern Med 151 (6):394-403 (Sep. 2009; Epub Jul. 20, 2009).
Kendall et al., "Clinical Application of Incretin-Based Therapy: Therapeutic Potential, Patient Selection and Clinical Use." European Journal of Internal Medicine. 20(Suppl 2):S329-39 (Jul. 2009).
Khaw et al., "Glycated haemoglobin, diabetes, and mortality in men in Norfolk cohort of European Prospective Investigation of cancer and Nutrition (EPIC Norfolk)." BMJ 322(7277):15-18 (Jan. 2001).
Kim et al., "Retinopathy in Monkeys with Spontaneous Type 2 Diabetes" Investigative Opth & Visual Science, 45(12):4543-53 (Dec. 2004).
Madsbad, "Impact of postprandial glucose control on diabetes-related complications: How is the evidence evolving?" Journal of Diabetes and Its Complications, 30:374-85 (2016; available online Oct. 9, 2015).
Miyazaki et al., "Improved glycemic control and enhanced insulin sensitivity in type 2 diabetic subjects treated with pioglitazone", Diabetes Care, 24(4):710-19 (Apr. 2001).
Monnier et al., "Postprandial and Basal Glucose in Type 2 Diabetes: Assessment and Respective Impacts" Diabetes Technology & Therapeutics, 13(Supplement 1):S25-S32 (2011).
Nathan et al., "Medical Management of Hyperglycemia in Type 2 Diabetes: A Consensus Algorithm for the Initiation and Adjustment of Therapy" Diabetes Care 32(1):193-203 (Jan. 2009).
NCT00866658 ClinicalTrials.gov, "GLP-1 agonist AVE0010 in patients with type 2 diabetes for glycemic control and safety evaluation, on top of basal insulin +/--sulfonylurea" p. 1-3, accessed Mar. 16, 2016 (updated Jan. 19, 2010).
NCT01169779, Clinical Trials.gov, "Efficacy and Safety of Lixisenatide in Patients with Type 2 diabetes mellitus insufficiently controlled by metformin," pp. 1-3, accessed Mar. 16, 2016 (updated Mar. 28, 2011).
Nice, National Institute for Health and Care Excellence, "Evidence summary: new medicine, ESNM26: Type 2 diabetes: lixisenatide; Key points from the evidence" pp. 1-26 (Sep. 24, 2013).
Park et al., "Long-term treatment of glucagon-like peptide-1 analog exendin-4 ameliorates diabetic nephropathy through improving metabolic anomalies in db/db mice." J Am Soc Nephrol, 18(4):1227-38 (Apr. 2007; Epub Mar. 14, 2007).
"Remington: The Science and Practice of Pharmacy", Twentieth Edition, Lippincott Williams & Wilkins, USA, pp. 1-5, 2000.
Sanofi-aventis Press Release, "A promising R&D portfolio, well positioned to deliver future growth" (dated Sep. 17, 2007) pp. 1-11.
Sanofi Presentation, "Natixis Conference on Diabetes" Pierre Chancel, pp. 1-23, Nov. 8, 2011.

(56) References Cited

OTHER PUBLICATIONS

Spertus et al., "Development and evaluation of the Seattle Anginal Questionnaire: a new functional status measure for coronary artery disease." J Am Coli Cardiol. 25(2):333-41 (Feb. 1995).
Spertus et al., "Health status predicts long-term outcome in outpatients with coronary disease." Circulation. 106(1):43-49 (Jul. 2002).
Srinivasan & Ramarao, "Animal models in type 2 diabetes research: An overview." Indian J Med Res. 125:451-472 (Mar. 2007).
The Advance Collaborative Group, "Intensive blood glucose control and vascular outcomes in patients with type 2 diabetes." N Engl J Med 358(24):2560-72 (Jun. 2008).
UK Prospective Diabetes Study (UKPDS) Group, "Tight blood pressure control and risk of macrovascular and microvascular complications in type 2 diabetes (UKPDS 38)." BMJ 317:703-13 (Sep. 1998).
Wikipedia® entry for "Lixisenatide" Retrieved from the Internet: https://en.wikipedia.org/wiki/Lixisenatide one page, retrieved Apr. 11, 2016.
Wikipedia® entry for "Pioglitazone" Retrieved from the Internet: https://en.wikipedia.org/wiki/Pioglitazone pp. 1-3, retrieved Apr. 11, 2016.
Wikipedia® entry for "Metformin" Retrieved from the Internet: https://en.wikipedia.org/wiki/Metformin pp. 1-21, retrieved Apr. 11, 2016.
Wikipedia® entry for "Body mass index" Retrieved from the Internet: https://en.wikipedia.org/wiki/Body mass_index pp. 1-14, retrieved Feb. 26, 2016.
World Health Organisation report on "Definition and diagnosis of diabetes mellitus and intermediate hyperglycemia: report of a WHO/IDF consultation" pp. 1-50 (2006).
Wiviott et al., "Greater Clinical Benefit of More Intensive Oral Antiplatelet Therapy With Prasugrel in Patients With Diabetes Mellitus in the Trial to Assess Improvement in Therapeutic Outcomes by Optimizing Platelet Inhibition With Prasugrel-Thrombolysis in Myocardial Infarction 38." Circulation 118(16):1626-36 (Oct. 2008; Epub Aug. 31, 2008).
Yusuf et al., "Effects of clopidogrel in addition to aspirin in patients with acute coronary syndromes without ST-segment elevation." N Engl J Med 345(7):494-502 (Aug. 2001).
Zoungas et al, "Combined Effects of Routine Blood Pressure Lowering and Intensive Glucose Control on Macrovascular and Microvascular Outcomes in Patients With Type 2 Diabetes. New results from the Advance trial." Diabetes Care 32(11):2068-74 (Nov. 2009; Epub Aug. 3, 2009).
Final Rejection issued in U.S. Appl. No. 13/382,772; dated Feb. 24, 2016, pp. 1-36.
Final Office Action from U.S. Appl. No. 12/617,805; dated May 25, 2016, pp. 1-9.
Final Rejection issued in U.S. Appl. No. 14/303,895; dated Apr. 27, 2015, pp. 1-10.
Extended European Search Report for European Application No. 15 15 9064.3; dated Oct. 19, 2015, pp. 1-4.
U.S. Appl. No. 13/382,772, filed May 29, 2012, Schoettle.
U.S. Appl. No. 13/382,442, filed Feb. 21, 2012, Schoettle.
U.S. Appl. No. 13/509,507, filed Jul. 30, 2014, Brunner-Schwarz et al.
U.S. Appl. No. 13/509,542, filed Aug. 2, 2012, Hagendorf et al.
U.S. Appl. No. 14/172,151, filed Feb. 4, 2014, Bley et al.
U.S. Appl. No. 12/617,805, filed Nov. 13, 2009, Silvestre et al.
U.S. Appl. No. 12/617,811, filed Nov. 13, 2009, Silvestre et al.
U.S. Appl. No. 14/220,562, filed Mar. 20, 2014, Becker et al.
U.S. Appl. No. 13/700,631, filed Nov. 11, 2012, Becker et al.
U.S. Appl. No. 13/595,590, filed Aug. 27, 2012, Niemoller et al.
U.S. Appl. No. 13/602,913, filed Sep. 4, 2012, Hess et al.
U.S. Appl. No. 13/633,563, filed Oct. 2, 2012, Stechl et al.
U.S. Appl. No. 13/123,835, filed Sep. 30, 2011, Werner et al.
U.S. Appl. No. 13/633,496, filed Oct. 2, 2012, Stechl et al.
U.S. Appl. No. 14/303,895, filed Jun. 13, 2014, Souhami et al.
U.S. Appl. No. 14/965,586, filed Dec. 10, 2015, Souhami et ai.
U.S. Appl. No. 14/995,910, filed Jan. 14, 2016, Bergmann et al.
U.S. Appl. No. 15/073,364, filed Mar. 17, 2016, Belder et al.
U.S. Appl. No. 15/068,286, filed Mar. 11, 2016, Roy et al.
U.S. Appl. No. 13/819,114, filed Apr. 29, 2013, Boka et al.
U.S. Appl. No. 13/363,956, filed Feb. 1, 2012, Silvestre et al.
U.S. Appl. No. 13/432,811, filed Mar. 28, 2012, Boka et al.
U.S. Appl. No. 13/469,633, filed May 11, 2012, Ruus et al.
U.S. Appl. No. 13/467,707, filed May 9, 2012, Niemoller et al.
U.S. Appl. No. 13/468,422, filed May 10, 2012, Silvestre et al.
U.S. Appl. No. 13/467,757, filed May 9, 2012, Silvestre et al.
U.S. Appl. No. 13/661,476, filed Oct. 26, 2012, Silvestre et al.
Abraira et al., "Glycaemic separation and risk factor control in the Veterans Affairs Diabetes Trial: an interim report" Diabetes Obes Metab 11(2):150-56 (2009; Epub Jul. 29, 2008).
Aguilar, "Heart failure and diabetes: Time to pay attention" American Heart Journal, 162(5):795-97 (Nov. 2011).
Ampudia-Blasco et al., "Basal Plus Basal-Bolus approach in type 2 diabetes" Diabetes Technol Ther. 13 Suppl1: S75-83 (Jun. 2011).
Atkinson et al., "validation of a general measure of treatment satisfaction, the Treatment Satisfaction Questionnaire for Medication (TSQM), using a national panel study of chronic disease" Health Qual Life Outcomes, 2:12, pp. 1-13 Feb. 2004).
Beckman et al., "Diabetes and atherosclerosis: epidemiology, pathophysiology, and management" JAMA 287 (19):2570-81 (May 2002).
Bentley-Lewis et al., "Rationale, design, and baseline characteristics in Evaluation of LIXisenatide in Acute Coronary Syndrome, a long-term cardiovascular end point trial of lixisenatide versus placebo" American Heart Journal, 169(5):631-38 (May 2015; Epub Feb. 11, 2015).
Brazier et al., "Testing the validity of the Euroqol and comparing it with the SF-36 health survey questionnaire," Qual Life Res 2(3):169-80 (Jun. 1993).
Byetta® Product information, EMA pp. 1-2, accessed Jun. 10, 2016.
Byetta® Summary of product characteristics, ANNEX I, pp. 1-71, (2011).
Classification of Functional Capacity and Objective Assessment, My.AmericanHeart, 1994—last accessed Oct. 23, 2015, pp. 1-2.
Clinical Trials Archive for Trial No. NCT00688701 updated Sep. 30, 2012. Accessed at: https://clinicaltrials.gov/ archive/ NCT00688701/2012.09.30/changes Accessed on Jun. 2, 2016, pp. 1-5 submitted.
D'Alessio et al., "The role of dysregulated glucagon secretion in type 2 diabetes" Diabetes, Obesity and Metabolism, 13(Supppl.1):126-132 (Oct. 2011).
De Lemos et al., "Early intensive vs. a delayed conservative simvastatin strategy in patients with acute coronary Syndromes: phase Z of the A to Z trial." JAMA 292(11):1307-16 (Sep. 2004; Epub Aug. 30, 2004).
Definition of "Combination", Concise Oxford English Dictionary, edited by A. Stevenson and M. Waite, Oxford University press, 12th Edition, Aug. 2011, 4 pages submitted, see p. 285.
Del Prato & Tiengo, "The importance of first-phase insulin secretion: implications for the therapy oftype 2 diabetes mellitus." Diabetes Metab Res Rev. 17(3):164-74 (May-Jun. 2001).
Del Prato et al., "Global Partnership for Effective Diabetes Management Tailoring treatment to the individual in type 2 diabetes practical guidance from the Global partnership for effective diabetes management" Int J Clin Pract 64 (3):295-304 (Feb. 2010).
DeWitt & Hirsch, "Outpatient insulin therapy in type 1 and type 2 diabetes mellitus: scientific review." JAMA 289 17):2254-64 (May 2003).
Dinneen & Gerstein, "The association of microalbuminuria and mortality in non-insulin dependent diabetes mellitus. A systematic overview of the literature." Arch Intern Med 157(13):1413-8 (Jul. 1997).
Dolan, "Modeling valuations for EuroQol health states." Med Care 35(11):1095-1108 (Nov. 1997).
Dunning & Gerich, "The Role of alpha-cell Dysregulation in Fasting and Postprandial Hyperglycemia in Type 2 Diabetes and Therapeutic Implications" Endocrine Reviews 28(3):253-83 (Apr. 2007).
Encyclopedia of Drugs, "METFORMIN" Moscow, Drug Register of 2001, p. 549, English translation provided pp. 1-2.

(56) References Cited

OTHER PUBLICATIONS

European Public Assessment Report (EPAR) Optisulin, EPAR Summary for the Public. Feb. 2009, pp. 1-3.
EuroQol Group, "EuroQol—a new facility for the measurement of health-related quality of life." Health policy (Amsterdam, Netherlands) 16(3):199-208 (Dec. 1990).
FDA, Food and Drug Administration. Guidance for Industry—Diabetes Mellitus: Developing Drugs and Therapeutic Biologics for Treatment and Prevention. pp. 1-34 (Feb. 2008).
Final Rejection in U.S. Appl. No. 13/633,496; dated Aug. 26, 2015, pp. 1-16.
Final Rejection in U.S. Appl. No. 13/633,563; dated Apr. 8, 2016, pp. 1-12.
Final Rejection issued in U.S. Appl. No. 13/509,507; dated May 13, 2016, pp. 1-11.
Game, "Novel hypoglycaemic agents: Considerations in patients with chronic kidney disease" Nephron Clin Pract.126(1):14-18 (Jan. 11, 2014).
Gerstein et al., "Albuminuria and risk of cardiovascular events, death, and heart failure in diabetic and nondiabetic Individuals." JAMA 286(4):421-6 (Jul. 2001).
Giorda et al., "Pharmacokinetics, safety, and efficacy of DPP-4 inhibitors and GLP-1 receptor agonists in patients with type 2 diabetes mellitus and renal or hepatic impairment. A systematic review of the literature." Endocrine 46(3):406-19 (Aug. 2014; epub Feb. 8, 2014).
Gromada et al., "Alpha-Cells of the Endocrine Pancreas: 35 Years of Research but the Enigma Remains" Endocrine Reviews 28(1):84-116 (Jan. 2007).
Harkavyi & Whitton, "Glucagon-like peptide 1 receptor stimulation as a means of neuroprotection" British Journal of Pharmacology 159(3):495-501 (2010; Epub Jan. 29, 2010).
Hasslacher et al., "Diabetic kidney disease" Expand Clin Endocrinol Diabetes 122(7):391-94 (Jul. 2014).
Holman et al., "Three-year efficacy of complex insulin regimens in type 2 diabetes." N Engl J Med. 361 (18):1736-47 (Oct. 2009; Epub Oct. 22, 2009).
Hubschle et al., "Anti-atherosclerotic activity of lixisenatide in ApoE knockout mice" Abstract 809, Diabetologia, 55 (Supplement 1 ):S334 (Oct. 2012).
International Search Report by the ISA for International Application No. PCT/EP2016/055267; dated Jun. 7, 2016, pp. 1-7.
International Search Report by the ISA for International Application No. PCT/EP2016/055267; dated May 20,2016, pp. 1-7.
International Search Report by the ISA for International Application No. PCT/EP2016/055954; dated Sep. 9, 2016, pp. 1-12.
Inzucchi et al., "Management of hyperglycaemia in type 2 diabetes: a patient-centered approach. Position statement of the American Diabetes Association (ADA) and the European Association for the Study of Diabetes (EASD)." Diabetologia. 55(6):1577-96 (Jun. 2012; Epub Apr. 20, 2012).
Juniper et al., "Determining a minimal important change in a disease-specific quality of life questionnaire." J Clin Epidemiol47(1):81-87 (Jan. 1994).
Katz et al., "The clinical burden of type 2 diabetes in patients with acute coronary syndromes: Prognosis and implications for short- and long-term management" Diabetes and Vascular Disease Research, 11 (6):395-409 (Nov. 2014).
King et al., Global burden of diabetes, 1995-2025. Prevalence, numerical estimates and projections. Diabetes Care 21(9):1414-31 (Sep. 1998).
Kolotkin et al., "Assessing impact of weight on quality of life." Obes Res. 3(1 ):49-56 (Jan. 1995).
Kolotkin et al., "Development of a brief measure to assess quality of life in obesity." Obes Res. 9(2):102-11 (Feb. 2001).
Kondrat'ev VA Methodical Guidelines, May 7, 2010, p. 5 (in Russian only), found on Mar. 24, 2016, found from Internet: StudFields.ru>preview/4510743).
Korytkowski, "When oral agents fail: practical barriers to starting insulin." Int J Obes Relat Metab Disord. 26 Suppl 3 :S18-24 (Sep. 2002).
Lovshin & Drucker, "Incretin-based therapy for type 2 diabetes mellitus." Nat. Rev. Endocrinol. 5(5):262-69 (May 2009).
McFarlane, "Insulin therapy and type 2 diabetes: management of weight gain," J Clin Hypertens (Greenwich). 11 (10):601-7 (Oct. 2009).
Meadows et al., "Adaptation of the diabetes health profile (DHP-1) for use with patients with Type 2 diabetes mellitus: psychometric evaluation and cross-cultural comparison," Diabet. Med. 17(8):572-80 (Aug. 2000).
Meadows et al, "The diabetes health profile (DHP): a new instrument for assessing the psychosocial profile of insulin requiring patients: development and psychometric evaluation," Qual. Life Res. 5(2):242-54 (Apr. 1996).
Meier et al., "Contrasting Effects of Lixisenatide and Liraglutide on Postprandial Glycemic Control, Gastric Emptying, and Safety Parameters in Patients With Type 2 Diabetes on Optimized Insulin Glargine With or Without Metformin: A Randomized, Open-Label Trial" Diabetes Care 38(7):1263-73 (Jul. 2015).
Meier et al., "Effect of lixisenatide vs liraglutide on glycaemic control, gastric emptying and safety parameters in optimised insulin glargine type 2 diabetes mellitus +/− metformin" Abstract and Poster 926, 5oth EASD Annual Meeting, Vienna, Austria Sep. 15-19, 2014, pp. 1-3.
Meigs et al., "Body Mass Index, Metabolic Syndrome, and Risk of Type 2 Diabetes or Cardiovascular Disease" Journal of Clinical Endocrinology & Metabolism, 91(8):2906-12 (Aug. 2006).
Merck Index, "Metformin", The Merck Index, 15th Edition (2013), RSC Publishing, 4 pages submitted, see entry 6009, p. 1102.
Monnier & Colette, "Addition of rapid-acting insulin to basal insulin therapy in type 2 diabetes: indications and modalities." Diabetes Metab 32(1):7-13 (Feb. 2006).
Nathan et al., "Modem-day clinical course of type 1 diabetes mellitus after 30 years' duration: the diabetes control and complications trial/epidemiology of diabetes interventions and complications and Pittsburgh epidemiology of diabetes complications experience (1983-2005)." Arch Intern Med. 169(14):1307-16 (Jul. 2009).
NCT00713830, Clinical Trials.gov "GLP-1 Agonist in Patients with Type 2 Diabetes for Glycemic Control and Safety Evaluation, on Top of Sulfonylurea", 2016, pp. 1-3, accessed Mar. 16, 2016, (Updated Jul. 13, 2008).
NCT00976937, ClinicaiTrials.gov, "24-week Study Comparing Lixisenatide (AVE001 0) to Sitagliptin as add-on to Metformin in Obese Type 2 Diabetic Patients Younger Than 50," last updated Mar. 10, 2014, Retrieved Aug. 31, 2016, pp. 1-5.
NIH, National Institute of Diabetes and Digestive and Kidney Disease, "Hypoglycimia," Mar. 16, 2016, pp. 1-8.
Nihonn-lyakuhin-shu Iryoyaku "Pioglitazone hydrochloride, Insulin sensitizing hypoglycemic agent" 2009 Edition, Jiho Inc. page 1901 (2009). English summary submitted.
Non-Final Rejection in U.S. Appl. No. 13/633,496; dated Apr. 21, 2016, pp. 1-12.
Non-Final Rejection issued in U.S. Appl. No. 13/467,707; dated Jun. 30, 2016, pp. 1-9.
Nowels et al., "Validation of the EQ-50 quality of life instrument in patients after myocardial infarction." Qual Life Res 14(1):95-105 (Feb. 2005).
Paniker et al., "Beneficial effects of triple drug combination of pioglitazone with glibenclamide and metformin in type 2 diabetes mellitus patients on insulin therapy," J Assoc Physicians India, 51:1061-64 (Nov. 2003).
Partial International Search Report by the ISA for International Application No. PCT/EP2016/055954; dated Jun. 21, 2016, pp. 1-6.
Patel et al., "Stability Considerations for Biopharmaceuticals: Overview of Protein and Peptide Degradation Pathways" Available online at: http://www.bioprocessint.com/manufacturing/formulation/biopharmaceutical-product-stability-considerations-part-1/, 23 pages (2011).

(56) References Cited

OTHER PUBLICATIONS

Petersen & Christensen et al., Clinical potential of lixisenatide once daily treatment for type 2 diabetes mellitus Diabetes, Metabolic Syndrome and Obesity: Targets and Therapy, 6:217-31 (Jun. 2013).
Petrie, "The cardiovascular safety of incretin-based therapies: a review of the evidence" Cardiovascular Diabetology, 12(1):130, 12 pages (Sep. 2013).
Pi-Sunyer, "The Impact of Weight Gain on Motivation, Compliance, and Metabolic Control in Patients with Type 2 Diabetes Mellitus." Postgrad Med. 121(5):94-107 (Sep. 2009).
Ratner et al., "Efficacy and safety of lixisenatide once-daily versus placebo in patients with type 2 diabetes mellitus insufficiently controlled on sulfonylurea +/− metformin (GetGoal-S)" Presentation Abstract for Presentation No. 785. 47th EASD Annual Meeting, Lisbon, Sep. 12-16, 2011, pp. 1-3.
Ray et al., "Effect of intensive control of glucose on cardiovascular outcomes and death in patients with diabetes mellitus: a meta-analysis of randomized controlled trials." Lancet 373(9677):1765-72 (May 2009).
Register of medicaments (RM), 2003, issue 10, p. 517.
Remington: The Science and Practice of Pharmacy, Twentieth Edition, Lippincott Williams & Wilkins, USA, "Oral Hypoglycemic and Hyperglycemic Drugs" pp. 1373 and 1375; (2000).
Rosenstock J et al., Advancing Basal Insulin Glargine with Prandial Lixisenatide QD vs. Insulin Glulisine QD or TID in T2DM: The GetGoaiDuo2 Evidence-Based Trial (NCT01768559). Poster 107 -LB, Presented on Sunday, Jun. 7, 2015, 75th Scientific Sessions of the American Diabetes Association, Boston, Massachusetts Jun. 5-9, 2015.
Ruetten et al., "Protective effects of the GLP-1 receptor agonist lixisenatide on ischaemia-reperfusion-induced myocardial infarction in an isolated rat heart model" Diabetologia, Abstract 810, 54(Supplement 1):S329 (Sep. 2011).
Russell-Jones & Khan, Insulin-associated weight gain in diabetes: causes, effects and coping strategies. Diabetes Obes Metab. 9(6):799-812 (Nov. 2007).
Sanofi Press Release entitled "Sanofi Announces Top-Line Results for Cardiovascular Outcomes Study of Lyxumia® (lixisenatide)." dated Mar. 19, 2015, Paris, France, pp. 1-2.
Schernthaner et al., "Is the ADA/EASD algorithm for the management of type 2 diabetes (Jan. 2009) based on evidence or opinion? A critical analysis." Diabetologia.53(7):1258-69 (Jul. 2010; Epub Mar. 31, 2010).
Seino et al., "Lixisenatide significantly improves glycemic control in Asian patients with T2DM insufficiently controlled on basal insulin± SU." Diabetes, Abstract book for 71st Scientific Session. p. A76; Abstract 278-0R. (2011).
Shaw et al., "US valuation of the EQ-5D health states: development and testing of the D1 valuation model." Med Care 43(3):203-20 (Mar. 2005).
Sillars et al., "Sulphonylurea-metformin combination therapy, cardiovascular disease and allcause mortality: the Fremantle Diabetes Study." Diabetes Obes Metab. 12(9):757-65 (Sep. 2010).
Spertus et al., "Monitoring the quality of life in patients with coronary heart disease." Am J Cardiol. 74(12):1240-44 (Dec. 1994).
Standardized Definitions for Cardiovascular Outcomes Trials: Draft Recommendations. Division of Metabolism and Endocrinology Products. Center for Drug Evaluation and Research (COER). pp. 1-34, Mar. 24, 2010.
The Criteria Committee of the New York Heart Association, "Nomenclature and Criteria for Diagnosis of Diseases of the Heart and Great Vessels." 9th edition. Boston, Mass: Little, Brown & Co; pp. 253-256 (1994).
Tirosh et al., "Normal Fasting Plasma Glucose Levels and Type 2 Diabetes in Young Men" New England Journal of Medicine, 353(14):1454-62 (Oct. 2005).
Weir "Glucagon-like peptide-1 (7-37) actions on endocrine pancreas." Diabetes 38(3):338-42 (Mar. 1989).

WHO, World Health Organization Media Center. Diabetes Fact Sheet. Available from: http://www.who.int/mediacentre/factsheets/fs312/en/index.html. Accessed Jun. 13, 2016, pp. 1-6.
WHO, World Health Organization Media Center. Obesity and overweight, Fact Sheet No. 311. Updated Jan. 2015, pp. 1-5.
Wild et al., "Global prevalence of diabetes: estimates for the year 2000 and projections for 2030." Diabetes Care 27 (5):1047-53 (May 2004).
Williams et al., "Macrovascular disease in Diabetes." In handbook of Diabetes. 2nd ed. Williams G, Pickup JC, Eds. Oxford, UK, Blackwell Science pp. 151-158 (1999).
Wohlfart et al., "Cardioprotective effects of lixisenatide in rat myocardial ischemia-reperfusion injury studies" Journal of Translational Medicine, 11(1):84, 12 pages (Mar. 2013).
Wright et al., U.K. Prospective Diabetes Study Group. "Sulfonylurea inadequacy: efficacy of addition of insulin over years in patients with type 2 diabetes in the UK. Prospective Diabetes Study (UKPDS 57)." Diabetes Care 25 (2):330-36 (Feb. 2002).
Zimmet et al., "Global and societal implications of the diabetes epidemic." Nature 414(6865):782-87 (Dec. 2001).
18th World Health Congress (Helsinki). WMA Declaration of Helsinki—Ethical Principles for Medical Research Involving Human Subjects; WMA; Jun. 1964, pp. 1-8.
Abbas T., et al., "Impairment of Synaptic Plasticity and Memory formation in GLP-1 Receptor Ko Mice: Interaction Between Type 2 Diabetes and Alzheimer's Disease," Behavioural Brain Research, 2009, vol. 205 (1), pp. 265-271.
Action to Control Cardiovascular Risk in Diabetes Study Group, "Effects of Intensive Glucose Lowering in Type 2 Diabetes," The New England Journal of Medicine, 2008, vol. 358 (24), pp. 2545-2559.
Actrapid® prescribing information, Apr. 2011, pp. 1-4.
Actrapid® summary of product characteristics, Apr. 2011, pp. 1-11.
Aderinwale O.G., et al., "Current Therapies and New Strategies for the Management of Alzheimer's Disease," American Journal of Alzheimer's Disease and Other Dementias, 2010, vol. 25 (5), pp. 414-424.
Agholme L., et al., "An in Vitro Model for Neuroscience: Differentiation of SH-SY5Y Cells into Cells with Morphological and Biochemical Characteristics of Mature Neurons," Journal of Alzheimer's Disease, 2010, vol. 20, pp. 1069-1082.
Ahualli J., "The Double Duct Sign," Radiology, 2007, vol. 244 (1), pp. 314-315.
American Diabetes Association (ADA) Committee Report—The Expert Committee on the Diagnosis and Classification of Diabetes Mellitus—Report of the Expert Committee on the Diagnosis and Classification of Diabetes Mellitus, Diabetes Care, 21(Supplement 1): S5-S19 (Jan. 1998).
American Diabetes Association, "Type 2 Diabetes in Children and Adolescents," Diabetes Care, Mar. 2000, vol. 23 (3), pp. 381-389.
Aoki K., et al., "Hydrolysis of Nonionic Surfactants," Annual Report Takeda Research Laboratory, 1968, vol. 27, pp. 172-176.
Apidra® prescribing information, Apr. 2012, pp. 1-6.
Arnolds S., et al., "Basal Insulin Glargine Vs Prandial Insulin Lispro in Type 2 Diabetes," Lancet, 2008, vol. 378 (9636), pp. 370-371.
Arnolds S., et al., "Further Improvement in Postprandial Glucose Control with Addition of Exenatide or Sitagliptin to Combination therapy with Insulin Glargine and Metformin—A Proof-of-Concept Study," Diabetes Care, 2010, vol. 33 (7), pp. 1509-1515.
Auerbach R., et al., "Angiogenesis Assays: Problems and Pitfalls," Cancer Metastasis Reviews, 2000, vol. 19 (1-2), pp. 167-172.
Bakaysa D.L., et al., "Physicochemical Basis for the Rapid Time-Action of Lysb28 Prob29-Insulin: Dissociation of a Protein-Ligand Complex," Protein science, 1996, vol. 5 (12), pp. 2521-2531.
Banks W.A., et al., "Brain Uptake of the Glucagon-Like Peptide-1 Antagonist Exendin(9-39) After intranasal Administration," The Journal of Pharmacology and Experimental Therapeutics, 2004, vol. 309 (2), pp. 469-475.
Barnett A., "Dosing of Insulin Glargine in the Treatment of Type 2 Diabetes," Clinical Therapeutics, 2007, vol. 29 (6), pp. 987-999.
Barnett a.H., et al., "Tolerability and Efficacy of Exenatide and Titrated Insulin Glargine in Adult Patients with Type 2 Diabetes Previously Uncontrolled with Metformin or a Sulfonylurea: A

(56) References Cited

OTHER PUBLICATIONS

Multinational, Randomized, Open-Label, Two-Period, Crossover Noninferiority Trial," Clinical Therapeutics, 2007, vol. 29 (11), pp. 2333-2348.
Barnett R.O., et al., "Insulin Analogues," Lancet, 1997, vol. 349 (9044), pp. 47-51.
Behar J., et al., "Functional Gallbladder and Sphincter of Oddi Disorders," Gastroenterology, 2006, vol. 130 (5), pp. 1498-1509.
Beintema J.J., et al., "Molecular Evolution of Rodent Insulins," Molecular Biology and Evolution, 1987, vol. 4 (1), pp. 10-18.
Berger M., "Towards More Physiological Insulin Therapy in the 1990s a Comment," Diabetes Research and Clinical Practice, 1989, vol. 6 (4), pp. S25-S31.
Berlie H., et al., "Glucagon-Like Peptide-1 Receptor Agonists as Add-On therapy to Basal Insulin in Patients with Type 2 Diabetes: A Systematic Review," Diabetes, Metabolic Syndrome and Obesity: Targets and Therapy, 2012, vol. 5, pp. 165-174.
Berlinsulin® H prescribing information, Apr. 2012, pp. 1-4.
Berlinsulin® H summary of product characteristics, Apr. 2012, pp. 1-11.
Bertram L., et al., "The Genetics of Alzheimer Disease: Back to the Future," Neuron, 2010, vol. 68 (2), pp. 270-281.
Best, Mathmatics and Statistics pp. 1-39, 1988.
Bhatt N.P., et al., "Chemical Pathways of Peptide Degradation. I. Deamidation of Adrenocorticotropic Hormone," Pharmaceutical Research, 1990, vol. 7 (6), pp. 593-599.
Blanchard V., et al., "Time Sequence of Maturation of Dystrophic Neurites Associated with Abeta Deposits in APP/PS1 Transgenic Mice," Experimental Neurology, 2003, vol. 184, pp. 247-263.
Bland J.M., et al., "Measurement Error," British Medical Journal, 1996, vol. 312 (7047), pp. 1654.
Bolli G.B., "The Pharmacokinetic Basis of Insulin Therapy in Diabetes Mellitus," Diabetes Research and Clinical Practice, 1989, vol. 6 (4), pp. S3-S15.
Boutajangout A., et al., "Characterisation of Cytoskeletal Abnormalities in Mice Transgenic for Wild-Type Human Tau and Familial Alzheimer's Disease Mutants of APP and Presenilin-1," Neurobiology of Disease, 2004, vol. 15 (1), pp. 47-60.
Boutajangout A., et al., "Increased Tau Phosphorylation But Absence of formation of Neurofibrillary Tangles in Mice Double Transgenic for Human Tau and Alzheimer Mutant (M146L) Presenilin-1," Neuroscience Letters, 2002, vol. 318 (1), pp. 29-33.
Brange "Galenics of Insulin" 1987, p. 35-36.
Brange J., et al., "Chemical Stability of Insulin 3. Influence of Excipients, formulation, and Ph," Acta Pharmaceutica Nordica, 1992, vol. 4 (3), pp. 149-158.
Brange J., et al., "Design of Insulin Analogues for Meal-Related therapy," Journal of Diabetes and Its Complications, 1993, vol. 7 (2), pp. 106-112.
Brange J., et al., "Insulin Structure and Stability," Pharmaceutical Biotechnology, 1993, vol. 5, pp. 315-350.
Brange J., et al., "Monomeric Insulins and their Experimental and Clinical Implications," Diabetes Care, 1990, vol. 13 (9), pp. 923-954.
Brange J., et al., "Neutral Insulin Solutions Physically Stabilized by Addition of Zn2+," Diabetic Medicine, 1986, vol. 3, pp. 532-536.
Brange J., et al., "Toward Understanding Insulin Fibrillation," Journal of Pharmaceutical Sciences, 1997, vol. 86 (5), pp. 517-525.
Brod M., et al., "Adherence Patterns in Patients with Type 2 Diabetes on Basal Insulin Analogues: Missed, Mistimed and Reduced Doses," Current Medical Research and Opinion, 2012, vol. 28 (12), pp. 1933-1946.
Brod M., et al., "Examining Correlates of Treatment Satisfaction for injectable Insulin in Type 2 Diabetes: Lessons Learned from a Clinical Trial Comparing Biphasic and Basal Analogues," Health Quality of Life Outcomes, 2007, vol. 5, pp. 1-10.
Broderick J., et al., "Guidelines for the Management of Spontaneous intracerebral Hemorrhage in Adults," Circulation, 2007, vol. 116 (16), pp. e391-e413.
Brown J.B., et al., "Slow Response to Loss of Glycemic Control in Type 2 Diabetes Mellitus," American Journal of Managed Care, 2003, vol. 9 (3), pp. 213-217.
"Buffer" Oxford Dictionary of Biochemistry and Molecular Biology, Oxford University Press, 2001, p. 83.
Burgermeister W., et al., "The Isolation of Insuin from the Pancreas," Insulin, 1975, vol. Part 2, pp. 715-727.
Burke G.T., et al., "Nature of the B10 Amino Acid Residue Requirements for High Biological Activity of Insulin," International Journal of Peptide and Protein Research, 1984, vol. 23 (4), pp. 394-401.
Buse J.B., et al., "Use of Twice-Daily Exenatide in Basal Insulin-Treated Patients with Type 2 Diabetes: A Randomized, Controlled Trial," Annals of Internal Medicine, 2011, vol. 154 (2), pp. 103-112.
Byrne M.M., et al., "Inhibitory Effects of Hyperglycaemia on Fed Jejunal Motility: Potential Role of HyperInsulinaemia," European Journal of Clinical Investigation, 1998, vol. 28 (1), pp. 72-78.
Cadario B., "SITAGLIPTIN," Drug Information Perspectives, 2010, vol. 30 (4), pp. 1-6.
Campbell R.K., et al., "Insulin Glargine," Clinical Therapeutics, 2001, vol. 23 (12), pp. 1938-1957.
Canadian Diabetes Association, Clinical Practice Guidelines Expert Committee, Canadian Diabetes Association 2008, Clinical Practice Guidelines for the Prevention and Management of Diabetes in Canada, Canadian Journal of Diabetes, 2008, pp. S162-S167.
Casas C., et al., "Massive CA1/2 Neuronal Loss with Intraneuronal and N-Terminal Truncated Abeta42 Accumulation in a Novel Alzheimer Transgenic Model," American Journal of Pathology, 2004, vol. 165 (4), pp. 1289-1300.
Centers for Disease Control and Prevention, National Diabetes Fact Sheet: General Information and National Estimates on Diabetes in the United States, 2003, Revolution Education Atlanta, GA: U.S. Department of Health and Human Services, Centers for Disease Control and Prevention, 2004, pp. 1-8.
Chancel, "Natixis Conference on Diabetes." Sanofi, Paris, pp. 1-23 (Nov. 8, 2011).
Chatterjee S., et al., "Insulin Glargine and its Place in the Treatment of Types 1 and 2 Diabetes Mellitus," Expert Opinion on Pharmacotherapy, 2006, vol. 7 (10), pp. 1357-1371.
Chen Y.E., et al., "Tissue-Specific Expression of Unique mRNAs That Encode Proglucagon-Derived Peptides or Exendin 4 in the Lizard," The Journal of Biological Chemistry, 1997, vol. 272 (7), pp. 4108-4115.
Cheung Y.T., et al., "Effects of All-Trans-Retinoic Acid on Human SH-SY5Y Neuroblastoma as in Vitro Model in Neurotoxicity Research," Neurotoxicology, 2009, vol. 30 (1), pp. 127-135.
Chi E.Y., Excipients and their Effects on the Quality of Biologics, Available online at https://www.aaps.org/uploadedFiles/Content!Sections_and_Groups/Sections/Formulation_Design_And_Development_Section/FD-DTechCornerMay2012.pdf , 9 pages (2012.
Cholangiocarcinoma, Johns Hopkins Medicine Webstite, https://gi.jhsps.org/GDLDisease.aspx?CurrentUDV=31&GDLCat_ID=AF793A59-B736-42CB-9E1FE79D2B9FC358&GDL_Disease_ID=A6D1OE80-887D-49A7-B3BB-0517D38CE757, accessed on May 14, 2014, pp. 1-12.
Cochran E., et al., "The Use of U-500 in Patients with Extreme Insulin Resistance," Diabetes Care, 2005, vol. 28 (5), pp. 1240-1244.
Colclough et al., Abstract "Levels of FPG and HbA1c Control and the Relationship to BMI in T2D Patients Treated with Basal Insulin and OAD Therapy." Abstract 2416-PO; Presented at the 72nd Scientific Session at the American Diabetes Association Meeting, 2012, A609, one page.
Colino E., et al., "Therapy with Insulin Glargine (Lantus) in toddlers, Children and Adolescents with Type 1 Diabetes," Diabetes Research and Clinical Practice, 2005, vol. 70 (1), pp. 1-7.
Correa, "Pautas para el examen de patentes farmaceuticas. Una perspectiva desde la Salud Publica. Documento de Trabajo" Universidad de Buenos Aires, Mar. 2008, see English on pp. 19-20, pp. 1-66.

(56) References Cited

OTHER PUBLICATIONS

Craig et al., "ISPAD Clinical Practice Consensus Guidelines 2014 Compendium—Definition, epidemiology, and classification of diabetes in children and adolescents." Pediatric Diabetes, 15(Suppl. 20):4-17 (2014).
Croom K.F., et al., "Liraglutide a Review of its Use in Type 2 Diabetes Mellitus," Drugs, 2009, vol. 69 (14), pp. 1985-2004.
Cvetkovic R.S., et al., "Exenatide a Review of its Use in Patients with Type 2 Diabetes Mellitus (As an Adjunct to Metformin and/or a Sulfonylurea)," Drugs, 2007, vol. 67 (6), pp. 935-954.
Czech C., et al., "Proteolytical Processing of Mutated Human Amyloid Precursor Protein in Transgenic Mice," Brain Research Molecular Brain Research, 1997, vol. 47 (1-2), pp. 108-116.
D'Alessio D.A., et al., "Glucagon-Like Peptide 1 Enhances Glucose tolerance both by Stimulation of Insulin Release and by increasing Insulin-Independent Glucose Disposal," Journal of Clinical Investigation, 1994, vol. 93 (5), pp. 2263-2266.
Database, ADISCTI, "A randomized, 4-sequence, cross-over, double bind, dose response study of 0.4, 0.6 and 0.09 U/kg insluin glarine U300 compared to 0.4 U/kg Lantus U100 in patients with diabetes mellitus type I using euglycemic clamp technique" last updated Dec. 16, 2010, pp. 1-4.
Davis How to Convert mg to mmol/L, available online at http://www.ehow.com/how_8498850_convert mg-mmoll.html (accessed on Nov. 11, 2015).
De Arriba S.G., et al., "Carbonyl Stress and Nmda Receptor Activation Contribute to Methylglyoxal Neurotoxicity," Free Radical Biology and Medicine, 2006, vol. 40 (5), pp. 779-790.
De La Pena A., et al., "Pharmacokinetics and Pharmacodynamics of High-Dose Human Regular U-500 Insulin Versus Human Regular U-100 Insulin in Healthy Obese Subjects," Diabetes Care, 2011, vol. 34 (12), pp. 2496-2501.
De Rosa R., et al., "Intranasal Administration of Nerve Growth Factor (Ngf) Rescues Recognition Memory Deficits in Ad11 Anti-Ngf Transgenic Mice," Proceedings of the National Academy of Sciences of the United States of America, 2005, vol. 102 (10), pp. 3811-3816.
Deacon C.F., et al., "Dipeptidyl Peptidase IV inhibition Potentiates the Insulinotropic Effect of Glucagon-Like Peptide 1 in the Anesthetized Pig," Diabetes, 1998, vol. 47 (5), pp. 764-769.
Deacon C.F., et al., "Dipeptidyl Peptidase IV Resistant Analogues of Glucagon-Like Peptide-1 Which have Extended Metabolic Stability and Improved Biological Activity," Diabetologia, 1998, vol. 41 (3), pp. 271-278.
Definition of indication, Merriam-Webster online, accessed Oct. 22, 2015, 2 pages.
Definition of palliative, http://medicaldictionary.thefreedictionary.com/, accessed on Nov. 6, 2014, pp. 1-2.
Definition of sphincter of pancreatic duct in the Medical Dictionary, http://medicaldictionary.thefreedictionary.com/, accessed on May 22, 2014, pp. 1-2.
Defronzo R.A., "Pharmacologic therapy for Type 2 Diabetes Mellitus," Annals of Internal Medicine, 1999, vol. 131 (4), pp. 281-303.
Delatour B., et al., "Alzheimer Pathology Disorganizes Cortico-Cortical Circuitry: Direct Evidence from a Transgenic Animal Model," Neurobiology of Disease, 2004, vol. 16 (1), pp. 41-47.
Devries J.H., et al., "Sequential intensification of Metformin Treatment in Type 2 Diabetes with Liraglutide Followed by Randomized Addition of Basal Insulin Prompted by A1C Targets," Diabetes Care, 2012, vol. 35 (7), pp. 1446-1454.
Dewitt D.E., "Case Study: Treating New on-Set Catabolic Type 2 Diabetes with Glargine and Lispro," Clinical Diabetes, 2006, vol. 24 (4), pp. 180-181.
Diabetes Prevention Program Research Group, "Reduction in the incidence of Type 2 Diabetes with Lifestyle intervention or Metformin," The New England Journal of Medicine, 2002, vol. 346 (6), pp. 393-403.
Dixon G.H., et al., "Regeneration of Insulin Activity from the Separated and inactive A and B Chains," Nature, 1960, vol. 188 (4752), pp. 721-724.
Donelli G., et al., "Plastic Biliary Stent Occlusion: Factors Involved and Possible Preventive Approaches," Clinical Medicine & Research, 2007, vol. 5 (1), pp. 53-60.
Doyle M.E. et al., "Mechanisms of Action of Glucagon-Like Peptide 1 in the Pancreas," Pharmacology & Therapeutics, 2007, vol. 113 (3), pp. 546-593.
Drucker D.J. et al., "the incretin System: Glucagon-Like Peptide-1 Receptor Agonists and Dipeptidyl Peptidase-4 inhibitors in Type 2 Diabetes," Lancet, 2006, vol. 368 (9548), pp. 1696-1705.
Drucker D.J., "Glucagon-Like Peptides," Diabetes, 1998, vol. 47 (2), pp. 159-169.
Drucker D.J., "Mini Review: The Glucagon-Like Peptides," Endocrinology, 2001, vol. 142 (2), pp. 521-527.
Drucker D.J., "The Biology of Incretin Hormones," Cell Metabolism, 2006, vol. 3 (3), pp. 153-165.
Druet C., et al., "Characterization of Insulin Secretion and Resistance in Type 2 Diabetes of Adolescents," the Journal of Clinical Endocrinology & Metabolism, Feb. 2006, vol. 91 (2), pp. 401-404 (Epub Nov. 15, 2005).
DrugBank, "Insulin glargine," available online at http://www.drugbank.ca/drugs/DB00047, 16 pages (accessed online Sep. 25, 2014).
Drury P.L., et al., "Diabetic Nephropathy," British Medical Bulletin, 1989, vol. 45 (1), pp. 127-147.
Dubois B., et al., "Revising the Definition of Alzheimer's Disease: A New Lexicon," Lancet Neurology, 2010, vol. 9 (11), pp. 1118-1127.
Dunn C.J., et al., "Insulin Glargine: An Updated Review of its Use in the Management of Diabetes Mellitus," Drugs, 2003, vol. 63 (16), pp. 1743-1778.
During M.J., et al., "Glucagon-Like Peptide-1 Receptor is involved in Learning and Neuroprotection," Nature Medicine, 2003, vol. 9 (9), pp. 1173-1179.
Eckert A., et al., "Alzheimer's Disease-Like Alterations in Peripheral Cells from Presenilin-1 Transgenic Mice," Neurobiology of Disease, 2001, vol. 8 (2), pp. 331-342.
EFC6017; Clinical Trial Eudra CT No. 2007-005884-92, accessed Apr. 24, 2015, one page.
EMA—Science Medicines Health "TOUJEO" EPAR Summary for the Public, first published Nov. 5, 2009, pp. 1-3.
EMA Press Release, "European Medicines Agency recommends suspension of Avandia, Avandamet and Avaglim" pp. 1-2 (Sep. 23, 2010).
Eng J., et al., "Isolation and Characterization of Exendin-4, An Exendin-3 Analogue, from Heloderma Suspectum Venom Further Evidence for an Exendin Receptor on Dispersed Acini from Guinea Pig Pancreas," The Journal of Biological Chemistry, 1992, vol. 267 (11), pp. 7402-7405.
English translation of Search Report for Chinese Patent Application No. 201280053404.6; dated Feb. 10, 2015, pp. 1-3.
English translation of Search Report for Chinese Patent Application No. 20140220537.9; dated Feb. 13, 2015, pp. 1-2.
English translation of the TIPO Search Report for ROC Patent Application No. 104116749, dated Feb. 22, 2016, One page.
English translation of the TIPO Search Report for ROC Patent Application No. 101131466; dated Mar. 2, 2016, one pag.
English Translation of TIPO Search Report for ROC Patent Application No. 101130936, dated Dec. 1, 2015, one page.
European Medicines Agency—Science Medicines Health, "Guideline on clinical investigation of medicinal products in the treatment of diabetes mellitus" Committee for Medicinal Products for Human Use, Jan. 20, 2010, pp. 1-19.
European Medicines Agency, "Toujeo (previously Optisulin) insulin glargine," <http: index.jsp?curl="pages/medicines/human/medicines/000309/human_med_000955.jsp &mid=WCOb01ac058001d124">, last updated Jan. 25, 2016, visited Feb. 3, 2016, pp. 1-6—screenshot of "About" tab of webpage and printouts f "About" tab of webpage with listed items collapsed and expanded.</http:>.
Ex Parte Herrmann, Appeal No. 2009-001777 U.S. Appl. No. 10/616,457 (B. Pai. Nov. 13, 2009).
Extended European Search Report for Euorpean Application No. 98 11 0889.7; dated Oct. 14, 1998, pp. 1-4.

(56) References Cited

OTHER PUBLICATIONS

Extended European Search Report for European Application No. 09 17 5876.3; dated Mar. 24, 2010, pp. 1-4.
Extended European Search Report for European Application No. 09 17 5877.1; dated Apr. 29, 2010, pp. 1-5.
Extended European Search Report for European Application No. 10 16 4368.2; dated Oct. 14, 2010, pp. 1-6.
Extended European Search Report for European Application No. 10 30 5780; dated Nov. 16, 2010, pp. 1-3.
Extended European Search Report for European Application No. 11 16 6415; dated Mar. 12, 2012, pp. 1-12.
Extended European Search Report for European Application No. 11 17 9149.7; dated Feb. 9, 2012, pp. 1-8.
Extended European Search Report for European Application No. 13 305 126; dated Apr. 11, 2013, pp. 1-7.
Extended European Search Report for European Application No. 13 305 432.0; dated Sep. 13, 2013, pp. 1-5.
Extended European Search Report for European Application No. 14 16 6877.2; dated Aug. 18, 2014, pp. 1-6.
Extended European Search Report for European Application No. 14 19 7154.9: dated Apr. 8, 2015, pp. 1-7.
Fabunmi R., et al., "Patient Characteristics, Drug Adherence Patterns, and Hypoglycemia Costs for Patients with Type 2 Diabetes Mellitus Newly initiated on Exenatide or Insulin Glargine," Current Medical Research and Opinion, 2009, vol. 25 (3), pp. 777-786.
Faivre E., et al., "Effects of Gip Analogues in Neuronal Signalling, Cell Proliferation and Learning and Memory," Regulatory Peptides, 2010, vol. 164 (1), pp. 40-41.
FDA Frequently Asked Questions about Combination Products;accessed from www.fda.gov/CombinationProducts/ AboutCombinationProducts/usm101496.1/htm, 2009 downloaded Jul. 13, 2012, pp. 1-18.
FDA Guidance for Industry, US Department of Health and Human Services, Food and Drug Administration, Center for Drug Evaluation and Research (COER), pp. 1-11, Feb. 2014.
FDA label of Apidra®, May 2014, pp. 1-35.
FDA label of Humalog®, Mar. 2013, pp. 1-27.
FDA label of Lantus®, Oct. 2013, pp. 1-44.
Feinglos M.N., et al., "Effects of Liraglutide (Nn2211), A Long-Acting GLP-1 Analogue, on Glycaemic Control and Bodyweight in Subjects with Type 2 Diabetes," Diabetic Medicine, 2005, vol. 22 (8), pp. 1016-1023.
Fieller E.C., "Symposium on Interval Estimation; Some Problems with Interval Estimation," Journal of the Royal Statistical Society, 1954, vol. 16 (2), pp. 175-185.
Final Office Action from U.S. Appl. No. 12/617,805; dated Feb. 11, 2013, pp. 1-13.
Final Office Action from U.S. Appl. No. 12/617,805; dated Jan. 12, 2012, pp. 1-14.
Final Office Action from U.S. Appl. No. 12/617,805; dated Jan. 13, 2015, pp. 1-11.
Final Office Action issued in U.S. Appl. No. 13/123,835; dated Feb. 12, 2013, pp. 1-13.
Final Office Action issued in U.S. Appl. No. 13/602,913; dated Apr. 2, 2015, pp. 1-7.
Final Office Action issued in U.S. Appl. No. 13/602,913; dated Jun. 20, 2014, pp. 1-27.
Final Office Action issued in U.S. Appl. No. 13/602,913; dated Sep. 13, 2013, pp. 1-11.
Final Office action in U.S. Appl. No. 13/382,442; dated Aug. 11, 2015, pp. 1-35.
Final Rejection in U.S. Appl. No. 13/633,496; dated Nov. 18, 2014, pp. 1-11.
Final Rejection in U.S. Appl. No. 13/633,496; dated Nov. 4, 2013, pp. 1-7.
Final Rejection in U.S. Appl. No. 13/633,563; dated Apr. 22, 2015, pp. 1-12.
Final Rejection in U.S. Appl. No. 13/633,563; dated Dec. 16, 2013, pp. 1-58.
Final Rejection issued in U.S. Appl. No. 14/172,151; dated Jul. 20, 2015, pp. 1-18.
Final Rejection issued in U.S. Appl. No. 12/617,811; dated Jan. 4, 2013, pp. 1-6.
Final Rejection issued in U.S. Appl. No. 12/617,811; dated Jul. 31, 2015, pp. 1-15.
Final Rejection issued in U.S. Appl. No. 13/110,568; dated Feb. 21, 2013, pp. 1-20.
Final Rejection issued in U.S. Appl. No. 13/310,118; dated Aug. 2, 2012, pp. 1-20.
Final Rejection issued in U.S. Appl. No. 13/382,442; daed Jul. 17, 2013, pp. 1-30.
Final Rejection issued in U.S. Appl. No. 13/382,442; dated Jun. 13, 2014, pp. 1-29.
Final Rejection issued in U.S. Appl. No. 13/382,772; dated Jun. 3, 2014, pp. 1-34.
Final Rejection issued in U.S. Appl. No. 13/382,772; dated Feb. 10, 2015, pp. 1-36.
Final Rejection issued in U.S. Appl. No. 13/467,707; dated Feb. 12, 2016, pp. 1-12.
Final Rejection issued in U.S. Appl. No. 13/509,507; dated Jul. 23, 2015, pp. 1-11.
Final Rejection issued in U.S. Appl. No. 13/509,542; dated Nov. 21, 2013, pp. 1-34.
Final Rejection issued in U.S. Appl. No. 13/509,542, dated Jan. 28, 2015, pp. 1-26.
Final Rejection issued in U.S. Appl. No. 13/595,590; dated Apr. 2, 2014, pp. 1-7.
Final Rejection issued in U.S. Appl. No. 13/595,590; dated Dec. 19, 2014, pp. 1-14.
Final Rejection issued in U.S. Appl. No. 13/692,640; dated Jan. 6, 2015, pp. 1-11.
Final Rejection issued in U.S. Appl. No. 13/692,640; dated Jun. 2, 2015, pp. 1-12.
Final Rejection issued in U.S. Appl. No. 13/700,631; dated Apr. 13, 2015, pp. 1-19.
Final Rejection issued in U.S. Appl. No. 13/700,631; dated Jun. 18, 2014, pp. 1-25.
Final Rejection issued in U.S. Appl. No. 13/509,542, dated Feb. 10, 2016, pp. 1-40.
Final-Rejection issued in U.S. Appl. No. 13/432,811; dated Feb. 10, 2016, pp. 1-9.
Fox J.D., et al., "Single Amino Acid Substitutions on the Surface of *Escherichia coli* Maltose-Binding Protein can have a Profound Impact on the Solubility of Fusion Proteins," Protein Science, 2001, vol. 10 (3), pp. 622-630.
Fransson J., et al., "Oxidation of Human Insulin-Like Growth Factor I in formulation Studies: Kinetics of Methionine Oxidation in Aqueous Solution and in Solid State," Pharmaceutical Research, 1996, vol. 13 (8), pp. 1252-1257.
Galloway J.A., et al., "New forms of Insulin," Diabetes, 1972, vol. 21 (2 Suppl), pp. 637-648.
Gandhi S., et al., "Molecular Pathogenesis of Parkinson's Disease," Human Molecular Genetics, 2005, vol. 14 (18), pp. 2749-2755.
Garg R., et al., "U-500 Insulin: Why, When and How to Use in Clinical Practice," Diabetes/Metabolism Research and Reviews, 2007, vol. 23 (4), pp. 265-268.
Garriques L.N., et al., "The Effect of Mutations on the Structure of Insulin Fibrils Studied by Fourier Transform infrared (FTIR) Spectroscopy and Electron Microscopy," Journal of Pharmaceutical Sciences, 2002, vol. 91 (12), pp. 2473-2480.
Gault V.A., et al., "GLP-1 Agonists Facilitate Hippocampal Ltp and Reverse the Impairment of LTP induced by Beta-Amyloid," European Journal of Pharmacology, 2008, vol. 587 (1-3), pp. 112-117.
Geiger R., "The Chemistry of Insulin," Chemiker Zeitung, 1976, vol. 100 (3), pp. 54-56.
Gengler S., et al., "Val(8)GLP-1 Rescues Synaptic Plasticity and Reduces Dense Core Plaques in APP/PS1 Mice," Neurobiology of Aging, 2012, vol. 33 (2), pp. 265-276.
Giugliano D., et al., "Treatment Regimens with Insulin Analogues and Haemoglobin A1C Target of <7% in Type 2 Diabetes: A Systematic Review," Diabetes Research and Clinical Practice, 2010, vol. 92 (1), pp. 1-10.

(56) References Cited

OTHER PUBLICATIONS

Goke R., et al., "Distribution of GLP-1 Binding Sites in the Rat Brain: Evidence That Exendin-4 is a Ligand of Brain GLP-1 Binding Sites," European Journal of Neuroscience, 1995, vol. 7 (11), pp. 2294-2300.

Goke R., et al., "Exendin-4 is a High Potency Agonist and Truncated Exendin-(9-39)-Amide an Antagonist at the Glucagon-Like Peptide 1-(7-36)-Amide Receptor of Insulin-Secreting Beta-Cells," The Journal of Biological Chemistry, 1993, vol. 268 (26), pp. 19650-19655.

Gough K., et al., "Assessment of Dose Proportionality: Report from the Statisticians in the Pharmaceutical Industry/ Pharmacokinetics UK Joint Working Party," Drug Information Journal, 1995, vol. 29, pp. 1039-1048.

Goykhman S., et al., "Insulin Glargine: A Review 8 Years After its introduction," Expert Opinion on Pharmacotherapy, 2009, vol. 10 (4), pp. 705-718.

Greig N.H., et al., "Once Daily Injection of Exendin-4 to Diabetic Mice Achieves Long-Term Beneficial Effects on Blood Glucose Concentrations," Diabetologia, 1999, vol. 42 (1), pp. 45-50.

Gura T., "Systems for Identifying New Drugs Are often Faulty," Science, 1997, vol. 278 (5340), pp. 1041-1042.

Gutniak M., et al., "Antidiabetogenic Effect of Glucagon-Like Peptide-1 (7-36) Amide in Normal Subjects and Patients with Diabetes Mellitus," The New England Journal of Medicine, 1992, vol. 326 (20), pp. 1316-1322.

Gygi S.P., et al, "Quantitative Analysis of Complex Protein Mixtures Using Isotope-Coded Affinity Tags," Nature Biotechnology, 1999, vol. 17 (10), pp. 994-999.

Hamilton A., et al., "Novel GLP-1 Mimetics Developed to Treat Type 2 Diabetes Promote Progenitor Cell Proliferation in the Brain," Journal of Neuroscience Research, 2011, vol. 89 (4), pp. 481-489.

Hamilton A., et al., "Receptors for the incretin Glucagon-Like Peptide-1 are Expressed on Neurons in the Central Nervous System," NeuroReport, 2009, vol. 20 (13), pp. 1161-1166.

Hanefeld M., et al., "The Postprandial State and the Risk of Atherosclerosis," Diabetic Medicine, 1997, vol. 14 (Suppl 3), pp. S6-S11.

Hanefeld M., "Normnahe Postprandiale Hyperglykamie-Eine Essenzielle Komponente Guter Diabeteskontrolle Und Pravention Kardiovaskularer Erkrankungen (Near-Normal Postprandial Hyperglycemia—An Essential Component of Good Diabetes Control and Prevention of Cardiovascular Diseases)," Paul Langerhans Lecture Diabetologie and Stoffwechsel, 2007, vol. 2, pp. 362-369.

Harkavyi A., et al., "Glucagon-Like Peptide I Receptor Stimulation Reverses Key Deficits in Distinct Rodent Models of Parkinson's Disease," Journal of Neuroinflammation, 2008, vol. 5 (19), pp. 1-9.

Harris S.B., et al., "Clinical inertia in Patients with T2Dm Requiring Insulin in Family Practice," Canadian Family Physician, 2010, vol. 56 (12), pp. e418-e424.

Hartmann H., et al., "Biological Activity of Des-(626-630)-Insulinamide and Related Analogues in Rat Hepatocyte Cultures," Diabetologia, 1989, vol. 32 (7), pp. 416-420.

Heinrich G., et al., "Pre-Proglucagon Messenger Ribonucleic Acid: Nucleotide and Encoded Amino Acid Sequences of the Rat Pancreatic Complementary Deoxyribonucleic Acid," Endocrinology, 1984, vol. 115 (6), pp. 2176-2181.

Hellstrom M., et al., "T1388 GTP-010 as a Therapetuic tool in IBS Pain Relief: Prospective, Randomized, Palebo-Controlled Study of a GLP-1 Analog," Gastroenterology, 2008, vol. 134(4), pp. A-544.

Higgins G.C., et al., "Oxidative Stress: Emerging Mitochondrial and Cellular themes and Variations in Neuronal Injury," Journal of Alzheimer's Disease, 2010, vol. 20, pp. S453-S473.

Himeno T., et al., "Beneficial Effects of Exendin-4 on Experimental Polyneuropathy in Diabetic Mice," Diabetes, 2011, vol. 60 (9), pp. 2397-2406.

Hinds K., et al., "Synthesis and Characterization of Poly(Ethylene Glycol)-Insulin Conjugates," Bioconjugate Chemistry, 2000, vol. 11 (2), pp. 195-201.

Hoe 901/2004 Study Investigators Group, "Safety and Efficacy of Insulin Glargine (Hoe 901) Versus NPH Insulin in Combination with oral Treatment in Type 2 Diabetic Patients," Diabetic Medicine, 2003, vol. 20, pp. 545-551.

Holman R.R., et al., "10-Year Follow-Up of intensive Glucose Control in Type 2 Diabetes," The New England Journal of Medicine, 2008, vol. 359 (15), pp. 1577-1589.

Holscher C., "Development of Beta-Amyloid-induced Neurodegeneration in Alzheimer's Disease and Novel Neuroprotective Strategies," Reviews in the Neurosciences, 2005, vol. 16 (3), pp. 181-212.

Holscher C., et al., "New Roles for Insulin-Like Hormones in Neuronal Signalling and Protection: New Hopes for Novel Treatments of Alzheimer's Disease?," Neurobiology of Aging, 2008, vol. 31 (9), pp. 1495-1502.

Holscher C., "Incretin Analogues that have been Developed to Treat Type 2 Diabetes Hold Promise as a Novel Treatment Strategy for Alzheimer's Disease," Recent Patents on Cns Drug Discovery, 2010, vol. 5 (2), pp. 109-117.

Holscher C., "Possible Causes of Alzheimer's Disease: Amyloid Fragments, Free Radical, and Calcium Homeostasis," Neurobiology of Disease, 1998, vol. 5 (3), pp. 129-141.

Holscher C., "The Role of GLP-1 in Neuronal Activity and Neurodegeneration," Vitamins and Hormones, 2010, vol. 84, pp. 331-354.

Holst J.J., et al., "Combining GLP-1 Receptor Agonists with Insulin: therapeutic Rationales and Clinical Findings," Diabetes, Obesity and Metabolism, 2013, vol. 15 (1), pp. 3-14.

Holst J.J., "Glucagon-Like Peptide-1, A Gastrointestinal Hormone with a Pharmaceutical Potential," Current Medicinal Chemistry, 1999, vol. 6 (11), pp. 1005-1017.

Home P.D., et al., "Insulin Treatment: A Decade of Change," British Medical Bulletin, 1989, vol. 45 (1), pp. 92-110.

http://diabetes.emedtv.com/lantus/generic-lantus.html; one page, last accessed Dec. 23, 2015.

Humalog® prescribing information, Apr. 2012, pp. 1-6.

Hunter K., et al., "Drugs Developed to Treat Diabetes, Liraglutide and Lixisenatide, Cross the Blood Brain Barrier and Enhance Neurogenesis," BMC Neuroscience, 2012, vol. 13, pp. 1-6.

IDF Clinical Guidelines Task Force, Global Guideline for Type 2 Diabetes, Brussels: International Diabetes Federation, Aug. 2005, pp. 1-82.

"Insulin Aspart Injection." Formulated Preparations: Specific Monographs. British Pharmacopoeia 3. pp. 1-3 (2012).

International Search Report by the ISA for International Application No. PCT/EP2007/005932; dated Oct. 9, 2007, pp. 1-6.

International Search Report by the ISA for International Application No. PCT/EP2009/000017; dated Jun. 22, 2009, pp. 1-7.

International Search Report by the ISA for International Application No. PCT/EP2009/063195; dated May 6, 2010.

International Search Report by the ISA for International Application No. PCT/EP2010/059436; dated Jun. 17, 2011, pp. 1-5.

International Search Report by the ISA for International Application No. PCT/EP2010/059438; dated Oct. 4, 2010, pp. 1-3.

International Search Report by the ISA for International Application No. PCT/EP2010/067250; dated Mar. 23, 2011, pp. 1-3.

International Search Report by the ISA for International Application No. PCT/EP2011/058079; dated Mar. 22, 2012, pp. 1-6.

International Search Report by the ISA for International Application No. PCT/EP2011/058764; dated Jun. 30, 2011, pp. 1-9.

International Search Report by the ISA for International Application No. PCT/EP2012/066617; dated Nov. 22, 2012, pp. 1-5.

International Search Report by the ISA for International Application No. PCT/EP2012/067144; dated Aug. 11, 2012, pp. 1-5.

International Search Report by the ISA for International Application No. PCT/EP2012/069483; dated Nov. 29, 2011, pp. 1-4.

International Search Report by the ISA for International Application No. PCT/EP2012/069485; dated Dec. 11, 2012, pp. 1-5.

International Search Report by the ISA for International Application No. PCT/EP2012/074150; dated Nov. 20, 2012, pp. 1-4.

International Search Report by the ISA for International Application No. PCT/EP2014/051976; dated Mar. 4, 2014, pp. 1-3.

(56) References Cited

OTHER PUBLICATIONS

International Search Report by the ISA for International Application No. PCT/EP2014/056498; dated Jun. 25, 2014, pp. 1-10.
International Search Report by the ISA for International Application No. PCT/EP2014/062418; dated Sep. 22, 2014, pp. 1-4.
International Search Report by the ISA for International Application No. PCT/EP2015/079285; dated Mar. 9, 2016, pp. 1-7.
Isacson R., et al., "The Glucagon-Like Peptide 1 Receptor Agonist Exendin-4 improves Reference Memory Performance and Decreases Immobility in the forced Swim Test," European Journal of Pharmacology, 2009, vol. 650 (1), pp. 249-255.
Ispad, International Diabetes Federation; "Global/IDF/ISPAD Guideline for Diabetes in Childhood and Adolescence," pp. 1-132 (2011).
Jackson R.L., et al., "Neutral Regular Insulin," Diabetes, 1972, vol. 21 (4), pp. 235-245.
Jain R.K., "Barriers to Drug Delivery in Solid Tumors," Scientific American, 1994, vol. 271 (1), pp. 58-65.
Jang J.H., et al., "Neuroprotective Effects of *Triticum aestivum* L. Against B-Amyloid-induced Cell Death and Memory Impairments," Phytotherapy Research, 2010, vol. 24 (1), pp. 76-84.
Jekel P.A., et al., "Use of Endoproteinase Lys-C from Lysobacter Enzymogenes in Protein Sequence Analysis," Analytical Biochemistry, 1983, vol. 134 (2), pp. 347-354.
Jendle J., et al., "Insulin and GLP-1 Analog Combinations in Type 2 Diabetes Mellitus: A Critical Review," Expert Opinion on Investigational Drugs, 2012, vol. 21 (10), pp. 1463-1474.
Jimenez S., et al., "Inflammatory Response in the Hippocampus of PS1M146L/App751SL Mouse Model of Alzheimer'S Disease: Age-Dependent Switch in the Microglial Phenotype from Alternative to Classic," The Journal of Neuroscience, 2008, vol. 28 (45), pp. 11650-11661.
Johnson et al., "When is a unit of insulin not a unit of insulin? Detemir dosing in type 2 diabetes" Poster, one page, 2008. http://professional.diabetes.org/ContenUPosters/2008/p8-LB.pdf.
Jones K.L., et al., "Effect of Metformin in Pediatric Patients with Type 2 Diabetes: A Randomized Controlled Trial," Diabetes Care, Jan. 2002, vol. 25 (1), pp. 89-94.
Jorgensen K.H., et al., "Five Fold Increase of Insulin Concentration Delays the Absorption of Subcutaneously Injected Human Insulin Suspensions in Pigs," Diabetes Research and Clinical Practice, 2000, vol. 50, pp. 161-167.
Kaarsholm n. C., et al., "Engineering Stability of the Insulin Monomer Fold with Application to Structure-Activity Relationships," Biochemistry, 1993, vol. 32 (40), pp. 10773-10778.
Kadima W., "Role of Metal Ions in the T- to R-Allosteric Transition in the Insulin Hexamer," Biochemistry, 1999, vol. 38 (41), pp. 13443-13452.
Kaduszkiewicz H., et al., "Cholinesterase inhibitors for Patients with Alzheimer's Disease: Systematic Review of Randomised Clinical Trials," British Medical Journal (Clinical Research ed.), 2005, vol. 331 (7512), pp. 321-327.
Kaech S., et al., "Culturing Hippocampal Neurons," Nature Protocols, 2006, vol. 1 (5), pp. 2406-2415.
Kahn S.E., et al., "Glycemic Durability of Rosiglitazone, Metformin, or Glyburide Monotherapy," The New England Journal of Medicine, 2006, vol. 355 (23), pp. 2427-2443.
Kakhki V.R.D., et al., "Normal Values of Gallbladder Ejection Fraction Using 99m Tc-Sestamibi Scintigraphy after a Fatty Meal formula," Journal of Gastrointestinal and Liver Diseases, 2007, vol. 16 (2), pp. 157-161.
Kamisawa T., et al., "Pancreatographic investigation of Pancreatic Duct System and Pancreaticobiliary Malformation," Journal of Anatomy, 2008, vol. 212 (2), pp. 125-134.
Kang S., et al., "Subcutaneous Insulin Absorption Explained by Insulin'S Physicochemical Properties Evidence from Absorption Studies of Soluble Human Insulin and Insulin Analogues in Humans," Diabetes Care, 1991, vol. 14 (11), pp. 942-948.
Kao C.H., et al., "The Evaluation of Gallbladder Function by Quantitative Radionuclide Cholescintigraphy in Patients with Noninsulin-Dependent Diabetes Mellitus," Nuclear Medicine Communications, 1993, vol. 14 (10), pp. 868-872.
Kastin A.J., et al., "Entry of Exedin-4 into Brain Is Rapid but may be Limited at High Doses International Journal of Obesity and Related Metabolic Disorders," Journal of the International Association for the Study of Obesity, 2003, vol. 27 (3), pp. 313-318.
Kastin A.J., et al., "Interactions of Glucagon-Like Peptide-1 (GLP-1) with the Blood-Brain Barrier," Journal of Molecular Neuroscience, 2001, vol. 18 (1-2), pp. 7-14.
Kemmler W., et al., "Studies on the Conversion of ProInsulin to Insulin," The Journal of Biological Chemistry, 1971, vol. 246 (22), pp. 6786-6791.
Kielgast U., et al., "Treatment of Type 1 Diabetic Patients with Glucagon-Like Peptide-1 (GLP-1) and GLP-1R Agonists," Current Diabetes Reviews, 2009, vol. 5 (4), pp. 266-275.
Kim S., et al., "Exendin-4 Protects Dopaminergic Neurons by Inhibition of Microglial Activation and Matrix Metalloproteinase-3 Expression in an Animal Model of Parkinson's Disease," Journal of Endocrinology, 2009, vol. 202 (3), pp. 431-439.
Knee T.S., et al., "A Novel Use of U-500 Insulin for Continuous Subcutaneous Insulin infusion in Patients with Insulin Resistance: A Case Series," Endocrine Practice, 2003, vol. 9 (3), pp. 181-186.
Knudsen L.B., et al., "Potent Derivatives of Glucagon-Like Peptide-1 with Pharmacokinetic Properties Suitable for once Daily Administration," Journal of Medicinal Chemistry, 2000, vol. 43 (9), pp. 1664-1669.
Kohn W.D., et al., "Pi-Shifted Insulin Analogs with Extended in Vivo Time Action and Favorable Receptor Selectivity," Peptides, 2007, vol. 28 (4), pp. 935-948.
Kohner E.M., "Diabetic Retinopathy," British Medical Bulletin, 1989, vol. 45 (1), pp. 148-173.
Kolterman O.G., et al., "Synthetic Exendin-4 (Exenatide) Significantly Reduces Postprandial and Fasting Plasma Glucose in Subjects with Type 2 Diabetes," The Journal of Clinical Endocrinology & Metabolism, 2003, vol. 88 (7), pp. 3082-3089.
Korczyn A.D., et al, "Emerging therapies in the Pharmacological Treatment of Parkinson's Disease," Drugs, 2002, vol. 62 (5), pp. 775-786.
Krishnamurthy G.T., et al., "Constancy and Variability of Gallbladder Ejection Fraction: Impact on Diagnosis and therapy," Journal of Nuclear Medicine, 2004, vol. 45 (11), pp. 1872-1877.
Lando, "The New 'Designer' Insulins", Clinical Diabetes, 18(4): Fall 2000 (http://journal.diabetes.org/clinical diabelesN18N42000/pg154.hlm; accessed Oct. 22, 2013, pp. 1-13).
Langston J.W., et al., "Chronic Parkinsonism in Humans due to a Product of Meperedine-Analog Synthesis," Science, 1983, vol. 219 (4587), pp. 979-980.
Langui D., et al., "Subcellular Topography of Neuronal Aβ Peptide in APPxPS1 Transgenic Mice," The American Journal of Pathology, 2004, vol. 165 (5), pp. 1465-1477.
Lantus® ANNEX I—Summary of product characteristics. Date of first authorisation: Jun. 9, 2000, pp. 1-164.
Lantus® prescribing information, May 2012, pp. 1-6.
Lantus® Product Information—European Medicines Agency, first published Aug. 5, 2009, pp. 1-2.
Larsen B.D., et al., "Sequence-Assisted Peptide Synthesis (SAPS)," Journal of Peptide Research, 1998, vol. 52 (6), pp. 470-476.
Larsen P.J., et al., "Combination of the Insulin Sensitizer, Pioglitazone, and the Long-Acting Glp-1 Human Analog, Liraglutide, Exerts Potent Synergistic Glucose-Lowering Efficacy in Severely Diabetic ZDF Rats," Diabetes, Obesity and Metabolism, 2008, vol. 10, pp. 301-311.
Laursen K., et al., "Enhanced Monitoring of Biopharmaceutical Product Purity Using Liquid Chromatography-Mass Spectrometry," Journal of Chromatography A, 2011, vol. 1218 (28), pp. 4340-4348.
Lee C.H., et al., "Ischemia-Induced Changes in Glucagon-Like Peptide-1 Receptor and Neuroprotective Effect of its Agonist, Exendin-4, in Experimental Transient Cerebral Ischemia," Journal of Neuroscience Research, 2011, vol. 89 (7), pp. 1103-1113.
Leib R.D., et al., "Direct Quantitation of Peptide Mixtures without Standards Using Clusters formed by Electrospray Ionization Mass Spectrometry," Analytical Chemistry, 2009, vol. 81 (10), pp. 3965-3972.

(56) References Cited

OTHER PUBLICATIONS

Lens J., "The Terminal Carboxyl Groups of Insulin," Biochimica et Biophysica Acta, 1949, vol. 3, pp. 367-370.
Levemir® prescribing information, Dec. 2011, pp. 1-6.
Levene P.A., et al., "Calculation of Isoelectric Point," The Journal of Biological Chemistry, 1923, vol. 55, pp. 801-813.
Levin P., et al., "Combination therapy with Insulin Glargine and Exenatide: Real-World Outcomes in Patients with Type 2 Diabetes," Current Medical Research and Opinion, 2012, vol. 28 (3), pp. 439-446.
Levine R.L., et al., "Oxidation of Methionine in Proteins: Roles in Antioxidant Defense and Cellular Regulation," IUBMB life, 2000, vol. 50 (4-5), pp. 301-307.
Leyer S., et al., "The Role of the C-Terminus of the Insulin B-Chain in Modulating Structural and Functional Properties of the Hormone," International Journal of Peptide and Protein Research, 1995, vol. 46 (5), pp. 397-407.
Li H., et al., "Chronic Treatment of Exendin-4 Affects Cell Proliferation and Neuroblast Differentiation in the Adult Mouse Hippocampal Dentate Gyrus," Neuroscience letters, 2010, vol. 19, pp. 1205-1219.
Li L., et al., "Common Pathological Processes in Alzheimer Disease and Type 2 Diabetes: A Review," Brain Research Reviews, 2007, vol. 56, pp. 384-402.
Li Y., et al., "Enhancing the GLP-1 Receptor Signaling Pathway Leads to Proliferation and Neuroprotection in Human Neuroblastoma Cells," Journal of Neurochemistry, 2010, vol. 113 (6), pp. 1621-1631.
Li Y., et al., "GLP-1 Receptor Stimulation Preserves Primary Cortical and Dopaminergic Neurons in Cellular and Rodent Models of Stroke and Parkinsonism," Proceedings of the National Academy of Sciences of the United States of America, 2009, vol. 106 (4), pp. 1285-1290.
Li Y., et al., "GLP-1 Receptor Stimulation Reduces Amyloid-Beta Peptide Accumulation and Cytotoxicity in Cellular and Animal Models of Alzheimer's Disease," Journal of Alzheimer's Disease, 2010, vol. 19 (4), pp. 1205-1219.
Lill N., "Production of Fast-Acting Insulins and Delayed-Release Insulins—How can this Problem be Solved by Technology? Insulin formulations," Pharmazie in Unserer Zeit, 2001, vol. 30 (1), pp. 56-61.
Insuman® Comb25 prescribing information, Feb. 2011, pp. 1-4.
Insuman® Infusat prescribing information, Feb. 2011, pp. 1-4.
Lopez-Delgado M.I., et al., "Effects of Glucagon-Like Peptide 1 on the Kinetics of Glycogen Synthase a in Hepatocytes from Normal and Diabetic Rats," Endocrinology, 1998, vol. 139 (6), pp. 2811-2817.
Lotharius J., et al., "Effect of Mutant Alpha-Synuclein on Dopamine Homeostasis in a New Human Mesencephalic Cell Line," The Journal of Biological Chemistry, 2002, vol. 277 (41), pp. 38884-38894.
Lotharius J., et al., "Progressive Degeneration of Human Mesencephalic Neuron-Derived Cells Triggered by Dopamine-Dependent Oxidative Stress is Dependent on the Mixed-Lineage Kinase Pathway," Journal of Neuroscience, 2005, vol. 25 (27), pp. 6329-6342.
Lougheed W.D., et al., "Physical Stability of Insulin Formulations," Diabetes, 1983, vol. 32 (5), pp. 424-432.
Lyxumia 10 micrograms solution for injection, Summary of Product Characteristics, updated Oct. 31, 2014, pp. 1-12.
Lyxumia® ANNEX I—Summary of product characteristics. Date of first authorisation: Feb. 1, 2013, pp. 1-92.
Lyxumia, Chemical Subgroup A10BX, Community Register of Medicinal Products for Human Use, Eurpean Commission Public Health, p. 1-2 (May 2, 2013).
Lyxumia® Product Information—European Medicines Agency, first published Mar. 14, 2013, pp. 1-2.
Mancuso M., et al., "Clinical Features and Pathogenesis of Alzheimer's Disease: involvement of Mitochondria and Mitochondrial DNA," Advances in Experimental Medicine and Biology, 2010, vol. 685, pp. 34-44.
Marbury T.C., et al., "A Pilot Study to Examine the Feasibility of Insulin Glargine in Subjects with Impaired Fasting Glucose, Impaired Glucose tolerance or New-onset Type 2 Diabetes," Experimental and Clinical Endocrinology & Diabetes, 2008, vol. 116 (5), pp. 282-288.
Margolis R.L., et al., "Diagnosis of Huntington Disease," Clinical Chemistry, 2003, vol. 49 (10), pp. 1726-1732.
Markussen J., et al., "Soluble, Prolonged-Acting Insulin Derivatives. I. Degree of Protraction and Crystallizability of Insulins Substituted in the Termini of the B-Chain," Protein Engineering, 1987, vol. 1 (3), pp. 205-213.
Markussen J., et al., "Soluble, Prolonged-Acting Insulin Derivatives II Degree of Protraction and Crystallizability of Insulins Substituted in Positions A17, B8, B13, B27 and B30," Protein Engineering, 1987, vol. 1 (3), pp. 215-223.
Markussen J., et al., "Soluble, Prolonged-Acting Insulin Derivatives. III. Degree of Protraction, Crystallizability and Chemical Stability of Insulins Substituted in Positions A21, B13, B23, B27 and B30," Protein Engineering, 1988, vol. 2 (2), pp. 157-166.
Martin B., et al., "Exendin-4 Improves Glycemic Control, Ameliorates Brain and Pancreatic Pathologies, and Extends Survival in a Mouse Model of Huntington's Disease," Diabetes, 2009, vol. 58 (2), pp. 318-328.
Martin L.J., et al., "Neurodegeneration in Excitotoxicity, Global Cerebral Ischemia, and Target Deprivation: A Perspective on the Contributions of Apoptosis and Necrosis," Brain Research Bulletin, 1998, vol. 46 (4), pp. 281-309.
Mattson M.P., "Calcium and Neurodegeneration," Aging Cell, 2007, vol. 6 (3), pp. 337-350.
McClean P.L., et al., "Glucagon-Like Peptide-1 Analogues Enhance Synaptic Plasticity in the Brain: A Link between Diabetes and Alzheimer's Disease," European Journal of Pharmacology, 2010, vol. 630 (1-3), pp. 158-162.
McClean P.L., et al., "The Diabetes Drug Liraglutide Prevents Degenerative Processes in a Mouse Model of Alzheimer's Disease," The Journal of Neuroscience, 2011, vol. 31 (17), pp. 6587-6594.
Mecklenburg R.S., et al., "Complications of Insulin Pump therapy: The Effect of Insulin Preparation," Diabetes Care, 1985, vol. 8 (4), pp. 367-370.
Meier J.J., "GLP-1 Receptor Agonists for individualized Treatment of Type 2 Diabetes Mellitus," Nature Reviews. Endocrinology, 2012, vol. 8 (12), pp. 728-742.
Merrifield B., "Solid Phase Synthesis," Science, 1986, vol. 232 (4748), pp. 341-347.
Mikhail N.E., "Is Liraglutide a Useful Addition to Diabetes therapy?," Endocrine Practice, 2010, vol. 16 (6), pp. 1028-1037.
Monnier L., et al., "The Loss of Postprandial Glycemic Control Precedes Stepwise Deterioration of Fasting with Worsening Diabetes," Diabetes Care, 2007, vol. 30 (2), pp. 263-269.
Moreno-Gonzalez I., et al., "Extracellular Amyloid-B and Cytotoxic Glial Activation Induce Significant Entorhinal Neuron Loss in Young PS1M146L/APP751SL Mice," Journal of Alzheimer's Disease, 2009, vol. 18, pp. 755-776.
Muller G., et al., "Insulin Signaling in the Yeast *Saccharomyces cerevisiae*. 1. Stimulation of Glucose Metabolism and Snf 1 Kinase by Human Insulin," Biochemistry, 1998, vol. 37 (24), pp. 8683-8695.
Muzaffar M., et al., "The Mechanism of Enhanced Insulin Amyloid Fibril formation by Naciis Better Explained by a Conformational Change Model," PLoS One, 2011, vol. 6 (11), pp. 1-11.
Nakagawa A., et al., "Receptor Gene Expression of Glucagon-Like Peptide-1, but not Glucose-Dependent Insulinotropic Polypeptide, in Rat Nodose Ganglion Cells," Autonomic Neuroscience, 2004, vol. 110, pp. 36-43.
Nathan D.M., et al., "Management of Hyperglycaemia in Type 2 Diabetes Mellitus: A Consensus Algorithm for the initiation and Adjustment of therapy. Update Regarding the Thiazolidinediones," Diabetologia, 2008, vol. 51 (1), pp. 8-11.
Nathan M.D., et al., "Insulinotropic Action of Glucagon Like Peptide-1-(7-37) in Diabetic and Nondiabetic Subjects," Diabetes Care, 1992, vol. 15 (2), pp. 270-276.

(56) References Cited

OTHER PUBLICATIONS

Nauck M.A., et al., "Effects of Subcutaneous Glucagon-Like Peptide 1 (GLP-1 [7-36 Amide]) in Patients with NIDDM," Diabetologia, 1996, vol. 39 (12), pp. 1546-1553.
Nauck M.A., et al., "Glucagon-Like Peptide 1 and its Potential in the Treatment of Non-Insulin-Dependent Diabetes Mellitus," Hormone and Metabolic Research, 1997, vol. 29 (9), pp. 411-416.
Nauck M.A., et al., "Glucagon-Like Peptide 1 (GLP-1) as a New therapeutic Approach for Type 2-Diabetes," Experimental and Clinical Endocrinology, 1997, vol. 105 (4), pp. 187-195.
NCT00713830, Clinical Trials.gov "GLP-1 Agonist in Patients with Type 2 Diabetes for Glycemic Control and Safety Evaluation, on Top of Sulfonylurea" pp. 1-3, accessed Mar. 16, 2016 (updated Jul. 13, 2008).
NCT00763815, ClinicalTrials.gov, U.S. National Institutes of Health: "GLP-1 Agonist AVE0010 in Patients With Type 2 Diabetes for Glycemic Control and Safety Evaluation on Top of Pioglitazone (GETGOAL-P)" pp. 1-8 (Jun. 27, 2011).
NCT01146678, ClinicalTrials.gov "Relative Bioavailability and Activity of Different Formulations of Insulin Glargine and Lixisenatide in Patients With Diabetes Mellitus Type 1" last updated Sep. 10, 2010, pp. 1-4.
NCT01174810, ClinicalTrials.gov "Exendin-4 as a Treatment for Parkinson's Disease—Pilot Study" accessed Aug. 8, 2011, pp. 1-5.
NCT01195454, NIH Clinical Trials, "Euglycemic clamp dose-response study comparing insulin glargine U300 with Lantus U100" last updated Dec. 13, 2010, pp. 1-4.
NCT01255163, ClinicalTrials.gov "A Clinical Trial of Exendin-4 for the Treatment of Alzheimer's Disease" accessed Aug. 8, 2011, pp. 1-7.
NCT02058147 ClinicalTrials.gov "Efficacy and Safety of Insulin Glargine/Lixisenatide Fixed Ratio Combination Compared to Insulin Glargine Alone and Lixisenatide Alone on Top Metformin in Patients With T2DM (LixLan-O)" first received by ClinicalTrials. gov on Feb. 6, 2014, pp. 1-3.
NCT02058160 ClinicalTrials.gov "Efficacy and Safety of the Insulin Glargine/Lixisenatide Fixed Ratio Combination Versus Insulin Glargine in Patients With Type 2 Diabetes (LixiLan-L)" first received by ClinicalTrials.gov on 6 Feb. 2014, pp. 1-3.
Needleman S.B., et al., "A General Method Applicable to the Search for Similarities in the Amino Acid Sequence of Two Proteins," Journal of Molecular Biology, 1970, vol. 48 (3), pp. 443-453.
Neidle, "18.2 Failure Modes in the Discovery Process" Cancer Drug Design and Discovery, Elsevier/Academic Press, pp. 427-431 (2008).
Nettleton E.J., et al., "Characterization of the Oligomeric States of Insulin in Self-Assembly and Amyloid Fibril formation by Mass Spectrometry," Biophysical Journal, 2000, vol. 79 (2), pp. 1053-1065.
Nicklas et al., "Inhibition of Nadh-Linked Oxidation in Brain Mitochondria by 1-Methyl-4-Phenyl-Pyridine, A Metabolite of the Neurotoxin, 1-Methyl-4-Phenyl-1,2,5,6-Tetrahydropyridine," Life Sciences, 1985, vol. 36, pp. 2503-2508.
Nielsen L.L., et al., "Pharmacology of Exenatide (Synthetic Exendin-4): A Potential therapeutic for Improved Glycemic Control of Type 2 Diabetes," Regulatory Peptides, 2004, vol. 117 (2), pp. 77-88.
Nilsson A., et al., "Effects of Gi vs Content of Cereal Fibre of the Evening Meal on Glucose Tolerance at a Subsequent Standardized Breakfast," European Journal of Clinical Nutrition, Jun. 2008, vol. 62 (6), pp. 712-720 (Epub May 23, 2007).
Noble S.L., et al., "Insulin Lispro: A Fast-Acting Insulin Analog," American Family Physician, 1998, vol. 57 (2), pp. 279-286.
Non-Final Office Action from U.S. Appl. No. 12/617,805; dated Jul. 24, 2014, pp. 1-12.
Non-Final Office Action from U.S. Appl. No. 12/617,805; dated May 2, 2012, pp. 1-11.
Non-Final Office Action from U.S. Appl. No. 12/617,805; dated May 10 2011, pp. 1-12.
Non-Final Office Action from U.S. Appl. No. 12/617,805; dated Sep. 15, 2015, pp. 1-12.
Non-Final Office Action issued in U.S. Appl. No. 13/123,835; dated Dec. 22, 2014, pp. 1-13.
Non-Final Office Action issued in U.S. Appl. No. 13/123,835; dated Jul. 19, 2012, pp. 1-14.
Non-Final Office Action issued in U.S. Appl. No. 13/123,835; dated May 28, 2015, pp. 1-11.
Non-Final Office Action issued in U.S. Appl. No. 13/602,913; dated Dec. 2, 2014, pp. 1-12.
Non-Final Office Action issued in U.S. Appl. No. 13/602,913; dated Jan. 13, 2014, pp. 1-53.
Non-Final Office Action issued in U.S. Appl. No. 13/602,913; dated May 17, 2013, pp. 1-7.
Non-Final Rejection in U.S. Appl. No. 13/633,496; dated Apr. 29, 2013, pp. 1-53.
Non-Final Rejection in U.S. Appl. No. 13/633,496; dated Apr. 6, 2015, pp. 1-14.
Non-Final Rejection in U.S. Appl. No. 13/633,496; dated May 22, 2014, pp. 1-11.
Non-Final Rejection in U.S. Appl. No. 13/633,563; dated Dec. 1, 2014, pp. 1-9.
Non-Final Rejection in U.S. Appl. No. 13/633,563; dated Jul. 1, 2013, pp. 1-56.
Non-Final Rejection in U.S. Appl. No. 13/633,563; dated Jun. 4, 2014, pp. 1-11.
Non-Final Rejection in U.S. Appl. No. 13/633,563; dated Oct. 6, 2015, pp. 1-12.
Non-Final Rejection issued in U.S. Appl. No. 14/172,151; dated Mar. 24, 2015, pp. 1-16.
Non-Final Rejection issued in U.S. Appl. No. 12/617,811; dated Apr. 27, 2011, pp. 1-10.
Non-Final Rejection issued in U.S. Appl. No. 12/617,811; dated Jan. 14, 2015, pp. 1-15.
Non-Final Rejection issued in U.S. Appl. No. 12/617,811; dated Jun. 21, 2012, pp. 1-7.
Non-Final Rejection issued in U.S. Appl. No. 12/617,811; dated Oct. 27, 2011, pp. 1-13.
Non-Final Rejection issued in U.S. Appl. No. 13/110,568; dated Mar. 19, 2012, pp. 1-18.
Non-Final Rejection issued in U.S. Appl. No. 13/310,118; dated Mar. 19, 2012, pp. 1-19.
Non-Final Rejection issued in U.S. Appl. No. 13/310,118; dated Mar. 29, 2013, pp. 1-21.
Non-Final Rejection issued in U.S. Appl. No. 13/310,118; dated Mar. 25, 2015, pp. 1-15.
Non-Final Rejection issued in U.S. Appl. No. 13/363,956; dated May 29, 2015, pp. 1-17.
Non-Final Rejection issued in U.S. Appl. No. 13/382,442; dated Nov. 7, 2012, pp. 1-26.
Non-Final Rejection issued in U.S. Appl. No. 13/382,442; dated Dec. 19, 2013, pp. 1-29.
Non-Final Rejection issued in U.S. Appl. No. 13/382,442; dated Feb. 5, 2015, pp. 1-31.
Non-Final Rejection issued in U.S. Appl. No. 13/382,442; dated Mar. 31, 2016, pp. 1-29.
Non-Final Rejection issued in U.S. Appl. No. 13/382,772; dated Nov. 21, 2013, pp. 1-42.
Non-Final Rejection issued in U.S. Appl. No. 13/382,772; dated Sep. 29, 2014, pp. 1-33.
Non-Final Rejection issued in U.S. Appl. No. 13/382,772; dated Sep. 14, 2015, pp. 1-42.
Non-Final Rejection issued in U.S. Appl. No. 13/467,707; dated Sep. 16, 2015, pp. 1-13.
Non-Final Rejection issued in U.S. Appl. No. 13/468,422; dated Nov. 4, 2015; pp. 1-27.
Non-Final Rejection issued in U.S. Appl. No. 13/509,507; dated Aug. 6, 2013, pp. 1-11.
Non-Final Rejection issued in U.S. Appl. No. 13/509,507; dated Sep. 19, 2014, pp. 1-9.
Non-Final Rejection issued in U.S. Appl. No. 13/509,507; dated Feb. 19, 2015, pp. 1-10.

(56) References Cited

OTHER PUBLICATIONS

Non-Final Rejection issued in U.S. Appl. No. 13/509,542; dated May 23, 2013, pp. 1-21.
Non-Final Rejection issued in U.S. Appl. No. 13/509,542; dated Apr. 2, 2014, pp. 1-20.
Non-Final Rejection issued in U.S. Appl. No. 13/509,542; dated Aug. 11, 2015, pp. 1-30.
Non-Final Rejection issued in U.S. Appl. No. 13/595,590; dated Jun. 5, 2015, pp. 1-9.
Non-Final Rejection issued in U.S. Appl. No. 13/595,590; dated Oct. 16, 2013, pp. 1-7.
Non-Final Rejection issued in U.S. Appl. No. 13/595,590; dated Sep. 5, 2014, pp. 1-10.
Non-Final Rejection issued in U.S. Appl. No. 13/661,476; dated Jun. 4, 2015, pp. 1-31.
Non-Final Rejection issued in U.S. Appl. No. 13/692,640; dated May 6, 2014, pp. 1-10.
Non-Final Rejection issued in U.S. Appl. No. 13/692,640; dated Oct. 31, 2013, pp. 1-10.
Non-Final Rejection issued in U.S. Appl. No. 13/700,631; dated Apr. 22, 2013, pp. 1-27.
Non-Final Rejection issued in U.S. Appl. No. 13/700,631; dated Dec. 17, 2015, pp. 1-18.
Non-Final Rejection issued in U.S. Appl. No. 13/700,631; dated Nov. 18, 2014, pp. 1-22.
Non-Final Rejection issued in U.S. Appl. No. 13/700,631; dated Nov. 29, 2013, pp. 1-23.
Non-Final Rejection issued in U.S. Appl. No. 14/220,562; dated Apr. 8, 2015, pp. 1-18.
Non-Final Rejection issued in U.S. Appl. No. 14/303,895; dated May 21, 2015, pp. 1-11.
Non-Final Rejection issued in U.S. Appl. No. 14/303,895; dated Sep. 9, 2015, pp. 1-12.
Non-Final Rejection issued in U.S. Appl. No. 13/382,772; dated Apr. 10, 2013, pp. 1-48.
Non-Final-Rejection issued in U.S. Appl. No. 13/432,811; dated Sep. 9, 2015, pp. 1-11.
Novolog® product information, Oct. 2009, pp. 1-4.
NovoMix® prescribing information, Feb. 2011, pp. 1-5.
NovoRapid® prescribing infonnation, Jul. 2012, pp. 1-5.
Olansky L., "Do Incretin-Based Therapies Cause Acute Pancreatitis?," Journal of Diabetes Science and Technology, Jan. 2010, vol. 4 (1), pp. 228-229.
Organization for Economic Co-Ooperation and Development; OECD Principles of Good Laboratory Practice and Compliance Monitoring (as revised in 1997); ENV/MC/CHEM (98)17:1-41 (Jan. 21, 1998).
Orskov C., "Glucagon-Like Peptide-1, A New Hormone of the Entero-insular Axis," Diabetologia, 1992, vol. 35 (8), pp. 701-711.
Ott P., et al., "Diabetes in Germany(Dig) Study a Prospective 4-Year-Follow-Up Study on the Quality of Treatment for Type 2 Diabetes in Daily Practice," Deutsche Medizinische Wochenschrift, 2009, vol. 134 (7), pp. 291-297.
Patel & Advance Collaborative Group, "Effects of a Fixed Combination of Perindopril and indapamide on Macrovascular and Microvascular Outcomes in Patients with Type 2 Diabetes Mellitus (the Advance Trial): A Randomised Controlled Trial," Lancet, 2007, vol. 370 (9590), pp. 829-840.
Patel K., et al., "Chemical Pathways of Peptide Degradation. II. Kinetics of Deamidation of an Asparaginyl Residue in a Model Hexapeptide," Pharmaceutical Research, 1990, vol. 7 (8), pp. 703-711.
Pederson R.A., et al., "Improved Glucose tolerance in Zucker Fatty Rats by oral Administration of the Dipeptidyl Peptidase IV inhibitor Isoleucine Thiazolidide," Diabetes, 1998, vol. 47 (8), pp. 1253-1258.
Perfetti R., "Combining Basal Insulin Analogs with Glucagon-Like Peptide-1 Mimetics," Diabetes Technology & Therapeutics, 2011, vol. 13 (9), pp. 873-881.

Perry T., et al., "A Novel Neurotrophic Property of Glucagon-Like Peptide 1: A Promoter of Nerve Growth Factor-Mediated Differentiation in PC12 Cells," The Journal of Pharmacology and Experimental Therapeutics, 2002, vol. 300 (3), pp. 958-966.
Perry T., et al., "Evidence of GLP-1-Mediated Neuroprotection in an Animal Model of Pyridoxine-induced Peripheral Sensory Neuropathy," Experimental Neurology, 2007, vol. 203 (2), pp. 293-301.
Perry T., et al., "Protection and Reversal of Excitotoxic Neuronal Damage by Glucagon-Like Peptide-1 and Exendin-4," The Journal of Pharmacology and Experimental Therapeutics, 2002, vol. 302 (3), pp. 881-888.
Perry T., et al., "The Glucagon-Like Peptides: A Double-Edged therapeutic Sword?," Trends in Pharmacological Sciences, 2003, vol. 24 (7), pp. 377-383.
Perry T.A., et al., "A New Alzheimer's Disease interventive Strategy: GLP-1," Current Drug Targets, 2004, vol. 5 (6), pp. 565-571.
Pillion D.J., et al., "Dodecylmaltoside-Mediated Nasal and Ocular Absorption of Lyspro-Insulin: Independence of Surfactant from Multimer Dissociation," Pharmaceutical Research, 1998, vol. 15(10), pp. 1637-1639.
Pinget M., et al., "Efficacy and safety of lixisenatide once daily versus placebo in type 2 diabetes insufficiently controlled on pioglitazone (GetGoal-P)," Diabetes,61(Supp 1):A258, Poster 1010-P (Jun. 2012).
Pinhas-Hamiel O., et al., "Clinical Presentation and Treatment of Type 2 Diabetes in Children," Pediatric Diabetes, Dec. 2007, vol. 8 (Suppl. 9), pp. 16-27.
Pi-Sunyer F.X., "The Effects of Pharmacologic Agents for Type 2 Diabetes Mellitus on Body Weight," Postgraduate Medicine, 2008, vol. 120 (2), pp. 5-17.
Pohl M., et al., "Molecular Cloning of the Heloderman and Exendin-4 cDNAs in the Lizard," The Journal of Biological Chemistry, 1998, vol. 273 (16), pp. 9778-9784.
Porter D.W., et al., "Four Weeks Administration of Liraglutide Improves Memory and Learning as Well as Glycaemic Control in Mice with High Fat Dietary-induced Obesity and Insulin Resistance," Diabetes, Obesity and Metabolism, 2010, vol. 12 (10), pp. 891-899.
Pradier L et al. "Animal Models of Alzheimer's disease." Demences (Dementias); eds. Duyckaerts C. and Pasquier F.; publisher Doin; 165-170 (Sep. 10, 2002; available Aug. 27, 2002).
Prandini N., "Methods of Measuring Gallbladder Motor Functions—the Need for Standardization: Scintigraphy," Digestive and Liver Disease, 2003, vol. 35 (Suppl 3), pp. S62-S66.
"Preferable." Merriam-Webster.com. Merriam-Webster, n.d. Web. Sep. 7, 2015. http://www.merriamwebster.com/dictionary/preferable).
Raju R.P., et al., "Optimum Palliation of inoperable Hilar Cholangiocarcinoma: Comparative Assessment of the Efficacy of Plastic and Self-Expanding Metal Stents," Digestive Diseases and Sciences, 2011, vol. 56, pp. 1557-1564.
Ramos B., et al., "Early Neuropathology of Somatostatin/NPY Gabaergic Cells in the Hippocampus of a Ps1xAPP Transgenic Model of Alzheimer's Disease," Neurobiology of Aging, 2006, vol. 27 (11), pp. 1658-1672.
Rao A.D., et al., "Is the Combination of Sulfonylureas and Metformin Associated with an increased Risk of Cardiovascular Disease or all-Cause Mortality? A Meta-Analysis of Observational Studies," Diabetes Care, 2008, vol. 31 (8), pp. 1672-1678.
Raufman J.P., "Bioactive Peptides from Lizard Venoms," Regulatory peptides, 1996, vol. 61 (1), pp. 1-18.
Request for "Type C" Meeting letter sent by Michael Lutz addressed to Mary Parks, dated Apr. 21, 2006, pp. 1-10.
Riddle M.C., et al., "Adding Once-Daily Lixisenatide for Type 2 Diabetes Inadequately Controlled by Established Basal Insulin: A 24-Week, Randomized, Placebo-Controlled Comparison (Getgoal-L)," Diabetes Care, 2013, vol. 36 (9), pp. 2489-2496.
Ritzel U., et al., "A Synthetic Glucagon-Like Peptide-1 Analog with Improved Plasma Stability," The Journal of Endocrinology, 1998, vol. 159 (1), pp. 93-102.

(56) References Cited

OTHER PUBLICATIONS

Rohrmann C.A., "Differential Diagnosis of Pancreatic and Biliary Duct Diseases," Diseases of the Abdomen and Pelvis Syllabus, 1999, pp. 170-174.
Rubino A., et al., "Delayed initiation of Subcutaneous Insulin therapy after Failure of oral Glucose-Lowering Agents in Patients with Type 2 Diabetes: A Population-Based Analysis in the UK," Diabetic Medicine, 2007, vol. 24 (12), pp. 1412-1418.
Sampson H.A., et al., "Second Symposium on the Definition and Management of Anaphylaxis: Summary Report—Second National institute of Allergy and infectious Disease/Food Allergy and Anaphylaxis Network Symposium," The Journal of Allergy and Clinical Immunology, 2006, vol. 117 (2), pp. 391-397.
Sanger F., et al., "The Amide Groups of Insulin," The Biochemical Journal, 1955, vol. 59 (3), pp. 509-518.
Sanofi's Lantus Draft Prescribing Information/Package Insert: "NDA 21-081 Draft package insert" (Sponsor revision #5) Date of submission: Apr. 20, 2000; see http://www.drugbank.ca/system/fds_labels/DB00047.pdf 1265922812; pp. 1-14.
Sanofi Press Release entitled "FDA Accepts Sanofi's New Drug Application for Basal Insulin Toujeo®," dated Jul. 8, 2014, pp. 1-2.
Sanofi Press Release "Positive Results for Investigational Compound Lyxumia (Lixisenatide) Presented at American Diabetes Association's 71st Annual Scientific Sessions," (Jun. 24, 2011), pp. 1-5.
Sanofi Press Release entitled "Sanofi Receives FDA Approval of Once-Daily Basal Insulin Toujeo®," dated Feb. 26, 2015, pp. 1-4.
Schapira A.H., "Causes of Neuronal Death in Parkinson's Disease," Advances in Neurology, 2001, vol. 86, pp. 155-162.
Schellenberger V., et al., "Attempts for Quantifying the S' Subsite Specificity of Serine Proteases, Selected Papers Presented at the 2nd International Meeting on the Molecular and Cellular Regulation of Enzyme Activity, Advances in the Biosciences, Peptides and Proteases," Recent Advances, 1987, vol. 65, pp. 159-166.
Schellenberger V., et al., "Protease-Catalyzed Kinetically Controlled Peptide Synthesis," Angewante Chemie, 1991, vol. 30 (11), pp. 1437-1449.
Schindowski K., et al., "Impact of Aging: Sporadic, and Genetic Risk Factors on Vulnerability to Apoptosis in Alzheimer's Disease," Neuromolecular Medicine, 2003, vol. 4 (3), pp. 161-178.
Schmitz C., et al., "Hippocampal Neuron Loss Exceeds Amyloid Plaque Load in a Transgenic Mouse Model of Alzheimer's Disease," The American Journal of Pathology, 2004, vol. 164 (4), pp. 1495-1502.
Schubert-Zsilavecz M., et al., "Better Blood Sugar Control in Diabetics. Insulin Glargin—A Long Acting Insulin Analogue," Pharmazie in Unserer Zeit, 2001, vol. 30 (2), pp. 125-130.
Schwartz G.J., et al., "New Equations to Estimate GFR in Children with CKD," Journal of the American Society of Nephrology, Mar. 2009, vol. 20 (3), pp. 629-637 (Epub Jan. 21, 2009).
Schwartz G.P., et al., "A Superactive Insulin: [B10-Aspartic Acid]Insulin(Human)," Proceedings of the National Academy of Sciences of the United States of America, 1987, vol. 84 (18), pp. 6408-6411.
Search Report of the Indecopi for Patent Application in Peru No. 000643-2012/DIN, dated Jul. 23, 2015, pp. 1-2.
Search Report of the Intellectual Property Corporation of Malaysia for Malaysian Patent Application No. PI 2011006204; dated Sep. 15, 2015, pp. 1-3.
Secnik Boye K., et al., "Patient-Reported Outcomes in a Trial of Exenatide and Insulin Glargine for the Treatment of Type 2 Diabetes," Health and Quality of Life Outcomes, 2006, vol. 4 (80), pp. 1-8.
Seino Y., et al., "Report of the Committee on the Classification and Diagnostic Criteria of Diabetes Mellitus," Journal of the Japan Diabetes Society, 2010, vol. 53, pp. 450-467 (In Japanese) English summary also provided.
Seino Y., et al., "Randomized, Double-Blind, Placebo-Controlled Trial of the Once-Daily GLP-1 Receptor Agonist Lixisenatide in Asian Patients with Type 2 Diabetes Insufficiently Controlled on Basal Insulin with or without a Sulfonylurea (Getgoal-L-Asia)," Diabetes, Obesity and Metabolism, 2012, vol. 14 (10), pp. 910-917.
Sherer T.B., et al., "Subcutaneous Rotenone Exposure Causes Highly Selective Dopaminergic Degeneration and A-Synuclein Aggregation," Experimental Neurology, 2003, vol. 179, pp. 9-16.
Sluzky V., et al., "Kinetics of Insulin Aggregation in Aqueous Solutions Upon Agitation in the Presence of Hydrophobic Surfaces," Proceedings of the National Academy of Sciences of the United States of America, 1991, vol. 88 (21), pp. 9377-9381.
Smolka M.B., et al., "Optimization of the Isotope-Coded Affinity Tag-Labeling Procedure for Quantitative Proteome Analysis," Analytical Biochemistry, 2001, vol. 297 (1), pp. 25-31.
Sporn M.B., et al., "Chemoprevention of Cancer," Carcinogenesis, 2000, vol. 21 (3), pp. 535-530.
Starkova N.T., "Clinical Endocrinology," Guide for physicians, Medicine, 1991, pp. 192-262.
Stolk R.P., et al., "Insulin and Cognitive Function in an Elderly Population the Rotterdam Study," Diabetes Care, 1997, vol. 20 (5), pp. 792-795.
Sundby F., "Separation and Characterization of Acid-induced Insulin Transformation Products by Paper Electrophoresis in 7 M Urea," The Journal of Biological Chemistry, 1962, vol. 237 (11), pp. 3406-3411.
Tanner C.M., et al., "Rotenone, Paraquat, and Parkinson's Disease," Environmental Health Perspectives, 2011, vol. 119 (6), pp. 866-872.
Tanner J.M., et al., "Standards from Birth to Maturity for Height, Weight, Height Velocity, and Weight Velocity: British Children, Part II," Archives of Disease in Childhood, 1996, vol. 41 (220), pp. 613-635.
Tempero M.A., "How I Treat Pancreatic Ductal Adenocarcinoma," Current Clinical Issues, Journal of Oncology Practice, 2008, vol. 4 (1), pp. 46-47.
Teramoto S., et al., "Exendin-4, a Glucagon-Like Peptide-1 Receptor Agonist, provides Neuroprotection in Mice Transient Focal Cerebral lschemia," Journal of Cerebral Blood Flow and Metabolism, 2011, vol. 31 ( 8), pp. 1696-1705.
Tessari P., et al., "Insulin in Methionine and Homocysteine Kinetics in Healthy Humans: Plasma Vs intracellular Models," American Journal of Physiology. Endocrinology and Metabolism, 2005, vol. 288 (6), pp. E1270-E1276.
Tetich M., et al., "Neuroprotective Effects of (24R)-1,24-Dihydroxycholecalciferol in Human Neuroblastoma SH-SY5Y Cell Line," The Journal of Steroid Biochemistry and Molecular Biology, 2004, vol. 89-90 (1-5), pp. 365-370.
Tews D., et al., "Enhanced Protection against Cytokine- and Fatty Acid-Induced Apoptosis in Lns-1 Beta-Cells by Combined Treatment with Insulin Glargine and the Novel GLP-1 Receptor Agonist Ave0010," Diabetes, 2007, vol. 56 (Suppl 1), pp. A72-A73.
The Expert Committee on the Diagnosis and Classification of Diabetes Mellitus. Report of the Expert Committee on the Diagnosis and Classification of Diabetes Mellitus Diabetes Care, Jan. 1998, 21:Supplement 1 S5-S19. see ADA above.
Thong K.Y., et al., "Safety, Efficacy and tolerability of Exenatide in Combination with Insulin in the Association of British Clinical Diabetologists Nationwide Exenatide Audit," Diabetes, Obesity and Metabolism, 2011, vol. 13 (8), pp. 703-710.
Thurow H., et al., "Stabilisation of Dissolved Proteins against Denaturation at Hydrophobic Interfaces," Diabetologia, 1984, vol. 27 (2), pp. 212-218.
Toth M.L., et al., "Neurite Sprouting and Synapse Deterioration in the Aging Caenorhabditis Elegans Nervous-System," The Journal of Neurbscience, 2012, vol. 32 (26), pp. 8778-8790.
Turner R.C., et al., "Glycemic Control with Diet, Sulfonylurea, Metformin, or Insulin in Patients with Type 2 Diabetes Mellitus: Progressive Requirement for Multiple therapies (UKPDS 49)," JAMA, 1999, vol. 281 (21), pp. 2005-2012.
Tyler-Cross R., et al., "Effects of Amino Acid Sequence, Buffers, and Ionic Strength on the Rate and Mechanism of Deamidation of Asparagine Residues in Small Peptides," The Journal of Biological Chemistry, 1991, vol. 266 (33), pp. 22549-22556.
UK Prospective Diabetes Study (UKPDS) Group, "Effect of intensive Blood-Glucose Control with Metformin on Complications in

(56) References Cited

OTHER PUBLICATIONS

Overweight Patients with Type 2 Diabetes (UKPDS 34)," Lancet, 1998, vol. 352 (9131), pp. 854-865.
"Suspension" Stedman's Medical Dictionary, 20th Edition, p. 1450 (Williams & Wilkins Co., Baltimore 1961).
"Suspension" Taber's Cyclopedic Medical Dictionary, 19th Edition, p. 2097 (F.A. Davis Co., Philadelphia 2001).
Uttenthal L.O., et al., "Molecular forms of Glucagon-Like Peptide-1 in Human Pancreas and Glucagonomas," The Journal of Clinical Endocrinology & Metabolism, 1985, vol. 61 (3), pp. 472-479.
Valle J., et al., "Cisplatin Plus Gemcitabine Versus Gemcitabine for Biliary Tract Cancer," The New England Journal of Medicine, 2010, vol. 362 (14), pp. 1273-1281.
Van Delden, "Pancreas-Carcinoma, CT Assessment of Resectability," Radiology Department of the Academical Medical Centre, Apr. 2006, pp. 1-12.
Varadarajan S., et al., "Review: Alzheimer's Amyloid Beta-Peptide-Associated Free Radical Oxidative Stress and Neurotoxicity," Journal of Structural Biology, 2000, vol. 130 (2-3), pp. 184-208.
Venezia V., et al., "Apoptotic Cell Death and Amyloid Precursor Protein Signaling in Neuroblastoma SH-SY5Y Cells," Annals of the New York Academy of Sciences, 2004, vol. 1030, pp. 339-347.
Victoza® ANNEX I—Summary of product characteristics. First published 2009, pp. 1-32.
Victoza Press Release, "Diabetes drugs show promise in Alzheimer's" published Jan. 17, 2011, pp. 1-2.
Victoza® Product information—European Medicines Agency, first published Aug. 7, 2009, pp. 1-2.
Volund A., et al., "In Vitro and in Vivo Potency of Insulin Analogues Designed for Clinical Use," Diabetic Medicine, 1991, vol. 8 (9), pp. 839-847.
Vora J., et al., "Incretin-Based therapy in Combination with Basal Insulin: A Promising Tactic for the Treatment of Type 2 Diabetes," Diabetes & Metabolism, 2013, vol. 39 (1), pp. 6-15.
Wafa W.S., et al., "Use of U-500 Regular Insulin in Type 2 Diabetes," Diabetes Care, 2006, vol. 29 (9), pp. 2175-2176.
Wajchenberg B.L., "Clinical Approaches to Preserve Beta-Cell Function in Diabetes," Advances in Experimental Medicine and Biology, 2010, vol. 654, pp. 515-535.
Wan Z., et al., "Enhancing the Activity of Insulin at the Receptor Interface: Crystal Structure and Photo-Cross- Linking of A8 Analogues," Biochemistry, 2004, vol. 43 (51), pp. 16119-16133.
Wang L., et al., "Real-World Outcomes of US Employees with Type 2 Diabetes Mellitus Treated with Insulin Glargine or Neutral Protamine Hagedorn Insulin: A Comparative Retrospective Database Study," BMJ Open, 2013, vol. 3 (4), pp. e002348 1-9.
Ward J.D., "Diabetic Neuropathy," British Medical Bulletin, 1989, vol. 45 (1), pp. 111-126.
Watson G.S., et al., "Insulin increases CSF Abeta42 Levels in Normal Older Adults," Neurology, 2003, vol. 60 (12), pp. 1899-1903.
Weiss M.A., et al., "Activities of Monomeric Insulin Analogs at Position A8 are Uncorrelated with their thermodynamic Stabilities," The Journal of Biological Chemistry, 2001, vol. 276 (43), pp. 40018-40024.
Werner et al., "Abstract, Insulin Glargine U-100 Has a Favourable Time-Action Profile Compared to U-40 or NPH Insulin in Healthy, Normoglycaemic Dogs", Poster 37th Annual Meeting of Endocrine Society of India, Tirupati, A.P., India, ESICON, 2007, p. 2.
Werner U., et al., "Pharmacological Profile of Lixisenatide: A New GLP-1 Receptor Agonist for the Treatment of Type 2 Diabetes," Regulatory Peptides, 2010, vol. 164 (2-3), pp. 58-64.
Weyer C., et al., "Long-Term Changes in Insulin Action and Insulin Secretion Associated with Gain, Loss, Regain and Maintenance of Body Weight," Diabetologia, 2000, vol. 43 (1), pp. 36-46.
White I.R., et al., "Randomized Clinical Trials with Added Rescue Medication: Some Approaches to their Analysis and interpretation," Statistics in medicine, 2001, vol. 20 (20), pp. 2995-3008.

Whittingham J.L., et al., "Insulin at pH 2: Structural Analysis of the Conditions Promoting Insulin Fibre formation," Journal of Molecular Biology, 2002, vol. 318 (2), pp. 479-490.
Who Rational Use of Medicines,http://www.who.int/medicines/areas/rational_use/en/downloaded Dec. 18, 2014 10:02:48 AM pp. 1-4, (2012).
Widjaja a., et al., "UKPDS 20: Plasma Leptin, Obesity, and Plasma Insulin in Type 2 Diabetic Subjects," The Journal of Clinical Endocrinology and Metabolism, 1997, vol. 82 (2), pp. 654-657.
Wirths O., et al., "Intraneuronal Abeta Accumulation Precedes Plaque formation in beta-Amyloid Precursor Protein and Presenilin-1 Double-Transgenic Mice," Neuroscience Letters, 2001, vol. 306 (1-2), pp. 116-120.
Wirths O., et al., "Intraneuronal APP/A Beta Trafficking and Plaque formation in Beta-Amyloid Precursor Protein and Presenilin-1 Transgenic Mice," Brain Pathology, 2002, vol. 12 (3), pp. 275-286.
Wirths O., et al., "Reelin in Plaques of Beta-Amyloid Precursor Protein and Presenilin-1 Double-Transgenic Mice," Neuroscience Letters, 2001, vol. 316 (3), pp. 145-148.
Wollen K.A., "Alzheimer's Disease: the Pros and Cons of Pharmaceutical, Nutritional, Botanical, and Stimulatory therapies, with a Discussion of Treatment Strategies from the Perspective of Patients and Practitioners," Alternative Medicine Review, 2010, vol. 15 (3), pp. 223-244.
World Health Organization, "Definition, Diagnosis and Classification of Diabetes Mellitus and its Complications, Part 1: Diagnosis and Classification of Diabetes Mellitus," WHO/NCD/NCS/99.2, Geneva, 1999, pp. 1-66.
Written Opinion of the ISA for International Application No. PCT/EP2011/058079, dated Mar. 22, 2012, pp. 1-8.
Xie H., et al., "Characterization of Protein Impurities and Site-Specific Modifications Using Peptide Mapping with Liquid Chromatography and Data Independent Acquisition Mass Spectrometry," Analytical Chemistry, 2009, vol. 81 (14), pp. 5699-5708.
Yoon N.M., et al., "Exenatide Added to Insulin therapy: A Retrospective Review of Clinical Practice Over Two Years in an Academic Endocrinology Outpatient Setting," Clinical Therapeutics, 2009, vol. 31 (7), pp. 1511-1523.
Yu Z.P., et al., "Effect of Zinc Sulphate and Zinc Methionine on Growth, Plasma Growth Hormone Concentration, Growth Hormone Receptor and Insulin-Like Growth Factor-I Gene Expression in Mice," Clinical and Experimental Pharmacology & Physiology, 2005, vol. 32 (4), pp. 273-278.
Zealand Pharma Company Announcement "Zealand Pharma, Additional positive results from Global Phase III program with-3-lixisenatide for type 2 diabetes", Apr. 12, 2011, pp. 1-3, URL, http://files.shareholder.com/downloads/ABEA-58QR0J/0x0x458202/3ccd84a6-5f99-451a-ada0-0a8282da3dad/ZEAL_News_2011_4_12Company_Releases.pdf.
Zealand Pharma Press Release entitled "Sanofi-Aventis finalize phase IIa clinical study with GLP-1 agonist for type 2 diabetes licensed from Zealand Pharma" dated Mar. 3, 2005, one page.
Ziemer D.C., et al., "Clinical Inertia Contributes to Poor Diabetes Control in a Primary Care Setting," The Diabetes Educator, 2005, vol. 31 (4), pp. 564-571.
Ziessman H.A., et al., "Sincalide-Stimulated Cholescintigraphy: A Multicenter Investigation to Determine Optimal Infusion Methodology and Gallbladder Ejection Fraction Normal Values," Journal of Nuclear Medicine, 2010, vol. 51 (2), pp. 277-281.
Zinman B., et al., "Efficacy and Safety of the Human Glucagon-Like Peptide-1 Analog Liraglutide in Combination with Metformin and Thiazolidinedione in Patients with Type 2 Diabetes (LEAD-4 Met+TZD)," Diabetes Care, 2009, vol. 32 (7), pp. 1224-1230.
Zinman B., "The Physiologic Replacement of Insulin an Elusive Goal," The New England Journal of Medicine, 1989, vol. 321 (6), pp. 363-370.
American Diabetes Association, "Diagnosis and Classification of Diabetes Mellitus", Diabetes Care, 37 (Supplement 1):S81-S90 (Jan. 2014).
American Diabetes Association Annual Scientific Sessions, "New Diabetes Compound AVE0010 Showed Clear Dose Response Results With Once-A-Day Injection in Phase IIb Study", published Jun. 9 2008, two pages.

(56) References Cited

OTHER PUBLICATIONS

Bell et al., "Sequence of the human insulin gene." 284(5751):26-32 (Mar. 1980).
Dombrowsky & Barrett, "Type II diabetes mellitus in children: Analysis of prevalence based on the pediatric heath information system (PHIS) database" American College of Clinical Pharmacology Annual Meeting, Bethesda, Maryland (Sep. 22-24, 2013).
GenBank: AAP20099.1 "Interferon Alpha 2B [*Homo sapiens*]" dated Apr. 30, 2003; accessed Jan. 18, 2017, one page.
GenBank: AAA59149.1 "Interleukin 4 [*Homo sapiens*]" dated Jan. 6, 1995; accessed Jan. 18, 2017, one page.
GenBank: AAA52578.1 "GM-CSF [*Homo sapiens*]" dated Nov. 8, 1994; accessed Jan. 18, 2017, one page.
Giacometti et al., "In vitro activity of the histatin derivative P-113 against multidrug-resistant pathogens responsible for pneumonia in immunocompromised patients." 49(3):1249-52 (Mar. 2005).
Glucophage XR, Product Information, Bristol-Meyers Squibb Company (Jan. 2009).
Hollander & Kushner, "Type 2 Diabetes Comorbidities and Treatment Challenges: Rationale for DPP4-Inhibitors" Postgraduate Medicine, 122(3):71-80 (May 2010).
Lantus® Drug Description, downloaded Nov. 12, 2015, one page.
Miller et al., "Type 2 diabetes in the child and adolescent", In: Lifshitz F (ed) Pediatric Endocrinology: 5th edition, vol. 1, New York, Marcel Dekker, pp. 169-188 (2007).
Raman & Heptulla, "New potential adjuncts to treatment of children with type 1 diabetes mellitus" Pediatric Research, 65(4):370-74 (Apr. 2009).
Rothstein et al., "Anticandida activity is retained in P-113, a 12-amino-acid fragment of histatin 5." Antimicrob Agents Chemother. 45(5):1367-73 (May 2001).
RPMI-1640 Media Formulation, Sigma Aldrich, accessed on Jul. 10, 2016, pp. 1-5.
Sanofi, "A randomized, double- blind, placebo controlled trial to assess safety, tolerability, pharmacokinetics and pharmacodynamics of lixisentatide in pediatric (10-17 years old) and adult patients with type 2 diabetes", Sanofi, pp. 1-12 (2015). retrieved from the internet: http://en.sanofi.com/img/content/study/PKD11475_summary.pdf (retrieved on Jun. 16, 2015).
Shehadeh et al., "Can GLP-1 preparations be used in children and adolescents with diabetes mellitus?" Pediatric Endocrinology Reviews, 11(3):324-27 (Mar. 2014).
Sloop et al., "Glucagon as a target for the treatment of Type 2 diabetes." Expert Opin Ther Targets. 9(3):593-600 (Jun. 2005).
Tanner & Davies, "Clinical longitudinal standards for height and height velocity for North American children." J Pediatr. 107(3):317-29 (Sep. 1985).
Vilsboll et al., "Liraglutide, a long-acting human glucagon-like peptide-1 analog, given as monotherapy significantly improves glycemic control and lowers body weight without risk of hypoglycemia in patients with type 2 diabetes." Diabetes Care 30(6):1608-10 (Jun. 2007; Epub Mar. 19, 2007).
Werner et al., "The GLP-1 Receptor Agonist AVE0010 Abolishes OGTT-Induced Blood Glucose Excursion in Healthy, Normoglycemic Dog Without Risk of Hypoglycemia" Diabetes 56(Supplement 1):A129 (Jun. 2007). Abstract submitted.
Wolever et al., "Second-meal effect: low-glycemic-index foods eaten at dinner improve subsequent breakfast glycemic response." Am J Clin Nutr 48(4):1041-47 (Oct. 1988).
Zimmet et al., "The metabolic syndrome in children and adolescents." Lancet 369(9579)2059-61 (Jun. 2007).
Zeitler et al., "ISPAD Clinical Practice Consensus Guidelines 2014. Type 2 diabetes in the child and adolescent." Pediatr Diabetes 15(Suppl 20):26-46 (Sep. 2014).
Osterbye et al., "Sulfatide promotes the folding of proinsulin, preserves insulin crystals, and mediates its monomerization." Glycobiology 11(6):473-79 (Jun. 2001).
Final Office Action issued in U.S. Appl. No. 13/123,835; dated Nov. 18, 2015, pp. 1-16.
Final Rejection issued in U.S. Appl. No. 13/382,442; dated Sep. 21, 2016, pp. 1-32.
Non-Final Rejection issued in U.S. Appl. No. 13/509,542; dated Nov. 23, 2016, pp. 1-34.
Non-Final Rejection issued in U.S. Appl. No. 13/819,114; dated Jul. 31, 2014, pp. 1-9.
Final Rejection issued in U.S. Appl. No. 13/819,114; dated Mar. 2, 2015, pp. 1-10.
Non-Final Rejection issued in U.S. Appl. No. 13/819,114; dated Dec. 2, 2015, pp. 1-14.
Final Rejection in U.S. Application No. 13/633,496; dated Oct. 13, 2016, pp. 1-10.
International Search Report by the ISA for International Application No. PCT/EP2009/000018; dated Jun. 30, 2009, pp. 1-8.
International Search Report by the ISA for International Application No. PCT/EP2016/050804; dated Mar. 4, 2016, pp. 1-4.
Extended European Search Report for European Application No. 14 19 7685; dated Aug. 10, 2015, pp. 1-4.
Extended European Search Report for European Application No. 14 19 7685; dated Oct. 6, 2015, pp. 1-4.
Extended European Search Report for European Application No. 15 15 1488.2; dated Jul. 7, 2015, pp. 1-8.
Pinget et al., "Efficacy and safety of lixisenatide once daily versus placebo in type 2 diabetes insufficiently controlled on pioglitazone (GetGoal-P)," Diabetes, Obesity and Metabolism, 15(11):1000-1007 (Nov. 2013; Epub May 26, 2013).
Non-Final Office Action issued in U.S. Appl. No. 15/340,969; dated Jul. 24, 2017, pp. 1-6.
Non-Final Rejection issued in U.S. Appl. No. 13/382,442; dated Sep. 20, 2017, pp. 1-28.
Non-Final Office Action issued in U.S. Appl. No. 15/275,867; dated Jun. 1, 2017; pp. 1-11.
Non-Final Rejection issued in U.S. Appl. No. 13/509,507; dated Sep. 21, 2016, pp. 1-7.
Non-Final Rejection issued in U.S. Appl. No. 14/172,151; dated Jan. 19, 2017, pp. 1-20.
Final Rejection issued in U.S. Appl. No. 14/172,151; dated Jan. 4, 2016, pp. 1-20.
Non-Final Rejection issued in U.S. Appl. No. 13/467,707; dated Nov. 7, 2016, pp. 1-17.
Non-Final Rejection issued in U.S. Appl. No. 15/197,378; dated Jun. 15, 2017, pp. 1-13.
Non-Final Office Action issued in U.S. Appl. No. 15/145,255; dated Sep. 18, 2017, pp. 1-10.
Non-Final Rejection in U.S. Appl. No. 13/633,563; dated Oct. 5, 2016, pp. 1-12.
Non-Final Rejection in U.S. Appl. No. 13/633,496; dated May 25, 2017, pp. 1-10.
Non-Final Rejection issued in U.S. Appl. No. 14/303,895; dated Mar. 24, 2017, pp. 1-17.
Non-Final Rejection issued in U.S. Appl. No. 15/073,364; dated Nov. 9, 2017, pp. 1-8.
Non-Final Rejection issued in U.S. Appl. No. 14/965,586; dated Mar. 22, 2017, pp. 1-17.
Non-Final Rejection issued in U.S. Appl. No. 15/068,286; dated Apr. 11, 2017, pp. 1-12.
Extended European Search Report for European Application No. 16 19 0103.8; dated Jun. 23, 2017, pp. 1-5.
Search Report in Chinese Patent Application No. 201410818149.0; dated Jan. 10, 2017, pp. 1-3. English translation submitted.
Ahmad & Swann, and Bloomgren "Exenatide and rare adverse events." N Engl J Med 358(18):1969-72 (May 2008).
Ahren, "GLP-1 for type 2 diabetes", Experimental Cell Research, 317(9):1239-45 (Jan. 2011).
Albert-Ludwigs University Freiburg, Institute fur Medizinische Biometrie and Statistik "Non-Inferiority Trials" dated Mar. 29, 2017, one page.
American Diabetes Association, "Standards of Medical Care in Diabetes." Diabetes Care 28(Supplement 1): S4-S36 (Jan. 2005).
American Diabetes Association, "Standards of Medical Care in Diabetes—2008." Diabetes Care 31(Supplement 1): S12-S54.

(56) References Cited

OTHER PUBLICATIONS

American Diabetes Association, "Standards of Medical Care in Diabetes—2017" Diabetes Care 40(Supplement 1):S1-S142 (Jan. 2017).
Bastyr et al., "Therapy focused on lowering postprandial glucose, not fasting glucose, may be superior for lowering HbA1c. IOEZ Study Group." Diabetes Care 23(9):1236-41 (Sep. 2000).
Bennett, "Impact of the new WHO classification and diagnostic criteria." Diabetes Obes Metab 1(Supplement 2):S1-S6 (1999).
Berard et al., "Canadian Diabetes Association 2008 Clinical Practice Guidelines for the Prevention and Management of Diabetes in Canada." Canadian Journal of Diabetes 32(Supplement 1):1-215 (Sep. 2008).
Bergenstal et al., "Type 2 Diabetes- Assessing the Relative Risks and Benefits of Glucose-lowering Medications" The American Journal of Medicine 123(4):e9-e18 (Apr. 2010).
Bucceri et al., "Gallbladder and gastric emptying: relationship to cholecystokininemia in diabetics." Eur. J. Intern. Med. 13(2):123-28 (Mar. 2002).
Buse et al., "Effects of exenatide (Exendin-4) on glycemic control over 30 weeks in sulfonylurea-treated patients with type 2 diabetes." Diabetes Care 27(11):2628-35 (Nov. 2004).
BYETTA® Labeling Revision, pp. 1-24 (Jan. 11, 2008).
BYETTA® European Public Assessment Report (EPAR), pp. 1-36 (Feb. 16, 2012).
BYETTA® Prescribing Information, pp. 1-34 (Revised Oct. 2009).
BYETTA® Summary of Product Characteristics, updated Jul. 22, 2016, last accessed Jul. 31, 2017, pp. 1-13.
Charbonnel et al., "Efficacy and safety of the dipeptidyl peptidase-4 inhibitor sitagliptin added to ongoing metformin therapy in patients with type 2 diabetes inadequately controlled with metformin alone." Diabetes Care 29(12):2638-43 (Dec. 2006).
Clinical Trials Archive for Trial No. NCT00763815 updated Feb. 21, 2014. Accessed at https://clinicaltrials.gov/archive/NCT00763815/2014_02_21/changes Accessed on Nov. 13, 2017. pp. 1-13.
Coutinho et al., "The relationship between glucose and incident cardiovascular events. A metaregression analysis of published data from 20 studies of 95,783 individuals followed for 12.4 years." Diabetes Care 22(2):233-40 (Feb. 1999).
Definition of "prevent" Dictionary.com; last accessed Sep. 29, 2016, pp. 1-6.
Definition of "induce" Dictionary.com; last accessed Sep. 29, 2016, pp. 1-6.
Definition of "reduce" Dictionary.com; last accessed Aug. 13, 2017, pp. 1-4.
Degn et al., "Effect of Intravenous Infusion of Exenatide (Synthetic Exendin-4) on Glucose-Dependent Insulin Secretion and Counter-regulation During Hypoglycemia." Diabetes 53(9):2397-2403 (Sep. 2004).
de la Loge et al., "Cross-cultural development and validation of a patient self-administered questionnaire to assess duality of life in upper gastrointestinal disorders: The PAGI-QOL." Quality of Life Research 13(10):1751-62 (Dec. 2004).
Denker et al., "Exenatide (Exendin-4)-Induced Pancreatitis: A case report" Diabetes Care 29(2):471 (Feb. 2006).
De Venciana et al., "Postprandial versus preprandial blood glucose monitoring in women with gestational diabetes mellitus requiring insulin therapy." N Engl J Med 333(19):1237-41 (Nov. 1995).
Donahue et al., "Postchallenge glucose concentration and coronary heart disease in men of Japanese ancestry. Honolulu Heart Program." Diabetes 36(6):689-92 (Jun. 1987).
Eckert et al., "Assessing the progression of Parkinson's disease: A metabolic network approach," Lancet Neurol. 6(10):926-32 (Oct. 2007).
European Medicines Agency, "Guideline on clinical investigation of medicinal products in the treatment of hypertension" (EMA/238/1995 Rev 3) pp. 1-18 (Nov. 18, 2010).
European Diabetes Policy Group, "A desktop guide to Type 2 diabetes mellitus." Diabetic Medicine 16(9):716-730 (1999).

Faichney, "Metformin in Type 1 diabetes: Is This a Good or Bad Idea?" Diabetes Care 26(5):1655 (May 2003).
FDA, "Guidance of Industry—Bioequivalence studies with pharmacokinetic endpoints for drugs submitted under an ANDA" Draft Guidance by the U.S. Department of Health and Human Services, Food and Drug Administration, Center for Drug Evaluation and Research (CDER), Dec. 2013, pp. 1-24.
Forlenza et al., "Diagnosis and biomarkers of predementia in Alzheimer's disease," BMC Medicine 8:89 pp. 1-14 (Dec. 2010).
Ganz et al., "The association of body mass index with the risk of type 2 diabetes: a case—control study nested in an electronic health records system in the United States." Diabetology & Metabolic Syndrome, 6:50, pp. 1-8 (Apr. 2014).
Gerich, "Insulin glargine: long-acting basal insulin analog for improved metabolic control." Curr Med Res Opin. 20(1):31-37 (Jan. 2004).
Gillies et al, "Insulin Glargine" Drugs 59(2)L253-60 (Feb. 2000).
Godoy-Matos, "The role of glucagon on type 2 diabetes at a glance," Diabetology & Metabolic Syndrome 6:91, pp. 1-5 (Aug. 2014).
Groop et al., "Dose-dependent effects on glyburide on insulin secretion and glucose uptake in humans." Diabetes Care 14(8):724-27 (Aug. 1991).
Groop, "Sulfonylureas in NIDDM." Diabetes Care 15(6):737-54 (Jun. 1992).
Gualandi-Signorini & Giorgi, "Insulin formulations—a review" European Review for Medical and Pharmacological Sciences 5:73-83 (2001).
Halimi, "DPP-4 inhibitors and GLP-1 analogues: for whom? Which place for incretins in the management of type 2 diabetic patients?", Diabetes & Metabolism 34(Supplement 2):S91-S95 (Feb. 2008).
Heine & Dekker, "Beyond postprandial hyperglycemia: metabolic factors associated with cardiovascular disease" Diabetologia 45(4):461-75 (Apr. 2002).
Heine et al., "Exenatide versus insulin glargine in patients with suboptimally controlled type 2 diabetes." Ann Intern Med. 143(8):559-69 (Oct. 2005).
Hillier & Pedula, "Characteristics of an adult population with newly diagnosed Type 2 Diabetes. The relation of obesity and age of onset." Diabetes Care 24(9):1522-27 (Sep. 2001).
Home et al., "Management of type 2 diabetes: updated NICE guidance" BMJ 336: 1306-1308 (Jun. 2008).
Ismail-Beigi et al., "Individualizing Glycemic Targets in Type 2 Diabetes Mellitus: Implications of Recent Clinical Trials" Annals of Internal Medicine 154(8):554-559 (Apr. 2011).
Janka et al., "Comparison of basal insulin added to oral agents versus twice-daily premixed insulin as initial insulin therapy for type 2 diabetes." Diabetes Care 28(2):254-59 (Feb. 2005).
Januvia—EPAR Summary for the Public, pp. 1-3 (Aug. 2012).
Karasik et al., "Sitagliptin, a DPP-4 inhibitor for the treatment of patients with type 2 diabetes: a review of recent clinical trials," Current Medical Research and Opinion 24(2):489-96 (Jan. 2008).
Lantus® 100U/ml solution for injection (insuline glargine); published in vol. 24 No. 9 of Pract. Diab. Int. Nov./Dec. 2007, p. 472.
U.S. Appl. No. 15/144,270, filed May 2, 2016, Silvestre et al.
U.S. Appl. No. 15/197,378, filed Jun. 29, 2016, Niemöller.
U.S. Appl. No. 15/275,867, filed Sep. 26, 2016, Silvestre et al.
U.S. Appl. No. 15/595,929, filed May 15, 2017, Brunner-Schwarz et al.
U.S. Appl. No. 15/411,557, filed Jan. 20, 2017, Boka et al.
U.S. Appl. No. 15/340,969, filed Nov. 1, 2016, Werner et al.
U.S. Appl. No. 15/657,683, filed Jul. 24, 2017, Souhami of al.
U.S. Appl. No. 15/646,760, filed Jul. 11, 2017, Roy et al.
U.S. Appl. No. 15/146,255, filed May 4, 2016, Hess et al.
Lawson et al., "Coordination of gastric and gallbladder emptying after ingestion of a regular meal." Gastroenterology. 85(4):866-870 (Oct. 1983).
Lee et al., "Goals of Glycemic Control in Frail Older Patients with Diabetes" JAMA 305(13):1350-1351 (Apr. 2011).
Lepore et al., "Pharmacokinetics and pharmacodynamics of subcutaneous injection of long-acting human insulin analog glargine,

(56) References Cited

OTHER PUBLICATIONS

NPH insulin, and ultralente human insulin and continuous subcutaneous infusion of insulin lispro." Diabetes 49(12):2142-2148 (Dec. 2000).
Mac Conell et al., "Exenatide resulted in significantly greater improvements in postprandial glycaemic control compared to sitagliptin," Diabetologia 51(Supplement 1) p. S348, Abstract 872, one page (2008).
Mainous et al., "Impact of the population at risk of diabetes on projections of diabetes burden in the United States: an epidemic on the way." Diabetologia 50(5):934-940 (May 2007; Epub Nov. 21, 2006).
Matthews et al., "Homeostasis model assessment: insulin resistance and β-cell function from fasting plasma glucose and insulin concentrations in man." Diabetologia 28(7):412-419 (Jul. 1985).
Mokdad et al., "The association of body mass index with the risk of type 2 diabetes: a case—control study nested in an electronic health records system in the United States." JAMA, 289(1):76-79 (Jan. 2003).
Monnier et al., "Contribution of fasting and postprandial plasma glucose increments to the overall diurnal hyperglycemia of type 2 diabetic patients: variations with increasing levels of HbA1c." Diabetes Care 26(3):881-885 (Mar. 2003).
Mudaliar & Edelman, "Insulin therapy in type 2 diabetes." Endocrinol Metab Clin North Am. 30(4):935-982 (Dec. 2001).
Nathan et al., "Medical Management of Hyperglycemia in Type 2 Diabetes: A Consensus Algorithm for the Initiation and Adjustment of Therapy" Diabetologia 52:17-30 (2009: Epub Oct. 22, 2008).
Nathan et al., "Medical Management of Hyperglycemia in Type 2 Diabetes: A Consensus Algorithm for the Initiation and Adjustment of Therapy. A Consensus statement of the American Diabetes Association and the European Association for the Study of Diabetes." Diabetes Care 31(1):173-175 (Jan. 2008).
Nathan et al., "Translating the A1c Assay Into Estimated Average Glucose values." Diabetes Care 31(8):1473-1478 (Aug. 2008; Epub Jun. 7, 2008).
Nauck et al., "Effects of Glucagon-Like Peptide 1 on Counterregulatory Hormone Responses, Cognitive Functions, and Insulin Secretion during Hyperinsulinemic, Stepped Hypoglycemic Clamp Experiments in Healthy Volunteers." Journal of Clin. Endocrinol.& Metab. 87(3):1239-1246 (Mar. 2002).
Nauck et al., "Efficacy and safety of the dipeptidyl peptidase-4 inhibitor, sitagliptin, compared with the sulfonylurea, glipizide, in patients with type 2 diabetes inadequately controlled on metformin alone: a randomized, double-blind, non-inferiority trial," Diabetes, Obesity and Metabolism, 9(2):194-205 (Mar. 2007).
NCT00715624 Clinical Trials.gov "GLP-1 Agonist AVE0010 in Patients With Type 2 Diabetes for Glycemic Control and Safety Evaluation, on Top of Basal Insulin" (updated Mar. 2, 2011), p. 1-3.
NCT01195454, NIH Clinical Trials, "Euglycemic clamp dose-response study comparing insulin glargine U300 with Lantus U100" last updated Sep. 3, 2010, pp. 1-3.
NCT00866658 ClinicalTrials.gov, "GLP-1 agonist AVE0010 in patients with type 2 diabetes for glycemic control and safety evaluation, on top of basal insulin +/− sulfonylurea" p. 1-3, accessed Mar. 16, 2016 (updated Aug. 3, 2010).
Nice, National Institute for Health and Care Excellence, "Type 2 diabetes in adults: management" pp. 1-45 (Dec. 2, 2015).
Ohkubo et al., "Intensive insulin therapy prevents the progression of diabetic microvascular complications in Japanese patients with non-insulin-dependent diabetes mellitus: a randomized prospective 6-year study." Diabetes Res Clin Pract 28(2):103-117 (May 1995).
Profile of Lantus® (insulin glargine injection) 100 units/ml vs. NPH in patients with type 1 diabetes; https://www.lantus.com/hcp/aboutlantus/vs-nph, pp. 1-4, last accessed Feb. 19, 2016.
Riddle et al., "The treat-to-target trial: randomized addition of glargine or human NPH insulin to oral therapy of type 2 tabetes patients." Diabetes Care 26(11):3080-3086 (Nov. 2003).
Riddle, "Combined Therapy With Insulin Plus Oral Agents: Is There Any Advantage?" Diabetes Care 31(Supplement 2):S125-S130 (Feb. 2008).
Riddle, "Timely initiation of basal insulin." Am J Med 116(Suppl 3A):3S-9S (Feb. 2004).
Rodbard et al., "Statement by an American Association of Clinical Endocrinologists/American College of Endocrinology Consensus Panel on Type 2 Diabetes Mellitus: An Algorithm for Glycemic Control" Endocrine Practice 15(6):540-559 (Sep./Oct. 2009).
Rosenstock et al., "Reduced Hypoglycemia Risk with Insulin Glargine: A meta-analysis comparing insulin glargine with human NPH insulin in type 2 diabetes" Diabetes Care 28(4):950-955 (Apr. 2005).
Russell-Jones, "Current developments in the treatment of diabetes: the incretin therapies" Br J Diabetes Vasc Dis. 10:21-30 (Feb. 2010).
Sacks et al., "Guidelines and Recommendations for Laboratory Analysis in the Diagnosis and Management of Diabetes Mellitus." Clinical Chemistry 48(3):436-472 (Mar. 2002).
Sanofi-aventis Press Release, "Once Daily Lixisenatide in Combination with Basal Insulin Demonstrates Significant Improvement in Glucose Control" Paris, France (Sep. 30, 2010) pp. 1-3.
Shi, "The Newest Handbook of Clinical Drugs" Military Medical Science Press, p. 809, (Jan. 2008). English translation submitted.
Spasov & Chepurnova, "Scientific Approaches to Combination Therapy for Type 2 Diabetes Mellitus," Bulletin of Volgograd State Medical University,1(37):8-10 (2011). See English Abstract.
Stumvoll et al., "Type 2 diabetes: Principles of pathogenesis and therapy." Lancet 365(9467):1333-1346 (Apr. 2005).
Sutter Medical Foundation, "Type 2 Diabetes Adult Outpatient Insulin Guidelines" Feb. 2011, pp. 1-6.
Tang, "Biotech Drugs—Introduction and Practice Handbook" Chemical Industry Press, pp. 635-636, (Jan. 2008). English translation submitted.
UK Prospective Diabetes Study (UKPDS) Group 28: A randomized trial of efficacy of early addition of metformin in sulfonylurea-treated type 2 diabetes. Diabetes Care, 21(1):87-92 (Jan. 1998).
van Gaal et al., "Exploiting the antidiabetic properties of incretins to treat type 2 diabetes mellitus: glucagon-like peptide 1 receptor agonists or insulin for patients with inadequate glycemic control," European Journal of Endocrinology 158(6):773-784 (Jun. 2008).
van Gaal & De Leeuw, "Rationale and options for combination treatment of type 2 diabetes." Diabletologia 46 (Supplement 1):M44-M50 (Mar. 2003).
Wahlin-Boll et al., "Impaired effect of sulfonylurea following increased dosage." Eur J Clin Pharmacol 22(1):21-25 (1982).
Werner, "Preclinical pharmacology of the new GLP-1 receptor agonist AVE0010", Ann. Endocrinol. (Paris), 69(2):164-165 (Apr. 2008).
Wikipedia® entry for "Stratified sampling" Retrieved on Mar. 28, 2017, pp. 1-4.
Williams & Pickup, "Macrovascular disease in Diabetes." In handbook of Diabetes. 2nd ed. Williams G, Pickup JC, Eds. Oxford, UK, Blackwell Science Chapter 21; pp. 151-158 (1999).
Yki-Järvinen, "Combination Therapies with insulin in type 2 diabetes." Diabetes Care 24(4):758-767 (Apr. 2001).
Yki-Järvinen et al., "Comparison of Bedtime insulin regimes in patients with type 2 diabetes mellitus." Annals of Internal Medicine 130(5):389-396 (Mar. 1999).
Zinman et al., "The Effect of Adding Exenatide to a Thiazolidinedione in Suboptimally Controlled Type 2 Diabetes" Annals of Internal Medicine, 146(7):477-485 (Apr. 2007).

USE OF AVE0010 FOR THE TREATMENT OF DIABETES MELLITUS TYPE 2

CROSS-REFERENCE TO RELATED APPLICATIONS

This application is a continuation of U.S. patent application Ser. No. 13/819,114 filed on Apr. 29, 2013, which was a national stage application under 35 U.S.C. § 371 of International Application No. PCT/EP2010/062638, filed on Aug. 30, 2010, the disclosures of each of which are explicitly incorporated by reference herein.

Subject of the present invention is the use of desPro$^{36}$Exendin-4(1-39)-Lys$_6$-NH$_2$ (AVE0010, lixisenatide) or/and a pharmaceutically acceptable salt thereof, for the manufacture of a medicament for the treatment of diabetes mellitus type 2. Another subject is a pharmaceutical composition comprising desPro$^{36}$Exendin-4(1-39)-Lys$_6$-NH$_2$ or/and a pharmaceutically acceptable salt thereof, and optionally comprising pharmaceutically acceptable carriers, adjuvants, or/and auxiliary substances. Yet another aspect is a method for the treatment of diabetes mellitus type 2 comprising administering desPro$^{36}$Exendin-4(1-39)-Lys$_6$-NH$_2$ or/and a pharmaceutically acceptable salt thereof to a subject in need thereof.

In a healthy person the release of insulin by the pancreas is strictly coupled to the concentration of blood glucose. An increased level of blood glucose, as appears after meals, is rapidly counterbalanced by a respective increase in insulin secretion. In fasting condition the plasma insulin level drops to a basal value which is sufficient to ensure the continuous supply of glucose to insulin-sensitive organs and tissues and to keep the hepatic glucose production at a low level at night.

In contrast to diabetes type 1, there is not generally a lack of insulin in diabetes type 2 but in many cases, particularly in progressive cases, the treatment with insulin is regarded as the most suitable therapy, if required in combination with orally administered anti-diabetic drugs.

An increased glucose level in the blood over several years without initial symptoms represents a significant health risk. It could clearly be shown by the large-scale DCCT study in the USA (The Diabetes Control and Complications Trial Research Group (1993) N. Engl. J. Med. 329, 977-986) that chronically increased levels of blood glucose are a main reason for the development of diabetes complications. Examples for diabetes complications are micro and macro-vascular damages that possibly manifest themselves in retinopathies, nephropathies or neuropathies and lead to blindness, renal failure and the loss of extremities and are accompanied by an increased risk of cardiovascular diseases. It can thus be concluded that an improved therapy of diabetes primarily has to aim keeping blood glucose in the physiological range as closely as possible.

A particular risk exists for overweight patients suffering from diabetes type 2, e.g. patients with a body mass index (BMI)≥30. In these patients the risks of diabetes overlap with the risks of overweight, leading e.g. to an increase of cardiovascular diseases compared to diabetes type 2 patients being of a normal weight. Thus, it is particularly necessary to treat diabetes in these patients while reducing the overweight.

The compound desPro$^{36}$Exendin-4(1-39)-Lys$_6$-NH$_2$ (AVE0010, lixisenatide) is a derivative of Exendin-4. AVE0010 is disclosed as SEQ ID NO:93 in WO 01/04156:

SEQ ID NO: 1: AVE0010 (44 AS)
H-G-E-G-T-F-T-S-D-L-S-K-Q-M-E-E-E-A-V-R-L-F-I-E-
W-L-K-N-G-G-P-S-S-G-A-P-P-S-K-K-K-K-K-K-NH$_2$

SEQ ID NO: 2: Exendin-4 (39 AS)
H-G-E-G-T-F-T-S-D-L-S-K-Q-M-E-E-E-A-V-R-L-F-I-E-
W-L-K-N-G-G-P-S-S-G-A-P-P-P-S-NH$_2$ Exendins are a group of peptides which can lower blood glucose concentration. The Exendin analogue AVE0010 is characterised by C-terminal truncation of the native Exendin-4 sequence. AVE0010 comprises six C-terminal lysine residues not present in Exendin-4.

In the context of the present invention, AVE0010 includes pharmaceutically acceptable salts thereof. The person skilled in the art knows pharmaceutically acceptable salts of AVE0010. A preferred pharmaceutically acceptable salt of AVE0010 employed in the present invention is acetate.

A first aspect of the present invention is the use of desPro$^{36}$Exendin-4(1-39)-Lys$_6$-NH$_2$ or/and a pharmaceutically acceptable salt thereof, for the manufacture of a medicament for the treatment of diabetes mellitus type 2.

The subject to be treated by the medicament of the present invention suffering from diabetes type 2 may be an obese subject. In the present invention, an obese subject may have a body mass index of at least 30 kg/m$^2$.

The subject to be treated by the medicament of the present invention may be an adult subject. The subject may have an age of at least 18 years of may have an age in the range of 18 to 80 years, or 40 to 80 years, or 50 to 60 years.

The subject to be treated by the medicament of the present invention preferably does not receive an antidiabetic treatment, for instance by insulin or/and related compounds.

The subject to be treated by the medicament of the present invention may suffer from diabetes mellitus type 2 for at least 1 year or at least 2 years. In particular, in the subject to be treated, diabetes mellitus type 2 has been diagnosed at least 1 year or at least 2 years before onset of therapy by the medicament of the present invention.

The subject to be treated may have a HbA$_{1c}$ value of at least about 8% or at least about 7.5%. The subject may also have a HbA$_{1c}$ value of about 7 to about 10%. The example of the present invention demonstrates that treatment by AVE0010 results in a reduction of the HbA$_{1c}$ value in diabetes type 2 patients (see Tables 9, 10).

The active agent of the present invention is preferably used for improving glucose tolerance in the treatment of a patient suffering from diabetes type 2. Improving glucose tolerance means that the postprandial plasma glucose concentration is reduced by the active agent of the present invention. Reduction means in particular that the plasma glucose concentration reaches normoglycemic values or at least approaches these values.

In the present invention, normoglycemic values are blood glucose concentrations of in particular 60-140 mg/dl (corresponding to 3,3 bis 7.8 mM/L). This range refers in particular to blood glucose concentrations under fasting conditions and postprandial conditions.

The subject to be treated may have a fasting plasma glucose concentration of at least 8 mmol/L, at least 8.5 mmol/L or at least 9 mmol/L. These plasma glucose concentrations exceed normoglycemic concentrations. The example of the present invention demonstrates that treatment by AVE0010 results in a reduction of the blood glucose concentration in diabetes type 2 patients (see Table 15).

The subject to be treated may have a 2 hours postprandial plasma glucose concentration of at least 10 mmol/L, at least 12 mmol/L, or at least 14 mmol/L. These plasma glucose concentrations exceed normoglycemic concentrations. The example of the present invention demonstrates that treatment by AVE0010 results in a reduction of the 2 hours postprandial plasma glucose concentration in diabetes type 2 patients (see Table 11).

The subject to be treated may have a glucose excursion of at least 2 mmol/L, at least 3 mmol/L, at least 4 mmol/L or at least 5 mmol/L. In the present invention, the glucose excursion is in particular the difference of the 2 hours postprandial plasma glucose concentration and the plasma glucose concentration 30 minutes prior to a meal test. In the context of the present invention, a meal test is . . . . The example of the present invention demonstrates that treatment by AVE0010 results in a reduction of the glucose excursion in diabetes type 2 patients (see Table 12).

"Postprandial" is a term that is well known to a person skilled in the art of diabetology. The term "postprandial" describes in particular the phase after a meal or/and exposure to glucose under experimental conditions. In a healthy person this phase is characterised by an increase and subsequent decrease in blood glucose concentration. The term "postprandial" or "postprandial phase" typically ends up to 2 h after a meal or/and exposure to glucose.

A second aspect of the present invention is the use of desPro$^{36}$Exendin-4(1-39)-Lys$_6$-NH$_2$ or/and a pharmaceutically acceptable salt thereof, for the manufacture of a medicament for inducing weight loss in diabetes type 2 patients or/and for preventing weight gain in diabetes type 2 patients. The example of the present invention demonstrates that treatment by AVE0010 results in a weight reduction in diabetes type 2 patients (see Tables 13 and 14).

The active agent, the medicament or/and the pharmaceutical composition of the present invention can be used in the treatment of one or more of the medical indications described herein, for example in treatment of diabetes type 2 patients, or for conditions associated with diabetes type 2, such as reduction of the fasting plasma glucose concentration, reduction of the postprandial plasma glucose concentration, improvement of glucose tolerance, weight loss or/and prevention of weight gain.

In the present invention, desPro$^{36}$Exendin-4(1-39)-Lys$_6$-NH$_2$ may be administered to a subject in need thereof, in an amount sufficient to induce a therapeutic effect.

The compound desPro$^{36}$Exendin-4(1-39)-Lys$_6$-NH$_2$ or/and a pharmaceutically acceptable salt thereof may be administered parenterally, e.g. by injection (such as by intramuscular or by subcutaneous injection). Suitable injection devices, for instance the so-called "pens" comprising a cartridge comprising the active ingredient, and an injection needle, are known. The compound desPro$^{36}$Exendin-4(1-39)-Lys$_6$-NH$_2$ or/and a pharmaceutically acceptable salt thereof may be administered in a suitable amount, for instance in an amount in the range of 10 to 15 μg per dose or 15 to 20 μg per dose.

In the present invention, desPro$^{36}$Exendin-4(1-39)-Lys$_6$-NH$_2$ or/and a pharmaceutically acceptable salt thereof may be administered in a daily dose in the range of 10 to 20 μg, in the range of 10 to 15 μg, or in the range of 15 to 20 μg. DesPro$^{36}$Exendin-4(1-39)-Lys$_6$-NH$_2$ or/and a pharmaceutically acceptable salt thereof may be administered by one injection per day.

Yet another aspect of the present invention is a pharmaceutical composition comprising desPro$^{36}$Exendin-4(1-39)-Lys$_6$-NH$_2$ or/and a pharmaceutically acceptable salt thereof, and optionally comprising pharmaceutically acceptable carriers, adjuvants, or/and auxiliary substances.

The pharmaceutical composition of the present invention may be prepared for use in the treatment of diabetes mellitus type 2.

The pharmaceutical composition of the present invention may also be prepared for use in inducing weight loss in diabetes type 2 patients or/and for use in preventing weight gain in diabetes type 2 patients.

The pharmaceutical composition of the present invention may also be prepared for use in the treatment of a subject as described herein.

In the present invention, the pharmaceutical composition or/and the medicament described herein may be a liquid composition comprising desPro$^{36}$Exendin-4(1-39)-Lys$_6$-NH$_2$ or/and a pharmaceutically acceptable salt thereof. The skilled person knows liquid compositions of AVE0010 suitable for parenteral administration. A liquid composition of the present invention may have an acidic or a physiologic pH. An acidic pH preferably is in the range of pH 1-6.8, pH 3.5-6.8, or pH 3.5-5. A physiologic pH preferably is in the range of pH 2.5-8.5, pH 4.0-8.5, or pH 6.0-8.5. Preferably the range is of pH 4.5-5.0.

The pH may be adjusted by a pharmaceutically acceptable diluted acid (typically HCl) or pharmaceutically acceptable diluted base (typically NaOH).

The liquid composition of the present invention may comprise a suitable preservative. A suitable preservative may be selected from phenol, m-cresol, benzyl alcohol and p-hydroxybenzoic acid ester. A preferred preservative is m-cresol.

The liquid composition of the present invention may comprise a tonicity agent. A suitable tonicity agent may be selected from glycerol, lactose, sorbitol, mannitol, glucose, NaCl, calcium or magnesium containing compounds such as CaCl$_2$. The concentration of glycerol, lactose, sorbitol, mannitol and glucose may be in the range of 100-250 mM. The concentration of NaCl may be up to 150 mM. A preferred tonicity agent is glycerol.

The liquid composition of the present invention may comprise methionine.

Yet another aspect of the present invention is a method for the treatment of diabetes mellitus type 2 comprising administering desPro$^{36}$Exendin-4(1-39)-Lys$_6$-NH$_2$ or/and a pharmaceutically acceptable salt thereof to a subject in need thereof.

A further aspect of the present invention is a method for inducing weight loss in diabetes type 2 patients or/and for preventing weight gain in diabetes type 2 patients, said method comprising administering desPro$^{36}$Exendin-4(1-39)-Lys$_6$-NH$_2$ or/and a pharmaceutically acceptable salt thereof to a subject in need thereof.

In the method of the present invention, the subject may be the subject defined herein.

In the method of the present invention, the pharmaceutical composition or/and medicament as described herein may be administered.

The invention is further illustrated by the following example and figures.

FIGURE LEGENDS

FIG. 1: Study design
FIG. 2: The overall step-down testing procedure
FIG. 3: Kaplan-Meier plot of time to treatment discontinuation due to any reason—Randomized population FIG. 4: Plot of mean change in $HbA_{1c}$ (%)±SE from baseline by visit and at endpoint—mITT population. The analysis excluded measurements obtained after the introduction of rescue medication and/or after the treatment cessation plus 3 days.

Figure 5:
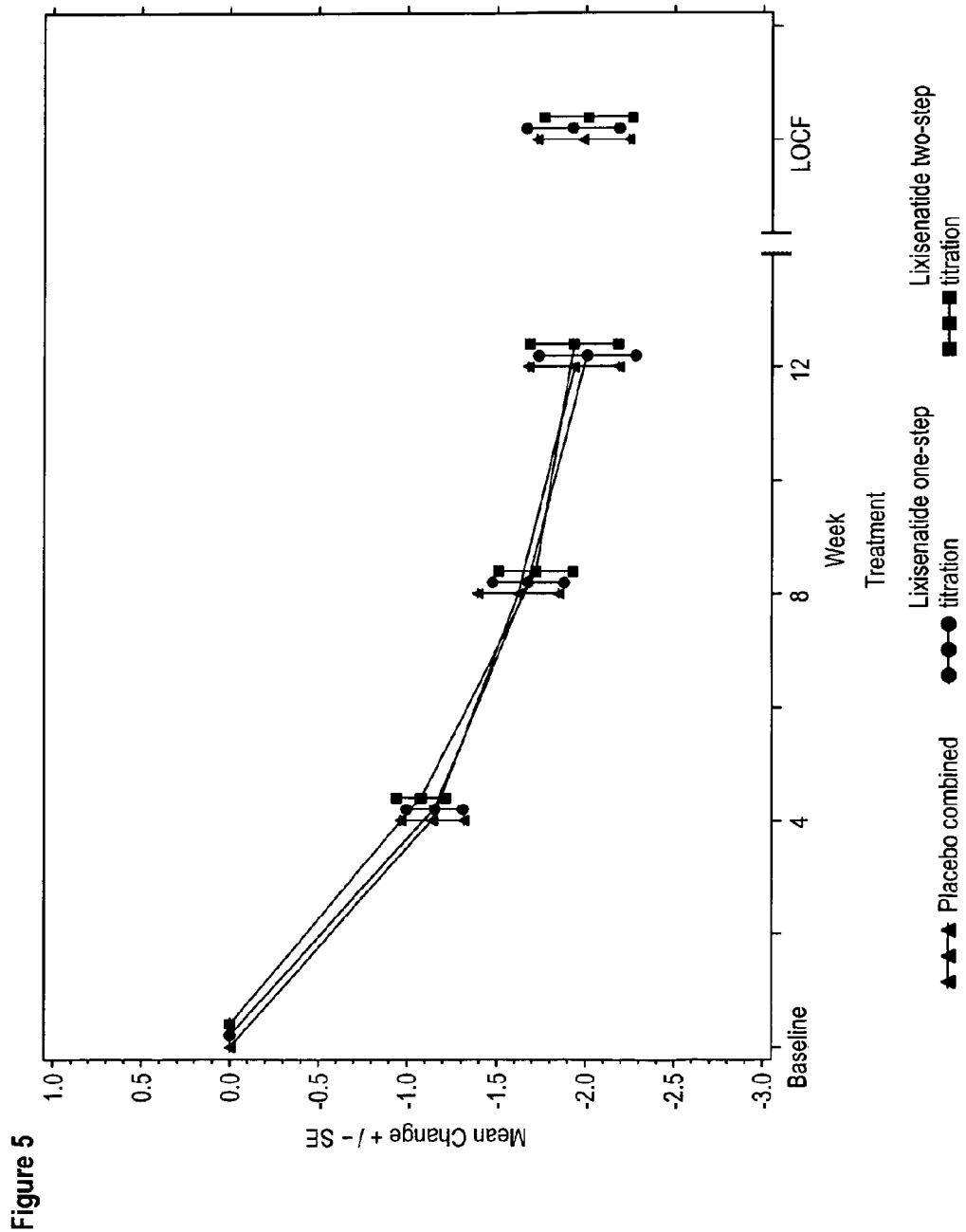

FIG. 5: Plot of mean change in body weight (kg)±SE from baseline by visit and at endpoint—mITT population. The analysis excluded measurements obtained after the introduction of rescue medication and/or after the treatment cessation plus 3 days.

Figure 6:
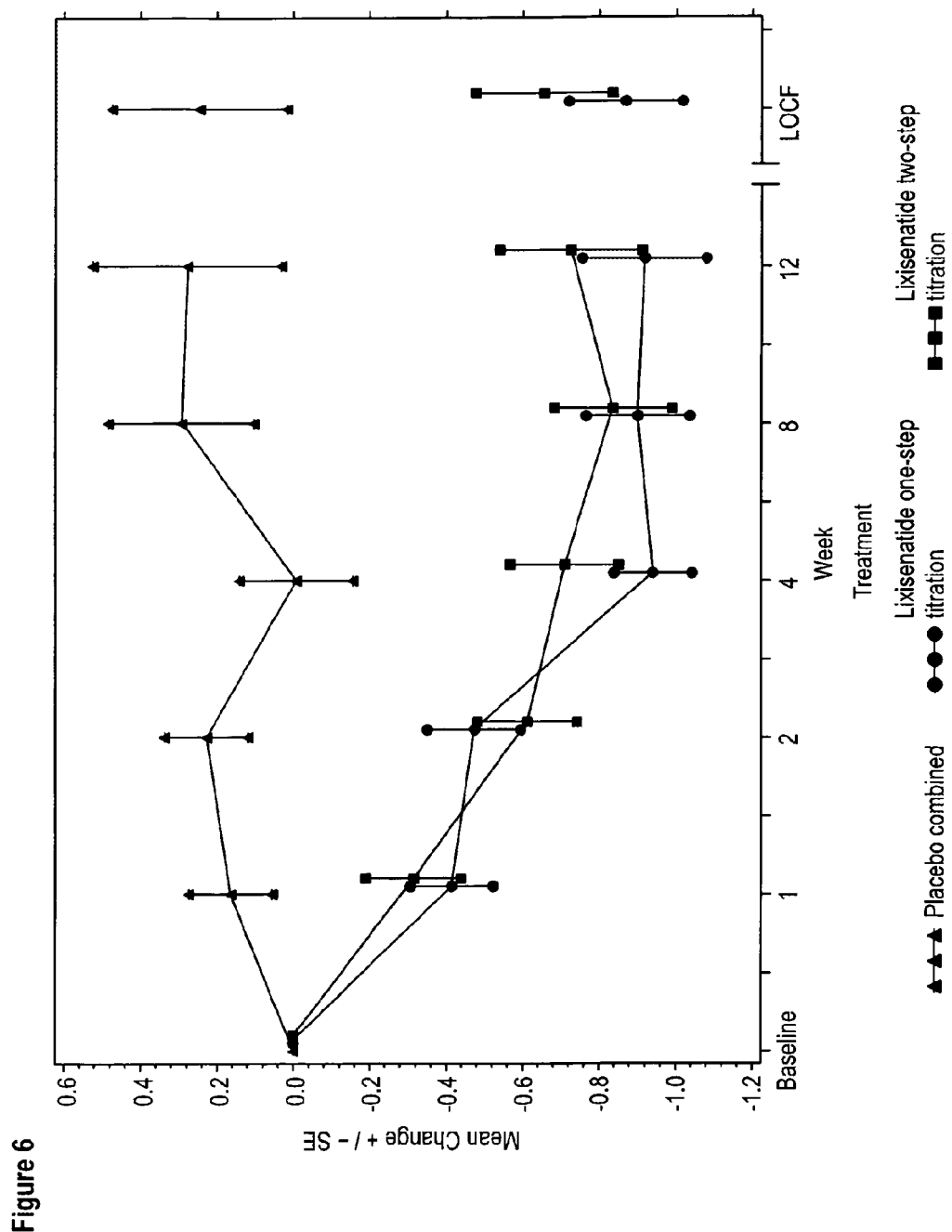

FIG. 6: Plot of mean change in fasting plasma glucose (mmol/L)±SE from baseline by visit and at endpoint—mITT population. The analysis excluded measurements obtained after the introduction of rescue medication and/or after the treatment cessation plus 1 day.

EXAMPLE

A Randomized, Double-Blind, Placebo-Controlled, Parallel-Group, Multicenter 12-Week Study Assessing the Efficacy and Safety of Lixisenatide in Patients with Type 2 Diabetes not Treated with Antidiabetic Agents

SUMMARY

Subject of the example is a randomized, double-blind, placebo-controlled, parallel-group, multicenter 12-week study assessing the efficacy and safety of lixisenatide in patients with type 2 diabetes not treated with antidiabetic agents, conducted in 61 centers of 12 countries. The primary objective of the study was to assess the effects of lixisenatide on glycemic control used in a two-step dose titration regimen in comparison to placebo in terms of $HbA_{1c}$ reduction (absolute change) over a period of 12 weeks.

A total of 361 patients were randomized to one of the four treatment groups (61 in the placebo two-step titration group, 61 in the placebo one-step titration group, 120 in the lixisenatide two-step titration group, and 119 in the lixisenatide one-step titration group). The placebo one-step and two-step titration groups were combined in analyses. Two patients were excluded from mITT population for efficacy analyses due to a lack of post-baseline efficacy data. Of 361 randomized patients, 331 (91.7%) completed the 12-week double-blind treatment. Thirty patients discontinued the treatment prematurely and 9 of these patients discontinued due to an adverse event. Demographics and baseline characteristics were generally similar across treatment groups.

The least square (LS) mean changes from baseline to endpoint in $HbA_{1c}$ were −0.19% for the placebo group, −0.73% for the lixisenatide 2-step titration group (LS mean difference vs. placebo=−0.54%; p-value=<0.0001), and −0.85% for the lixisenatide 1-step titration group (LS mean difference vs. placebo=−0.66%; p-value=<0.0001). The $HbA_{1c}$ responder analysis ($HbA_{1c} \leq 6.5$ or <7% at endpoint) using CMH method also showed a significant treatment difference versus placebo for both lixisenatide-treated groups.

For 2-hour post-prandial plasma glucose levels, each of the lixisenatide-treated groups demonstrated a significant improvement over the placebo group. The between-group difference in body weight compared to placebo was not statistically significant for either of the lixisenatide-treated groups due to a similar decrease in placebo group. Both lixisenatide-treated groups demonstrated meaningful improvements over the placebo group in fasting plasma glucose using ANCOVA analysis without multiplicity adjustment. A total of 3 lixisenatide-treated patients (2 [1.7%] in 2-step titration and 1 [0.8%] in 1-step titration) received a rescue therapy, and 3 patients [2.5%] in the placebo group.

Lixisenatide (AVE0010) was well tolerated during the 12 weeks of treatment. Incidences of TEAEs (treatment-emergent adverse events) were generally comparable across treatment groups. Only one serious TEAE was reported in a lixisenatide-treated patient (2-step titration), whereas 5 placebo-treated patients reported serious TEAEs. No death was reported in this study. A total of 8 lixisenatide-treated patients (5 [4.2%] in 2-step titration and 3 [2.5%] in 1-step titration) discontinued the treatment, mainly due to gastrointestinal (GI) disorders, while one placebo-treated patient (0.8%) discontinued. There was no obvious difference for GI tolerance in 1-step and 2-step titration lixisenatide-treated patients. The most commonly reported TEAE was nausea (24.2% for lixisenatide 2-step titration, 20.2% for lixisenatide 1-step titration and 4.1% for placebo).

A total of 6 cases (3 [2.5%] in lixisenatide 2-step titration; 1 [0.8%] in lixisenatide 1-step titration; 2 [1.6%] in placebo) of symptomatic hypoglycemia per protocol definition were observed and none of them was severe. No case of elevated lipase or amylase (≥3 ULN) was observed in any of the treatment groups.

1 Objectives
1.1 Primary Objective
The primary objective of this example was to assess the effects of lixisenatide on glycemic control used in a two-step dose titration regimen in comparison to placebo in terms of $HbA_{1c}$ reduction (absolute change) over a period of 12 weeks in patients with type 2 diabetes not treated with antidiabetic agents.

1.2 Secondary Objective(s)
The secondary objectives of this study were:
To assess the effects of lixisenatide on:
  Glycemic control in comparison to placebo in terms of $HbA_{1c}$ reduction when used in a one-step dose titration regimen over a period of 12 weeks,
  Body weight at week 12,
  Fasting plasma glucose (FPG) at week 12,
  2-hour post-prandial plasma glucose after standardized meal challenge test at week 12 in a subgroup of all the patients in selected sites (approximately 50% of the randomized patients),
To assess lixisenatide safety and tolerability over a period of 12 weeks,
To assess lixisenatide PK using population PK approach,
To assess anti-lixisenatide antibody development.

2 Trial Design
This was a double-blind, randomized, placebo-controlled, 4-arm, unbalanced design, parallel-group multinational study: two-step titration (120 lixisenatide-treated and 60 placebo-treated patients) and one-step titration (120 lixisenatide-treated and 60 placebo-treated patients). The study was double-blind with regard to active and placebo treatments. The study drug volume (i.e., dose of active drug or matching placebo) and the titration regimens (i.e., one-step and two-step) were not blinded.

The patients were stratified by screening values of glycosylated hemoglobin $A_{1c}$ ($HbA_{1c}$) (<8%, ≥8%) and body mass index (BMI<30 kg/m$^2$, ≥30 kg/m$^2$). After a screening period, patients were centrally randomized via interactive voice response system (IVRS) in a 2:1:2:1 ratio to one of the four arms (two-step titration of lixisenatide, two-step titration of placebo, one-step titration of lixisenatide, and one-step titration of placebo).

The study consisted of 3 periods: 1) an up to 3-week screening period, which included an up to 2-week screening phase and a 1-week single-blind placebo run-in phase; 2) a main 12-week double-blind, placebo-controlled treatment period; 3) a 3-day, drug-free post-treatment follow-up period.

The study design is described in FIG. 1.

The administration is performed as follows . . . .

3 Primary and Secondary Endpoints 3.1 Primary Endpoint

The primary efficacy variable was the absolute change in $HbA_{1c}$ from baseline to Week 12, which was defined as: $HbA_{1c}$ value at Week 12—$HbA_{1c}$ value at baseline.

If a patient permanently discontinued the treatment prematurely or received rescue therapy during the 12-week double-blind treatment period or did not have $HbA_{1c}$ value at Week 12, the last post-baseline on-treatment $HbA_{1c}$ measurement during the 12-week double-blind treatment period was to be used as $HbA_{1c}$ value at Week 12 (Last Observation Carry Forward [LOCF] procedure).

3.2 Secondary Endpoints

For secondary efficacy variables, the same procedure for handling missing assessments/early discontinuation during the 12-week double-blind treatment period was applied as for the primary efficacy variable.

Continuous Variables:

Change in 2-hour post-prandial plasma glucose (million) after a standardized meal test from baseline to Week 12, Change in body weight (kg) from baseline to Week 12, Change in fasting plasma glucose (mmol/L) from baseline to Week 12, Change in glucose excursion (mmol/L) (2-hour post-prandial plasma glucose—plasma glucose 30 minutes prior to the meal test, before study drug administration) after a standardized meal test from baseline to Week 12.

Categorical Variables:

Percentage of patients with $HbA_{1c}$<7% at Week 12,

Percentage of patients with $HbA_{1c}$≤6.5% at Week 12,

Percentage of patients requiring rescue therapy during the double-blind treatment period, Percentage of patients with ≥5% weight loss (kg) from baseline at Week 12.

4 Sample Size Calculation Assumptions

The sample size/power calculation was performed based on the primary efficacy variable, change from baseline to Week 12 in $HbA_{1c}$.

To detect a difference of 0.5% in the change from baseline in $HbA_{1c}$ between one lixisenatide arm and the combined placebo group at Week 12, 120 patients per group (i.e., 120 patients per lixisenatide arm and 2×60 patients for combined placebo group) provided a power of 90%. This calculation assumed a common standard deviation of 1.2% with a 2-sided test at the 5% significance level. The sample size calculations were based upon the two-sample t test and made using nQuery Advisor 5.0.

5 Statistical Methods 5.1 Analysis Populations

The modified-ITT population consisted of all patients who were randomized (analyzed "as randomized"), received at least one dose of double-blind investigational product, and had both a baseline assessment and at least one post-baseline assessment of any primary or secondary efficacy variable, irrespective of compliance with the study protocol and procedures.

The safety population was the Total Treated population defined as all patients randomized (via the central randomization system according to the protocol) and exposed to at least one dose of the investigational product, regardless of the amount of treatment administered.

5.2 Primary Efficacy Analysis

The primary efficacy variable (change in $HbA_{1c}$ from baseline to Week 12) was analyzed using an analysis of covariance (ANCOVA) model with treatment groups (two-step titration lixisenatide and placebo arms, one-step titration lixisenatide and placebo arms), randomization strata of screening $HbA_{1c}$ (<8.0, ≥8.0%), randomization strata of screening BMI (<30, ≥30 kg/m$^2$) values, and country as fixed effects and using the baseline $HbA_{1c}$ values as a covariate. In the ANCOVA model, the two titration placebo arms were included as separate treatment levels, but they were combined as one group when making comparisons using appropriate contrast (eg, to compare two-step titration lixisenatide group with combined placebo [−0.5, −0.5, 0, +1] in the order of one-step titration placebo, two-step titration placebo, one-step titration lixisenatide and two-step titration lixisenatide group).

A stepwise testing procedure was applied in order to ensure type I error control. First, two-step titration lixisenatide arm was compared with the combined placebo group (primary objective). If the test was statistically significant, then one-step titration lixisenatide arm was compared with the combined placebo group (secondary objective).

As mentioned in Section 3.1, the primary endpoint is the absolute change in $HbA_{1c}$ from baseline to Week 12 using LOCF during the on-treatment period. The on-treatment period for efficacy variables except those from meal challenge test is the time from the first dose of investigational product up to 3 days (except for Fasting Plasma Glucose (FPG) by central laboratory, which is up to 1 day) after the last dose of investigational product or up to the introduction of rescue therapy, whichever is the earliest. The on-treatment period for efficacy variables from meal challenge test including Post-prandial Plasma Glucose (PPG) and glucose excursion is the time from the first dose to the date of the last dose of investigational product or up to the introduction of rescue therapy, whichever is the earliest.

5.3 Secondary Efficacy Analysis

Figure 2:
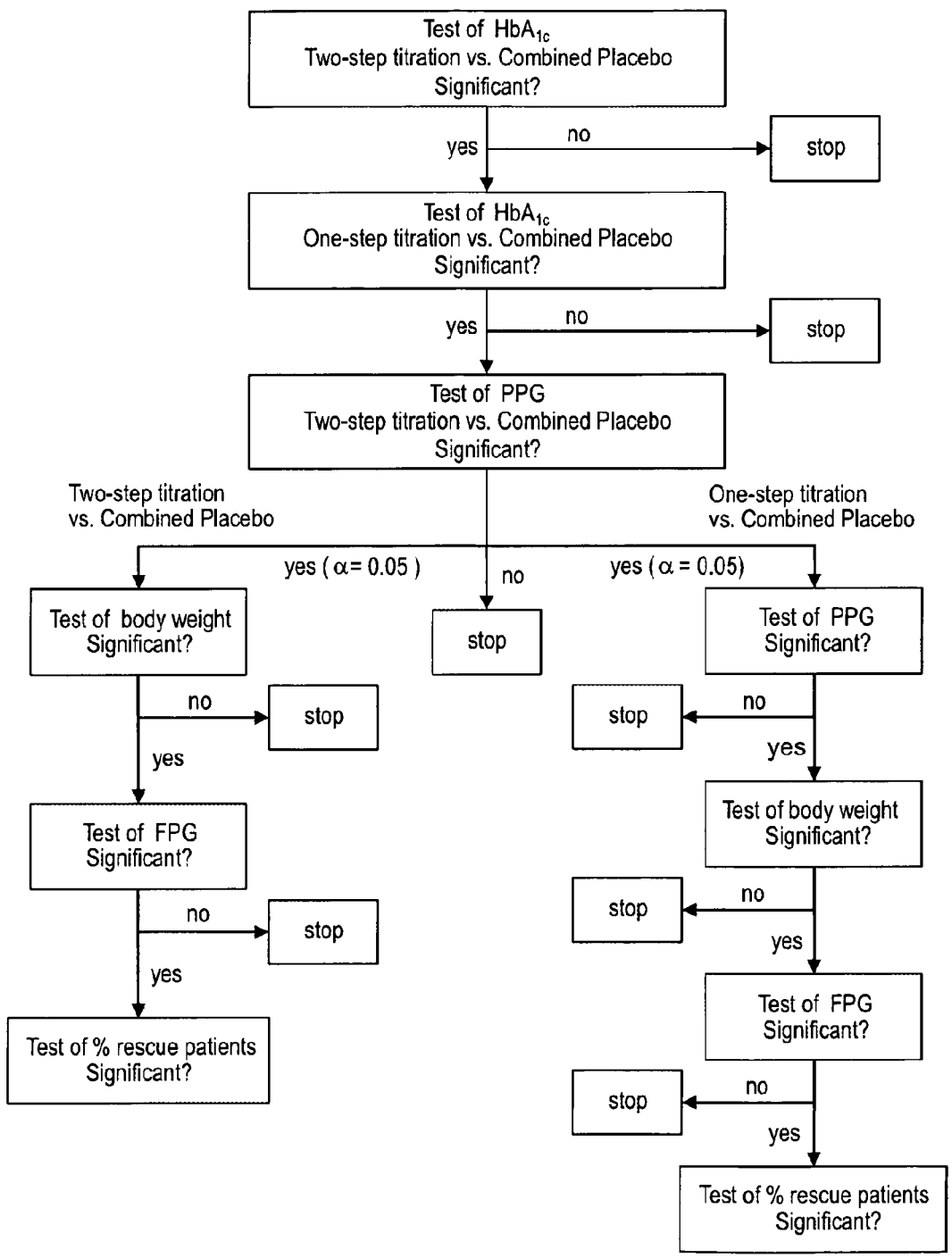

Once the primary variable was statistically significant at α=0.05 for both comparisons, the testing procedure was performed to test secondary efficacy variables, see FIG. 2.

All continuous secondary efficacy variables at Week 12 were analyzed using a similar ANCOVA model as described in Section 5.2 to compare two-step titration lixisenatide arm with combined placebo group and one-step titration lixisenatide arm with combined placebo group.

The following categorical secondary efficacy variables at Week 12 were analyzed using a Cochran-Mantel-Haenszel (CMH) method stratified on randomization strata (screening $HbA_{1c}$ (<8.0, ≥8.0%) and screening BMI (<30 kg/m$^2$, ≥30 kg/m$^2$) values):

Percentage of patients with $HbA_{1c}$<7.0% at Week 12,

Percentage of patients with $HbA_{1c}$≤6.5% at Week 12,

Percentage of patients requiring rescue therapy during 12-week treatment period, Number and percentage of patients with 5% weight loss from baseline at Week 12 were presented by treatment groups.

5.4 Safety Analysis

Treatment-emergent AEs (TEAEs) were defined as AEs that developed or worsened (according to the Investigator opinion) or became serious during the on-treatment period. The on-treatment period was defined as the time from the first dose of double-blind investigational product (IP) up to 3 days after the last injection of IP administration. The 3-day interval was chosen based on the half-life of the IP (approximately 5 times the half-life).

6 Results
6.1 Study Patients
6.1.1 Patient Accountability

Of the 795 patients screened, 434 (54.6%) patients were not randomized into the double-blind treatment. The main reason was $HbA_{1c}$ value at screening visit out of the defined protocol ranges (318 (40.0%) patients).

A total of 361 patients were randomized to one of the four treatment groups (61 in the placebo two-step titration group, 61 in the placebo one-step titration group, 120 in the lixisenatide two-step titration group, 119 in the lixisenatide one-step titration group) in 61 centers of 12 countries (Belgium, India, Israel, Japan, Korea, Mexico, Poland, Romania, Russia, Tunisia, Ukraine, and United States). All 361 randomized patients were exposed to double-blind treatment. Two patients were excluded from mITT population for efficacy analyses due to lack of post-baseline efficacy data. Table 1 below provides the number of patients included in each analysis population.

TABLE 1

| | Analysis populations - Randomized population | | | | | | |
|---|---|---|---|---|---|---|---|
| | Placebo | | | Lixisenatide | | | |
| | Two-step Titration | One-step Titration | Combined | Two-step Titration | One-step Titration | Combined | All |
| Randomized population | 61 (100%) | 61 (100%) | 122 (100%) | 120 (100%) | 119 (100%) | 239 (100%) | 361 (100%) |
| Efficacy populations Modified Intent-to-Treat (mITT) | 61 (100%) | 60 (98.4%) | 121 (99.2%) | 120 (100%) | 118 (99.2%) | 238 (99.6%) | 359 (99.4%) |
| PK Population | 6 | 1 | 7 | 114 | 117 | 231 | 238 |
| Safety population | 61 | 61 | 122 | 120 | 119 | 239 | 361 |

PK = pharmacokinetics.
Note:
The Safety and PK population patients are tabulated according to treatment actually received (as treated).
For the efficacy population, patients are tabulated according to their randomized treatment (as randomized).

6.1.2 Study Disposition

Figure 3:
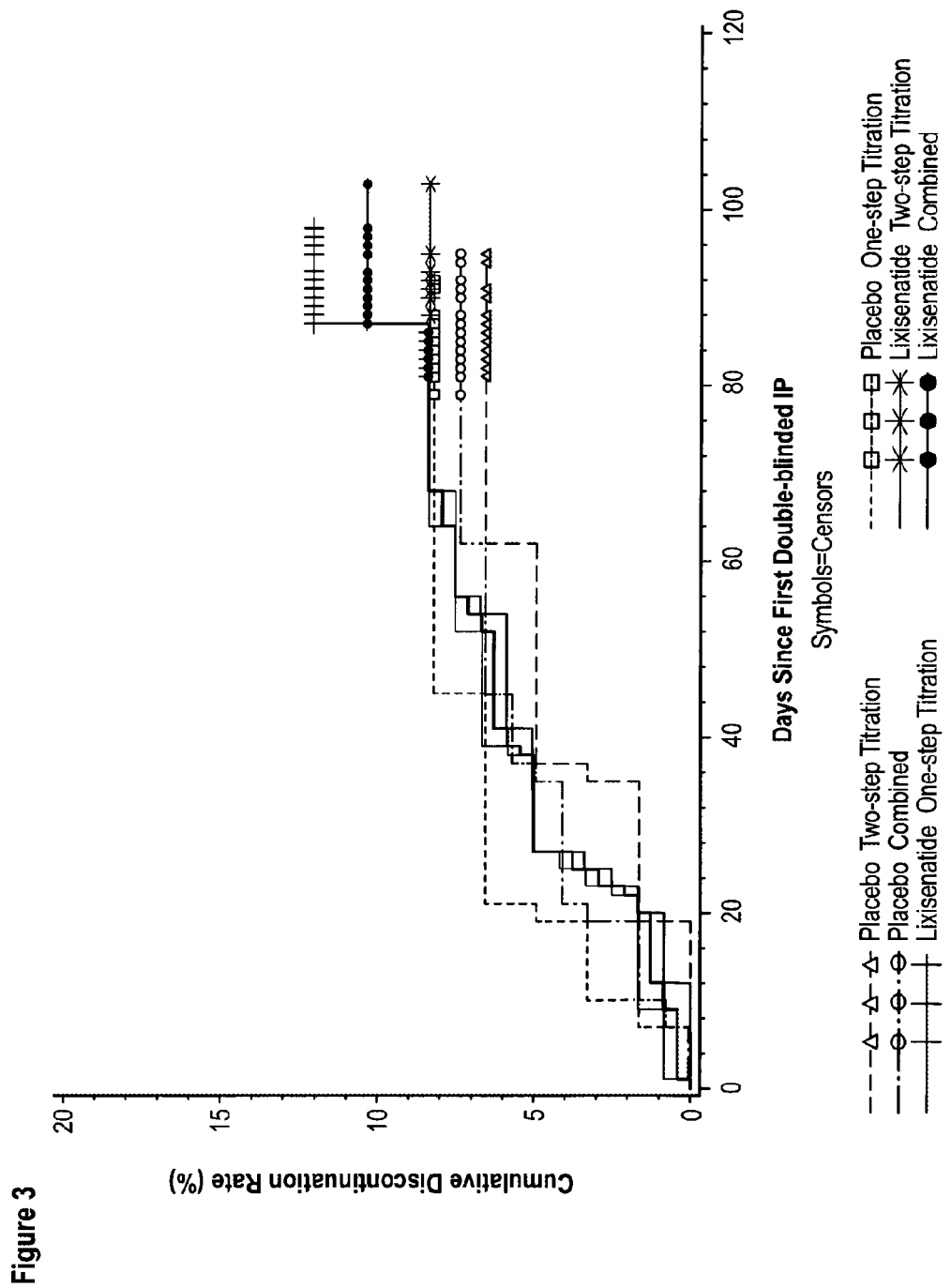

Table 2 below provides the summary of patient disposition for each treatment group. Of the 361 randomized patients, 30 (8.3%) patients prematurely discontinued from study treatment, mainly due to reasons classified as "other" (i.e. subject's decision, 18 patients) followed by adverse events (9 patients). The time-to-onset of treatment discontinuation is depicted in FIG. 3 and no particular pattern was observed.

TABLE 2

| | Patient disposition - Randomized population | | | | | |
|---|---|---|---|---|---|---|
| | Placebo | | | Lixisenatide | | |
| | Two-step Titration (N = 61) | One-step Titration (N = 61) | Combined (N = 122) | Two-step Titration (N = 120) | One-step Titration (N = 119) | Combined (N = 239) |
| Randomized and treated | 61 (100%) | 61 (100%) | 122 (100%) | 120 (100%) | 119 (100%) | 239 (100%) |
| Did not complete the study treatment period | 4 (6.6%) | 5 (8.2%) | 9 (7.4%) | 10 (8.3%) | 11 (9.2%) | 21 (8.8%) |
| Subject's request for treatment discontinuation Reason for study treatment discontinuation | 4 (6.6%) | 5 (8.2%) | 9 (7.4%) | 10 (8.3%) | 10 (8.4%) | 20 (8.4%) |
| Adverse event | 1 (1.6%) | 0 | 1 (0.8%) | 5 (4.2%) | 3 (2.5%) | 8 (3.3%) |
| Lack of efficacy | 0 | 1 (1.6%) | 1 (0.8%) | 0 | 0 | 0 |
| Poor compliance to protocol | 0 | 1 (1.6%) | 1 (0.8%) | 1 (0.8%) | 0 | 1 (0.4%) |

TABLE 2-continued

Patient disposition - Randomized population

| | Placebo | | | Lixisenatide | | |
|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) |
| Lost to follow-up | 0 | 0 | 0 | 0 | 0 | 0 |
| Other reasons | 3 (4.9%) | 3 (4.9%) | 6 (4.9%) | 4 (3.3%) | 8 (6.7%) | 12 (5.0%) |
| Status at last study contact | | | | | | |
| Alive | 61 (100%) | 61 (100%) | 122 (100%) | 120 (100%) | 119 (100%) | 239 (100%) |
| Dead | 0 | 0 | 0 | 0 | 0 | 0 |
| Lost to follow-up | 0 | 0 | 0 | 0 | 0 | 0 |

Note:
Percentages are calculated using the number of randomized patients as denominator.

6.1.3 Demographics and Baseline Characteristics

Table 3 below provides the summary of baseline and demographic characteristics for each treatment group and overall. The demographic and baseline information were generally similar across treatment groups for the safety population. The study population was balanced between genders, and the median age was 54 years. The majority of the patients were Caucasian (72.9%).

TABLE 3

Demographics and patient characteristics at screening - Safety population

| | Placebo | | | Lixisenatide | | | |
|---|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) | All (N = 361) |
| Age (years) | | | | | | | |
| Number | 61 | 61 | 122 | 120 | 119 | 239 | 361 |
| Mean (SD) | 54.5 (11.2) | 53.6 (10.9) | 54.1 (11.0) | 53.3 (9.7) | 53.8 (10.9) | 53.5 (10.3) | 53.7 (10.5) |
| Median | 55.0 | 53.0 | 54.5 | 54.0 | 53.0 | 54.0 | 54.0 |
| Min:Max | 31:75 | 33:85 | 31:85 | 21:78 | 20:82 | 20:82 | 20:85 |
| Age Group (years) [n (%)] | | | | | | | |
| Number | 61 | 61 | 122 | 120 | 119 | 239 | 361 |
| <50 | 20 (32.8%) | 20 (32.8%) | 40 (32.8%) | 44 (36.7%) | 34 (28.6%) | 78 (32.6%) | 118 (32.7%) |
| ≥50 to <65 | 30 (49.2%) | 34 (55.7%) | 64 (52.5%) | 64 (53.3%) | 69 (58.0%) | 133 (55.6%) | 197 (54.6%) |
| ≥65 to <75 | 8 (13.1%) | 5 (8.2%) | 13 (10.7%) | 11 (9.2%) | 11 (9.2%) | 22 (9.2%) | 35 (9.7%) |
| ≥75 | 3 (4.9%) | 2 (3.3%) | 5 (4.1%) | 1 (0.8%) | 5 (4.2%) | 6 (2.5%) | 11 (3.0%) |
| Sex [n (%)] | | | | | | | |
| Number | 61 | 61 | 122 | 120 | 119 | 239 | 361 |
| Male | 36 (59.0%) | 24 (39.3%) | 60 (49.2%) | 63 (52.5%) | 63 (52.9%) | 126 (52.7%) | 186 (51.5%) |
| Female | 25 (41.0%) | 37 (60.7%) | 62 (50.8%) | 57 (47.5%) | 56 (47.1%) | 113 (47.3%) | 175 (48.5%) |
| Race [n (%)] | | | | | | | |
| Number | 61 | 61 | 122 | 120 | 119 | 239 | 361 |
| Caucasian/White | 43 (70.5%) | 47 (77.0%) | 90 (73.8%) | 88 (73.3%) | 85 (71.4%) | 173 (72.4%) | 263 (72.9%) |
| Black | 2 (3.3%) | 1 (1.6%) | 3 (2.5%) | 0 | 3 (2.5%) | 3 (1.3%) | 6 (1.7%) |
| Asian/Oriental | 14 (23.0%) | 10 (16.4%) | 24 (19.7%) | 27 (22.5%) | 29 (24.4%) | 56 (23.4%) | 80 (22.2%) |
| Other | 2 (3.3%) | 3 (4.9%) | 5 (4.1%) | 5 (4.2%) | 2 (1.7%) | 7 (2.9%) | 12 (3.3%) |

TABLE 3-continued

Demographics and patient characteristics at screening - Safety population

| | Placebo | | | Lixisenatide | | | |
|---|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) | All (N = 361) |
| Ethnicity [n (%)] | | | | | | | |
| Number | 61 | 61 | 122 | 120 | 119 | 239 | 361 |
| Hispanic | 15 (24.6%) | 16 (26.2%) | 31 (25.4%) | 25 (20.8%) | 22 (18.5%) | 47 (19.7%) | 78 (21.6%) |
| Non Hispanic | 46 (75.4%) | 45 (73.8%) | 91 (74.6%) | 95 (79.2%) | 97 (81.5%) | 192 (80.3%) | 283 (78.4%) |
| Screening $HbA_{1c}$ (%) | | | | | | | |
| Number | 61 | 61 | 122 | 120 | 119 | 239 | 361 |
| Mean (SD) | 8.15 (0.87) | 8.20 (0.91) | 8.18 (0.89) | 8.11 (0.91) | 8.20 (0.84) | 8.16 (0.87) | 8.16 (0.88) |
| Median | 8.00 | 8.00 | 8.00 | 7.95 | 8.00 | 8.00 | 8.00 |
| Min:Max | 7.0:10.0 | 7.0:10.0 | 7.0:10.0 | 7.0:10.0 | 7.0:9.9 | 7.0:10.0 | 7.0:10.0 |
| Randomized strata of screening $HbA_{1c}$ (%) [n (%)] | | | | | | | |
| Number | 61 | 61 | 122 | 120 | 119 | 239 | 361 |
| <8 | 30 (49.2%) | 30 (49.2%) | 60 (49.2%) | 60 (50.0%) | 58 (48.7%) | 118 (49.4%) | 178 (49.3%) |
| ≥8 | 31 (50.8%) | 31 (50.8%) | 62 (50.8%) | 60 (50.0%) | 61 (51.3%) | 121 (50.6%) | 183 (50.7%) |
| Screening BMI ($kg/m^2$) | | | | | | | |
| Number | 61 | 61 | 122 | 120 | 119 | 239 | 361 |
| Mean (SD) | 31.70 (6.64) | 31.81 (6.79) | 31.76 (6.69) | 32.34 (6.72) | 31.65 (6.62) | 31.99 (6.66) | 31.91 (6.66) |
| Median | 30.80 | 31.18 | 30.96 | 31.13 | 30.89 | 31.05 | 31.05 |
| Min:Max | 20.1:56.0 | 20.6:58.7 | 20.1:58.7 | 20.6:50.3 | 20.8:53.7 | 20.6:53.7 | 20.1:58.7 |
| Randomized strata of screening BMI ($kg/m^2$) [n (%)] | | | | | | | |
| Number | 61 | 61 | 122 | 120 | 119 | 239 | 361 |
| <30 | 25 (41.0%) | 26 (42.6%) | 51 (41.8%) | 50 (41.7%) | 49 (41.2%) | 99 (41.4%) | 150 (41.6%) |
| ≥30 | 36 (59.0%) | 35 (57.4%) | 71 (58.2%) | 70 (58.3%) | 70 (58.8%) | 140 (58.6%) | 211 (58.4%) |

BMI = Body Mass Index.

Table 4 below describes the diabetic history for each treatment group and overall for the safety population. Diabetic histories were generally comparable across treatment groups.

TABLE 4

Disease characteristics at screening - Safety population

| | Placebo | | | Lixisenatide | | | |
|---|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) | All (N = 361) |
| Duration of diabetes (years) | | | | | | | |
| Number | 61 | 61 | 122 | 120 | 119 | 239 | 361 |
| Mean (SD) | 2.49 (2.44) | 2.47 (2.87) | 2.48 (2.66) | 2.59 (3.51) | 2.48 (3.82) | 2.53 (3.66) | 2.52 (3.35) |
| Median | 1.46 | 1.03 | 1.37 | 1.42 | 1.11 | 1.30 | 1.33 |
| Min:Max | 0.2:9.6 | 0.2:12.5 | 0.2:12.5 | 0.2:21.5 | 0.2:23.9 | 0.2:23.9 | 0.2:23.9 |

TABLE 4-continued

| | Disease characteristics at screening - Safety population | | | | | | |
|---|---|---|---|---|---|---|---|
| | Placebo | | | Lixisenatide | | | |
| | Two-step Titration (N = 61) | One-step Titration (N = 61) | Combined (N = 122) | Two-step Titration (N = 120) | One-step Titration (N = 119) | Combined (N = 239) | All (N = 361) |
| Age at onset of T2D (years) | | | | | | | |
| Number | 61 | 61 | 122 | 120 | 119 | 239 | 361 |
| Mean (SD) | 51.97 (11.27) | 51.18 (11.17) | 51.57 (11.18) | 50.69 (9.53) | 51.30 (11.27) | 51.00 (10.41) | 51.19 (10.67) |
| Median | 53.00 | 51.00 | 52.00 | 51.00 | 51.00 | 51.00 | 51.00 |
| Min:Max | 30.0:75.0 | 28.0:83.0 | 28.0:83.0 | 21.0:76.0 | 17.0:82.0 | 17.0:82.0 | 17.0:83.0 |
| Prior use of GLP-1 receptor agonist [n (%)] | | | | | | | |
| Number | 61 | 61 | 122 | 120 | 119 | 239 | 361 |
| Yes | 1 (1.6%) | 1 (1.6%) | 2 (1.6%) | 0 | 1 (0.8%) | 1 (0.4%) | 3 (0.8%) |
| No | 60 (98.4%) | 60 (98.4%) | 120 (98.4%) | 120 (100%) | 118 (99.2%) | 238 (99.6%) | 358 (99.2%) |
| Diabetic retinopathy [n (%)] | | | | | | | |
| Number | 59 | 59 | 118 | 118 | 119 | 237 | 355 |
| Yes | 1 (1.7%) | 1 (1.7%) | 2 (1.7%) | 3 (2.5%) | 3 (2.5%) | 6 (2.5%) | 8 (2.3%) |
| No | 53 (89.8%) | 53 (89.8%) | 106 (89.8%) | 110 (93.2%) | 106 (89.1%) | 216 (91.1%) | 322 (90.7%) |
| Diabetic sensory or motor neuropathy [n (%)] | | | | | | | |
| Number | 59 | 59 | 118 | 117 | 119 | 236 | 354 |
| Yes | 2 (3.4%) | 4 (6.8%) | 6 (5.1%) | 6 (5.1%) | 2 (1.7%) | 8 (3.4%) | 14 (4.0%) |
| No | 55 (93.2%) | 52 (88.1%) | 107 (90.7%) | 107 (91.5%) | 112 (94.1%) | 219 (92.8%) | 326 (92.1%) |
| Diabetic autonomic neuropathy [n (%)] | | | | | | | |
| Number | 59 | 59 | 118 | 118 | 119 | 237 | 355 |
| Yes | 0 | 0 | 0 | 0 | 0 | 0 | 0 |
| No | 57 (96.6%) | 55 (93.2%) | 112 (94.9%) | 114 (96.6%) | 114 (95.8%) | 228 (96.2%) | 340 (95.8%) |
| Diabetic nephropathy [n (%)] | | | | | | | |
| Number | 59 | 59 | 118 | 118 | 119 | 237 | 355 |
| Yes | 0 | 0 | 0 | 1 (0.8%) | 0 | 1 (0.4%) | 1 (0.3%) |
| No | 57 (96.6%) | 55 (93.2%) | 112 (94.9%) | 111 (94.1%) | 113 (95.0%) | 224 (94.5%) | 336 (94.6%) |
| Albuminuria [n (%)] | | | | | | | |
| Number | 5 | 7 | 12 | 9 | 11 | 20 | 32 |
| <3 mg/L (Not reportable) | 0 | 1 (14.3%) | 1 (8.3%) | 2 (22.2%) | 3 (27.3%) | 5 (25.0%) | 6 (18.8%) |
| ≥3 mg/L (Reportable) | 5 (100%) | 6 (85.7%) | 11 (91.7%) | 7 (77.8%) | 8 (72.7%) | 15 (75.0%) | 26 (81.3%) |
| <20 mg/L | 3 (60.0%) | 3 (50.0%) | 6 (54.5%) | 5 (71.4%) | 6 (75.0%) | 11 (73.3%) | 17 (65.4%) |
| ≥20-<200 mg/L | 2 (40.0%) | 2 (33.3%) | 4 (36.4%) | 2 (28.6%) | 2 (25.0%) | 4 (26.7%) | 8 (30.8%) |
| ≥200 mg/L | 0 | 1 (16.7%) | 1 (9.1%) | 0 | 0 | 0 | 1 (3.8%) |

TABLE 4-continued

| | Disease characteristics at screening - Safety population | | | | | | |
|---|---|---|---|---|---|---|---|
| | Placebo | | | Lixisenatide | | | |
| | Two-step Titration (N = 61) | One-step Titration (N = 61) | Combined (N = 122) | Two-step Titration (N = 120) | One-step Titration (N = 119) | Combined (N = 239) | All (N = 361) |
| Creatinine clearance (ml/min) | | | | | | | |
| Number | 61 | 61 | 122 | 120 | 119 | 239 | 361 |
| Mean (SD) | 129.65 (48.86) | 124.41 (46.24) | 127.03 (47.44) | 129.22 (47.70) | 123.67 (44.63) | 126.46 (46.18) | 126.65 (46.55) |
| Median | 129.82 | 120.41 | 122.84 | 122.79 | 118.51 | 120.94 | 121.73 |
| Min:Max | 56.9:265.9 | 27.6:324.1 | 27.6:324.1 | 49.9:304.7 | 46.2:283.6 | 46.2:304.7 | 27.6:324.1 |
| Creatinine clearance [n (%)] | | | | | | | |
| Number | 61 | 61 | 122 | 120 | 119 | 239 | 361 |
| <30 ml/min (severe renal impairment) | 0 | 1 (1.6%) | 1 (0.8%) | 0 | 0 | 0 | 1 (0.3%) |
| ≥30-<50 ml/min (moderate renal impairment) | 0 | 0 | 0 | 1 (0.8%) | 2 (1.7%) | 3 (1.3%) | 3 (0.8%) |
| ≥50-≤80 ml/min (mild renal impairment) | 9 (14.8%) | 6 (9.8%) | 15 (12.3%) | 13 (10.8%) | 17 (14.3%) | 30 (12.6%) | 45 (12.5%) |
| >80 ml/min (no renal impairment | 52 (85.2%) | 54 (88.5%) | 106 (86.9%) | 106 (88.3%) | 100 (84.0%) | 206 (86.2%) | 312 (86.4%) |

GLP-1 = Glucagon like peptide-1.

Table 5 below presents the descriptive summaries of efficacy variables at baseline for each treatment group and overall for the safety population. Efficacy variables at baseline were generally comparable across treatment groups.

TABLE 5

| | Baseline efficacy variables - Safety population | | | | | | |
|---|---|---|---|---|---|---|---|
| | Placebo | | | Lixisenatide | | | |
| | Two-step Titration (N = 61) | One-step Titration (N = 61) | Combined (N = 122) | Two-step Titration (N = 120) | One-step Titration (N = 119) | Combined (N = 239) | All (N = 361) |
| HbA$_{1c}$ (%) | | | | | | | |
| Number | 61 | 61 | 122 | 120 | 119 | 239 | 361 |
| Mean (SD) | 8.10 (0.95) | 8.05 (0.87) | 8.07 (0.91) | 7.98 (0.92) | 8.07 (0.87) | 8.03 (0.89) | 8.04 (0.90) |
| Median | 7.90 | 7.80 | 7.80 | 7.70 | 7.90 | 7.80 | 7.80 |
| Min:Max | 6.5:10.7 | 6.5:10.1 | 6.5:10.7 | 6.6:10.1 | 6.7:10.5 | 6.6:10.5 | 6.5:10.7 |
| Weight (kg) | | | | | | | |
| Number | 61 | 61 | 122 | 120 | 119 | 239 | 361 |
| Mean (SD) | 86.53 (19.91) | 85.64 (24.45) | 86.08 (22.21) | 89.04 (22.16) | 86.50 (21.00) | 87.77 (21.58) | 87.20 (21.78) |
| Median | 82.00 | 82.00 | 82.00 | 87.00 | 84.50 | 85.20 | 84.20 |
| Min:Max | 48.0:133.0 | 46.2:186.0 | 46.2:186.0 | 47.0:160.0 | 44.5:159.2 | 44.5:160.0 | 44.5:186.0 |
| FPG (mmol/L) | | | | | | | |
| Number | 61 | 61 | 122 | 120 | 119 | 239 | 361 |
| Mean (SD) | 8.88 (2.26) | 8.93 (2.07) | 8.90 (2.16) | 9.15 (1.99) | 9.04 (1.97) | 9.09 (1.97) | 9.03 (2.04) |
| Median | 8.50 | 8.50 | 8.50 | 8.80 | 8.70 | 8.80 | 8.60 |
| Min:Max | 4.7:15.4 | 5.8:17.5 | 4.7:17.5 | 4.8:16.7 | 5.6:16.3 | 4.8:16.7 | 4.7:17.5 |

TABLE 5-continued

Baseline efficacy variables - Safety population

| | Placebo | | | Lixisenatide | | | |
|---|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) | All (N = 361) |
| 2-hour post-prandial plasma glucose* (mmol/L) | | | | | | | |
| Number | 26 | 34 | 60 | 59 | 65 | 124 | 184 |
| Mean (SD) | 14.02 (5.06) | 14.45 (4.74) | 14.27 (4.84) | 14.81 (3.87) | 14.62 (3.41) | 14.71 (3.62) | 14.57 (4.05) |
| Median | 14.05 | 14.15 | 14.15 | 14.80 | 14.50 | 14.65 | 14.45 |
| Min:Max | 5.5:23.7 | 6.5:30.2 | 5.5:30.2 | 6.1:23.5 | 6.5:22.6 | 6.1:23.5 | 5.5:30.2 |
| Glucose excursion* (mmol/L) | | | | | | | |
| Number | 26 | 34 | 60 | 59 | 65 | 124 | 184 |
| Mean (SD) | 4.77 (4.23) | 4.86 (3.30) | 4.82 (3.69) | 5.67 (3.05) | 5.34 (2.96) | 5.49 (3.00) | 5.27 (3.25) |
| Median | 5.85 | 4.80 | 5.10 | 5.60 | 5.50 | 5.50 | 5.50 |
| Min:Max | −5.9:13.1 | −1.1:11.8 | −5.9:13.1 | −2.9:11.5 | −1.9:11.9 | −2.9:11.9 | −5.9:13.1 |

*For patients in selected sites where the meal challenge test was performed.
FPG = Fasting Plasma Glucose.
Glucose excursion = 2-hour postprandial plasma glucose − plasma glucose 30 minutes prior to the meal test, before study drug administration.

6.1.4 Dosage and Duration

Treatment exposure and dosage are summarized in Table 6, Table 7 and Table 8 below. The average treatment exposure was similar across treatment groups. Of the 361 safety patients, 335 (92.8%) were exposed to 57 days or more, 349 (96.7%) reached the target dose 20 μg at the end of titration, and 335 (92.8%) had the final dose with the target dose 20 μg at the end of double-blind treatment.

TABLE 6

Exposure to investigational product - Safety population

| | Placebo | | | Lixisenatide | | |
|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) |
| Cumulative exposure to treatment (patient years) | 13.8 | 13.4 | 27.2 | 26.7 | 26.6 | 53.3 |
| Duration of study treatment (days) | | | | | | |
| Number | 61 | 61 | 122 | 120 | 119 | 239 |
| Mean (SD) | 82.6 (12.8) | 80.0 (18.5) | 81.3 (15.9) | 81.2 (16.5) | 81.8 (15.3) | 81.5 (15.9) |
| Median | 85.0 | 85.0 | 85.0 | 85.0 | 85.0 | 85.0 |
| Min:Max | 19:95 | 7:92 | 7:95 | 1:103 | 12:98 | 1:103 |
| Duration of study treatment by category [n (%)] | | | | | | |
| 1-14 days | 0 | 2 (3.3%) | 2 (1.6%) | 2 (1.7%) | 1 (0.8%) | 3 (1.3%) |
| 15-28 days | 1 (1.6%) | 2 (3.3%) | 3 (2.5%) | 4 (3.3%) | 5 (4.2%) | 9 (3.8%) |
| 29-56 days | 2 (3.3%) | 1 (1.6%) | 3 (2.5%) | 3 (2.5%) | 3 (2.5%) | 6 (2.5%) |
| 57-84 days | 15 (24.6%) | 10 (16.4%) | 25 (20.5%) | 14 (11.7%) | 18 (15.1%) | 32 (13.4%) |
| >84 days | 43 (70.5%) | 46 (75.4%) | 89 (73.0%) | 97 (80.8%) | 92 (77.3%) | 189 (79.1%) |
| Number of patients with duration of study treatment by category [n (%)] | | | | | | |
| ≥1 day | 61 (100%) | 61 (100%) | 122 (100%) | 120 (100%) | 119 (100%) | 239 (100%) |
| ≥15 days | 61 (100%) | 59 (96.7%) | 120 (98.4%) | 118 (98.3%) | 118 (99.2%) | 236 (98.7%) |
| ≥29 days | 60 (98.4%) | 57 (93.4%) | 117 (95.9%) | 114 (95.0%) | 113 (95.0%) | 227 (95.0%) |
| ≥57 days | 58 (95.1%) | 56 (91.8%) | 114 (93.4%) | 111 (92.5%) | 110 (92.4%) | 221 (92.5%) |
| ≥85 days | 43 (70.5%) | 46 (75.4%) | 89 (73.0%) | 97 (80.8%) | 92 (77.3%) | 189 (79.1%) |

Duration of exposure = (date of the last double-blind IP injection − date of the first double-blind IP injection) + 1.

TABLE 7

Number (%) of patients by final dose at the end of the double-blind treatment - Safety population

| Final Dose | Placebo | | | Lixisenatide | | |
|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) |
| 10 µg | 0 | 1 (1.6%) | 1 (0.8%) | 5 (4.2%) | 13 (10.9%) | 18 (7.5%) |
| 15 µg | 0 | 0 | 0 | 6 (5.0%) | 1 (0.8%) | 7 (2.9%) |
| 20 µg | 61 (100%) | 60 (98.4%) | 121 (99.2%) | 109 (90.8%) | 105 (88.2%) | 214 (89.5%) |

Dose = Dose of active drug or volume-matched placebo.
Note:
Percents are calculated using the number of safety patients as the denominator.

TABLE 8

Number (%) of patients by dose at the end of titration - Safety population

| Dose at the end of titration | Placebo | | | Lixisenatide | | |
|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) |
| <10 µg | 0 | 0 | 0 | 0 | 1 (0.8%) | 1 (0.4%) |
| 10 µg | 0 | 2 (3.3%) | 2 (1.6%) | 3 (2.5%) | 3 (2.5%) | 6 (2.5%) |
| 15 µg | 0 | 0 | 0 | 3 (2.5%) | 0 | 3 (1.3%) |
| 20 µg | 61 (100%) | 59 (96.7%) | 120 (98.4%) | 114 (95.0%) | 115 (96.6%) | 229 (95.8%) |

Dose = Dose of active drug or volume-matched placebo.
The scheduled visit for end of titration per protocol would be Visit 5/Week 2.
Note:
Percents are calculated using the number of safety patients as the denominator.

6.2 Efficacy 6.2.1 Primary Efficacy Parameter

Main Analysis

Figure 4:
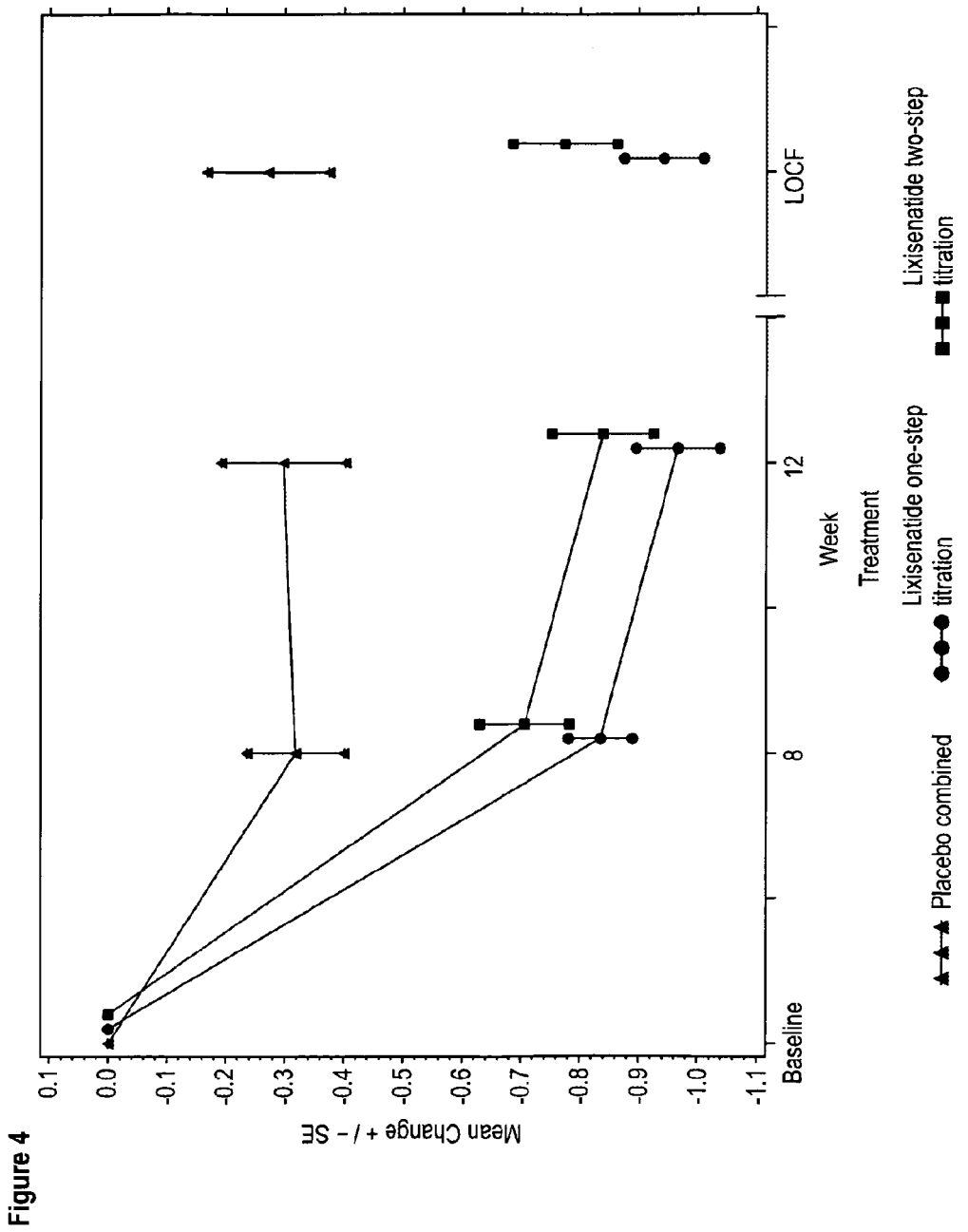

Table 1 summarizes the results of the primary efficacy parameter, the change from baseline to endpoint in $HbA_{1c}$ using LOCF ANCOVA analysis. FIG. 4 illustrates the Mean (±SE) change from baseline in $HbA_{1c}$ over time during the 12-week double-blind treatment.

Based on the pre-specified primary analysis, both lixisenatide-treated groups demonstrated statistically significant reduction of $HbA_{1c}$ from baseline to endpoint, compared to the placebo group (for the lixisenatide two-step titration group, LS mean difference=−0.54%; p-value=<0.0001; for the lixisenatide one-step titration group, LS mean difference=−0.66%; p-value=<0.0001). Moreover $HbA_{1c}$ seems to reach a plateau after week 8 in the placebo group, while $HbA_{1c}$ is continuously decreasing in both lixisenatide-treated groups.

TABLE 9

Mean change in $HbA_{1c}$ (%) from baseline to endpoint - mITT population

| $HbA_{1c}$ (%) | Placebo | Lixisenatide | |
|---|---|---|---|
| | Combined (N = 121) | Two-step Titration (N = 120) | One-step Titration (N = 118) |
| Baseline | | | |
| Number | 112 | 113 | 114 |
| Mean (SD) | 8.07 (0.92) | 7.97 (0.91) | 8.06 (0.85) |
| Median | 7.80 | 7.70 | 7.90 |
| Min:Max | 6.5:10.7 | 6.6:9.9 | 6.7:10.5 |
| Endpoint | | | |
| Number | 112 | 113 | 114 |
| Mean (SD) | 7.80 (1.35) | 7.20 (1.19) | 7.11 (0.89) |
| Median | 7.50 | 6.90 | 7.00 |
| Min:Max | 5.4:13.6 | 5.2:13.0 | 5.4:9.8 |
| Change from baseline to endpoint | | | |
| Number | 112 | 113 | 114 |
| Mean (SD) | −0.27 (1.09) | −0.77 (0.94) | −0.94 (0.72) |
| Median | −0.30 | −0.80 | −0.90 |
| Min:Max | −2.7:3.3 | −3.0:3.1 | −3.0:0.8 |

TABLE 9-continued

Mean change in HbA$_{1c}$ (%) from baseline to endpoint - mITT population

| HbA$_{1c}$ (%) | Placebo Combined (N = 121) | Lixisenatide | |
|---|---|---|---|
| | | Two-step Titration (N = 120) | One-step Titration (N = 118) |
| LS Mean (SE) [a] | −0.19 (0.121) | −0.73 (0.116) | −0.85 (0.119) |
| LS Mean difference (SE) vs. placebo combined [a] | | −0.54 (0.123) | −0.66 (0.122) |
| 95% CI | | (−0.785 to −0.300) | (−0.903 to −0.423) |
| p-value | | <0.0001 | <0.0001 |

[a] Analysis of covariance (ANCOVA) model with treatment groups (two-step titration lixisenatide and placebo arms, one-step titration lixisenatide and placebo arms), randomization strata of screening HbA$_{1c}$ (<8.0, ≥8.0%), randomization strata of screening body mass index (<30, ≥30 kg/m$^2$), and country as fixed effects and baseline HbA$_{1c}$ value as a covariate.
The comparison between each lixisenatide group and the placebo combined group was achieved through appropriate contrasts.
The analysis excluded measurements obtained after the introduction of rescue medication and/or after the treatment cessation plus 3 days.

Secondary Analyses

Table 10 summarizes the proportion of patients with treatment response (HbA$_{1c}$≤6.5 or <7% at endpoint, respectively). Treatment responses were similar between lixisenatide-treated groups and the treatment difference between each of lixisenatide-treated groups versus placebo was statistically significant.

TABLE 10

Number (%) of patients with HbA$_{1c}$ value ≤6.5% or <7% at endpoint - mITT population

| HbA$_{1c}$ (%) | Placebo Combined (N = 121) | Lixisenatide | |
|---|---|---|---|
| | | Two-step Titration (N = 120) | One-step Titration (N = 118) |
| Number | 112 | 113 | 114 |
| ≤6.5% | 14 (12.5%) | 36 (31.9%) | 29 (25.4%) |
| >6.5% | 98 (87.5%) | 77 (68.1%) | 85 (74.6%) |
| p-value vs. Placebo Combined[a] | — | 0.0005 | 0.0095 |
| Number | 112 | 113 | 114 |
| <7.0% | 30 (26.8%) | 59 (52.2%) | 53 (46.5%) |

TABLE 10-continued

Number (%) of patients with HbA$_{1c}$ value ≤6.5% or <7% at endpoint - mITT population

| HbA$_{1c}$ (%) | Placebo Combined (N = 121) | Lixisenatide | |
|---|---|---|---|
| | | Two-step Titration (N = 120) | One-step Titration (N = 118) |
| ≥7.0% | 82 (73.2%) | 54 (47.8%) | 61 (53.5%) |
| p-value vs. Placebo Combined[a] | — | <0.0001 | 0.0013 |

[a]Cochran-Mantel-Haenszel (CMH) method stratified by randomization strata of screening HbA$_{1c}$ (≤8.0 or ≥8.0%) and randomization strata of screening body mass index (<30 or ≥30 kg/m$^2$).
The analysis excluded measurements obtained after the introduction of rescue medication and/or after the treatment cessation plus 3 day.

6.2.2 Secondary Efficacy Parameters

Table 11, Table 12, Table 13 and Table 15 summarize the ANCOVA analyses of 2-hour post-prandial plasma glucose, glucose excursion, body weight and FPG, respectively.

Table 14 and Table 16 present the proportion of patients with weight loss 5% from baseline to endpoint and the percentage of patients requiring rescue therapy, respectively. FIG. 5 and FIG. 6 demonstrate the Mean (±SE) change from baseline in body weight and FPG over time during the 12-week double-blind treatment period.

Both lixisenatide-treated groups showed statistically significant improvement over the placebo group in 2-hour post-prandial plasma glucose, supported by the same ANCOVA analysis in glucose excursion.

TABLE 11

Mean change in 2-hour post-prandial plasma glucose (mmol/L) from baseline to endpoint in selected sites - mITT population

| 2-hr Post-prandial Plasma Glucose (mmol/L) | Placebo Combined (N = 62) | Lixisenatide | |
|---|---|---|---|
| | | Two-step Titration (N = 60) | One-step Titration (N = 65) |
| Baseline | | | |
| Number | 54 | 53 | 62 |
| Mean (SD) | 13.99 (4.78) | 14.67 (3.78) | 14.55 (3.36) |
| Median | 14.15 | 14.80 | 14.15 |
| Min:Max | 5.5:30.2 | 6.1:22.0 | 6.5:22.6 |
| Endpoint | | | |
| Number | 54 | 53 | 62 |
| Mean (SD) | 13.42 (4.54) | 9.90 (5.05) | 8.77 (4.11) |

TABLE 11-continued

Mean change in 2-hour post-prandial plasma glucose (mmol/L) from baseline to endpoint in selected sites - mITT population

| | Placebo | Lixisenatide | |
| --- | --- | --- | --- |
| 2-hr Post-prandial Plasma Glucose (mmol/L) | Combined (N = 62) | Two-step Titration (N = 60) | One-step Titration (N = 65) |
| Median | 12.80 | 8.40 | 8.20 |
| Min:Max | 4.7:26.3 | 3.5:25.1 | 4.3:26.3 |
| Change from baseline to endpoint | | | |
| Number | 54 | 53 | 62 |
| Mean (SD) | −0.57 (4.44) | −4.77 (4.53) | −5.77 (3.90) |
| Median | −0.90 | −4.90 | −5.80 |
| Min:Max | −14.7:17.8 | −16.6:5.3 | −12.7:10.4 |
| LS Mean (SE) [a] | −0.65 (0.563) | −4.51 (0.572) | −5.47 (0.549) |
| LS Mean difference (SE) vs. placebo combined [a] | | −3.86 (0.765) | −4.82 (0.741) |
| 95% CI | | (−5.375 to −2.353) | (−6.287 to −3.361) |
| p-value | | <0.0001 | <0.0001 |

[a] Analysis of covariance (ANCOVA) model with treatment groups (two-step titration lixisenatide and placebo arms, one-step titration lixisenatide and placebo arms), randomization strata of screening $HbA_{1c}$ (<8.0, ≥8.0%), randomization strata of screening body mass index (<30, ≥30 kg/m$^2$), and country as fixed effects and baseline 2-hour post-prandial plasma glucose value as a covariate.
The comparison between each lixisenatide group and the placebo combined group was achieved through appropriate contrasts.
The analysis excluded measurements obtained after the introduction of rescue medication and/or after the treatment cessation.

TABLE 12

Mean change in glucose excursion (mmol/L) from baseline to endpoint in selected sites mITT population

| | Placebo | Lixisenatide | |
| --- | --- | --- | --- |
| Glucose Excursion (mmol/L) | Combined (N = 62) | Two-step Titration (N = 60) | One-step Titration (N = 65) |
| Baseline | | | |
| Number | 54 | 53 | 62 |
| Mean (SD) | 4.72 (3.65) | 5.45 (3.02) | 5.25 (2.89) |
| Median | 5.10 | 5.40 | 5.40 |
| Min:Max | −5.9:13.1 | −2.9:11.5 | −1.9:10.8 |
| Endpoint | | | |
| Number | 54 | 53 | 62 |
| Mean (SD) | 4.20 (3.42) | 1.39 (3.90) | 0.60 (3.09) |
| Median | 4.25 | 0.50 | −0.10 |
| Min:Max | −5.9:12.4 | −4.4:11.8 | −3.2:13.8 |
| Change from baseline to endpoint | | | |
| Number | 54 | 53 | 62 |
| Mean (SD) | −0.52 (3.76) | −4.06 (3.60) | −4.66 (3.27) |
| Median | −0.82 | −4.20 | −4.53 |
| Min:Max | −12.8:10.3 | −12.0:3.8 | −11.2:3.5 |
| LS Mean (SE) [a] | −0.67 (0.447) | −3.77 (0.454) | −4.36 (0.436) |
| LS Mean difference (SE) vs. placebo combined [a] | | −3.10 (0.608) | −3.69 (0.589) |
| 95% CI | | (−4.300 to −1.898) | (−4.853 to −2.527) |

[a] Analysis of covariance (ANCOVA) model with treatment groups (two-step titration lixisenatide and placebo arms, one-step titration lixisenatide and placebo arms), randomization strata of screening $HbA_{1c}$ (<8.0, ≥8.0%), randomization strata of screening body mass index (<30, ≥30 kg/m$^2$), and country as fixed effects and baseline glucose excursion value as a covariate.
The comparison between each lixisenatide group and the placebo combined group was achieved through appropriate contrasts.
The analysis excluded measurements obtained after the introduction of rescue medication and/or after the treatment cessation.
Glucose excursion = 2-hour postprandial plasma glucose − plasma glucose 30 minutes prior to the meal test before study drug administration.

No difference in the changes in body weight were observed between the lixisenatide groups and placebo (Table 13), likewise a comparable percentage of patients across the treatment groups who had lost weight 5% or more in body weight (Table 14).

TABLE 13

Mean change in body weight (kg) from baseline to endpoint - mITT population

| Body Weight (kg) | Placebo Combined (N = 121) | Lixisenatide Two-step Titration (N = 120) | Lixisenatide One-step Titration (N = 118) |
|---|---|---|---|
| Baseline | | | |
| Number | 116 | 117 | 115 |
| Mean (SD) | 85.75 (22.06) | 89.13 (22.21) | 87.14 (20.93) |
| Median | 82.00 | 87.00 | 84.70 |
| Min:Max | 46.2:186.0 | 47.0:160.0 | 44.5:159.2 |
| Endpoint | | | |
| Number | 116 | 117 | 115 |
| Mean (SD) | 83.77 (21.57) | 87.12 (21.78) | 85.21 (20.94) |
| Median | 80.60 | 84.00 | 82.90 |
| Min:Max | 44.8:186.0 | 47.5:156.0 | 45.1:156.3 |
| Change from baseline to endpoint | | | |
| Number | 116 | 117 | 115 |
| Mean (SD) | −1.98 (2.77) | −2.01 (2.68) | −1.92 (2.78) |
| Median | −1.35 | −1.50 | −2.00 |
| Min:Max | −12.9:2.7 | −11.9:4.4 | −11.8:6.1 |
| LS Mean (SE) [a] | −1.98 (0.341) | −1.96 (0.326) | −1.92 (0.338) |
| LS Mean difference (SE) vs. placebo combined [a] | | 0.02 (0.344) | 0.06 (0.343) |
| 95% CI | | (−0.654 to 0.701) | (−0.612 to 0.737) |
| p-value | | 0.9462 | 0.8549 |

[a] Analysis of covariance (ANCOVA) model with treatment groups (two-step titration lixisenatide and placebo arms, one-step titration lixisenatide and placebo arms), randomization strata of screening HbA$_{1c}$ (<8.0, ≥8.0%), randomization strata of screening body mass index (<30, ≥30 kg/m$^2$), and country as fixed effects and baseline body weight value as a covariate.
The comparison between each lixisenatide group and the placebo combined group was achieved through appropriate contrasts.
The analysis excluded measurements obtained after the introduction of rescue medication and/or after the treatment cessation plus 3 days.

TABLE 14

Number (%) of patients with >=5% weight loss from baseline to endpoint - mITT population

| Weight loss | Placebo Combined (N = 121) | Lixisenatide Two-step Titration (N = 120) | Lixisenatide One-step Titration (N = 118) |
|---|---|---|---|
| Number | 116 | 117 | 115 |
| ≥5% | 20 (17.2%) | 19 (16.2%) | 21 (18.3%) |
| <5% | 96 (82.8%) | 98 (83.8%) | 94 (81.7%) |

The analysis excluded measurements obtained after the introduction of rescue medication and/or after the treatment cessation plus 3 days.

Per the testing strategy adjusting for multiplicity (step-down procedure), inferential testing for FPG was made in an exploratory manner because the preceding test (body weight) failed to show statistically significant between-group difference. Both lixisenatide-treated groups demonstrated meaningful improvement over the placebo group in FPG using ANCOVA analysis without multiplicity adjustment.

TABLE 15

Mean change in fasting plasma glucose (mmol/L)
from baseline to endpoint - mITT population

| Fasting Plasma Glucose (mmol/L) | Placebo Combined (N = 121) | Lixisenatide Two-step Titration (N = 120) | Lixisenatide One-step Titration (N = 118) |
|---|---|---|---|
| Baseline | | | |
| Number | 121 | 119 | 118 |
| Mean (SD) | 8.91 (2.17) | 9.17 (1.98) | 9.02 (1.97) |
| Median | 8.50 | 8.80 | 8.65 |
| Min:Max | 4.7:17.5 | 4.8:16.7 | 5.6:16.3 |
| Endpoint | | | |
| Number | 121 | 119 | 118 |
| Mean (SD) | 9.16 (2.96) | 8.51 (2.38) | 8.16 (1.73) |
| Median | 8.40 | 8.20 | 7.88 |
| Min:Max | 4.7:22.9 | 4.6:19.7 | 5.0:14.5 |
| Change from baseline to endpoint | | | |
| Number | 121 | 119 | 118 |
| Mean (SD) | 0.25 (2.52) | −0.66 (1.95) | −0.87 (1.62) |
| Median | −0.05 | −0.50 | −0.70 |
| Min:Max | −5.1:17.6 | −7.5:6.3 | −6.4:4.6 |
| LS Mean (SE) [a] | 0.19 (0.255) | −0.68 (0.247) | −0.89 (0.254) |
| LS Mean difference (SE) vs. placebo combined [a] | | −0.87 (0.257) | −1.08 (0.257) |
| 95% CI | | (−1.374 to −0.361) | (−1.586 to −0.577) |
| p-value | | 0.0008 | <0.0001 |

[a] Analysis of covariance (ANCOVA) model with treatment groups (two-step titration lixisenatide and placebo arms, one-step titration lixisenatide and placebo arms), randomization strata of screening HbA$_{1c}$ (<8.0, ≥8.0%), randomization strata of screening body mass index (<30, ≥30 kg/m$^2$), and country as fixed effects and baseline fasting plasma glucose value as a covariate.
The comparison between each lixisenatide group and the placebo combined group was achieved through appropriate contrasts.
The analysis excluded measurements obtained after the introduction of rescue medication and/or after the treatment cessation plus 1 day.

There was no evidence for difference difference between the lixisenatide-treated groups and the placebo group in percentage of patients who required rescue therapy due to the low incidence of rescued patients during the double-blind treatment period.

TABLE 16

Number (%) of patients requiring rescue therapy during
the double-blind treatment period - mITT population

| Requiring rescue therapy | Placebo Combined (N = 121) | Lixisenatide Two-step Titration (N = 120) | Lixisenatide One-step Titration (N = 118) |
|---|---|---|---|
| Number | 121 | 120 | 118 |
| Yes | 3 (2.5%) | 2 (1.7%) | 1 (0.8%) |
| No | 118 (97.5%) | 118 (98.3%) | 117 (99.2%) |
| p-value vs. Placebo Combined[a] | — | 0.6518 | 0.3260 |

[a] Cochran-Mantel-Haenszel (CMH) method stratified by randomization strata of screening HbA$_{1c}$ (<8.0 or ≥8.0%) and randomization strata of screening BMI (<30 or ≥30 kg/m$^2$).

6.3 Safety

Table 17 below presents the overall summary of patients who had adverse events during the double-blind treatment and Table 18, and Table 19 show serious TEAEs, and TEAEs leading to treatment discontinuation, respectively. The proportion of patients who had TEAEs was generally comparable between the placebo group and the lixisenatide-treated groups. The incidence of serious TEAE was low, with 5 occurrences (4.1%) in the placebo group, 1 (0.8%) in the lixisenatide two-step titration group and 0 in the lixisenatide one-step titration group. No death was reported in this study. More patients in lixisenatide-treated group (5 [4.2%] for two-step titration; 3 [2.5%] for one-step titration) discontinued treatment than in the placebo group (1 [0.8%]), mainly due to gastrointestinal disorders.

Table 25 presents the incidences of TEAEs during the double-blind treatment occurring in at least 1% of patients in any treatment group. Nausea was the most frequently reported TEAE in the lixisenatide-treated group: 29 patients (24.2%) for two-step titration and 24 patients (20.2%) for one-step titration. Five placebo-treated patients (4.1%) reported nausea. The second most frequently reported TEAE in the lixisenatide-treated patients was headache (10 patients (8.3%) for two-step titration and 9 patients (7.6%) for one-step titration) followed by vomiting (9 patients [7.5%] for two-step titration and 8 patients [6.7%] for one-step titration). The corresponding number of patients (%) in the placebo group was 14 (11.5%) for headache and none for vomiting.

TABLE 17

Overview of adverse event profile: treatment emergent adverse events - Safety population

|  | Placebo | | | Lixisenatide | | |
|---|---|---|---|---|---|---|
|  | Two-step Titration (N = 61) | One-step Titration (N = 61) | Combined (N = 122) | Two-step Titration (N = 120) | One-step Titration (N = 119) | Combined (N = 239) |
| Patients with any TEAE | 25 (41.0%) | 30 (49.2%) | 55 (45.1%) | 63 (52.5%) | 65 (54.6%) | 128 (53.6%) |
| Patients with any serious TEAE | 3 (4.9%) | 2 (3.3%) | 5 (4.1%) | 1 (0.8%) | 0 | 1 (0.4%) |
| Patients with any TEAE leading to death | 0 | 0 | 0 | 0 | 0 | 0 |
| Patients with any TEAE leading to permanent treatment discontinuation | 1 (1.6%) | 0 | 1 (0.8%) | 5 (4.2%) | 3 (2.5%) | 8 (3.3%) |

TEAE: Treatment Emergent Adverse Event.

n (%) = number and percentage of patients with at least one adverse event

TABLE 18

Number (%) of patients experiencing serious TEAE(s) presented by primary SOC, HLGT, HLT, and PT during on-treatment period - Safety population

| PRIMARY SYSTEM ORGAN CLASS HLGT: High Level Group Term HLT: High Level Term Preferred Term n (%) | Placebo | | | Lixisenatide | | |
|---|---|---|---|---|---|---|
|  | Two-step Titration (N = 61) | One-step Titration (N = 61) | Combined (N = 122) | Two-step Titration (N = 120) | One-step Titration (N = 119) | Combined (N = 239) |
| Any class | 3 (4.9%) | 2 (3.3%) | 5 (4.1%) | 1 (0.8%) | 0 | 1 (0.4%) |
| NEOPLASMS BENIGN, MALIGNANT AND UNSPECIFIED (INCL CYSTS AND POLYPS) | 1 (1.6%) | 0 | 1 (0.8%) | 0 | 0 | 0 |
| HLGT: Gastrointestinal neoplasms malignant and unspecified | 1 (1.6%) | 0 | 1 (0.8%) | 0 | 0 | 0 |
| HLT: Colonic neoplasms malignant | 1 (1.6%) | 0 | 1 (0.8%) | 0 | 0 | 0 |
| Colon cancer stage III | 1 (1.6%) | 0 | 1 (0.8%) | 0 | 0 | 0 |
| ENDOCRINE DISORDERS | 0 | 0 | 0 | 1 (0.8%) | 0 | 1 (0.4%) |
| HLGT: Thyroid gland disorders | 0 | 0 | 0 | 1 (0.8%) | 0 | 1 (0.4%) |
| HLT: Thyroid disorders NEC | 0 | 0 | 0 | 1 (0.8%) | 0 | 1 (0.4%) |
| Goitre | 0 | 0 | 0 | 1 (0.8%) | 0 | 1 (0.4%) |
| CARDIAC DISORDERS | 1 (1.6%) | 0 | 1 (0.8%) | 0 | 0 | 0 |
| HLGT: Coronary artery disorders | 1 (1.6%) | 0 | 1 (0.8%) | 0 | 0 | 0 |
| HLT: Ischaemic coronary artery disorders | 1 (1.6%) | 0 | 1 (0.8%) | 0 | 0 | 0 |
| Acute myocardial infarction | 1 (1.6%) | 0 | 1 (0.8%) | 0 | 0 | 0 |
| GASTROINTESTINAL DISORDERS | 1 (1.6%) | 0 | 1 (0.8%) | 0 | 0 | 0 |
| HLGT: Gastrointestinal stenosis and obstruction | 1 (1.6%) | 0 | 1 (0.8%) | 0 | 0 | 0 |
| HLT: Gastrointestinal stenosis and obstruction NEC | 1 (1.6%) | 0 | 1 (0.8%) | 0 | 0 | 0 |

TABLE 18-continued

Number (%) of patients experiencing serious TEAE(s) presented by primary SOC, HLGT, HLT, and PT during on-treatment period - Safety population

| PRIMARY SYSTEM ORGAN CLASS HLGT: High Level Group Term HLT: High Level Term Preferred Term n (%) | Placebo | | | Lixisenatide | | |
|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) |
| Ileus | 1 (1.6%) | 0 | 1 (0.8%) | 0 | 0 | 0 |
| INVESTIGATIONS | 0 | 1 (1.6%) | 1 (0.8%) | 0 | 0 | 0 |
| HLGT: Metabolic, nutritional and blood gas investigations | 0 | 1 (1.6%) | 1 (0.8%) | 0 | 0 | 0 |
| HLT: Carbohydrate tolerance analyses (incl diabetes) | 0 | 1 (1.6%) | 1 (0.8%) | 0 | 0 | 0 |
| Blood glucose increased | 0 | 1 (1.6%) | 1 (0.8%) | 0 | 0 | 0 |
| INJURY, POISONING AND PROCEDURAL COMPLICATIONS | 0 | 1 (1.6%) | 1 (0.8%) | 0 | 0 | 0 |
| HLGT: Bone and joint injuries | 0 | 1 (1.6%) | 1 (0.8%) | 0 | 0 | 0 |
| HLT: Upper limb fractures and dislocations | 0 | 1 (1.6%) | 1 (0.8%) | 0 | 0 | 0 |
| Ulna fracture | 0 | 1 (1.6%) | 1 (0.8%) | 0 | 0 | 0 |

TEAE: Treatment Emergent Adverse Event,
SOC: System Organ Class,
HLGT: High Level Group Term,
HLT: High Level term,
PT: Preferred Term.
On-treatment period = the time from the first dose of double-blind study medication up to 3 days after the last dose administration.
MedDRA version: 12.1
n (%) = number and percentage of patients with at least one serious TEAE.
Note:
Table sorted by SOC internationally agreed order and HLGT, HLT, PT alphabetic order.

TABLE 19

Number (%) of patients experiencing TEAE(s) leading to permanent treatment discontinuation by primary SOC, HLGT, HLT, and PT during on-treatment period - Safety population

| PRIMARY SYSTEM ORGAN CLASS HLGT: High Level Group Term HLT: High Level Term Preferred Term n (%) | Placebo | | | Lixisenatide | | |
|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) |
| Any class | 1 (1.6%) | 0 | 1 (0.8%) | 5 (4.2%) | 3 (2.5%) | 8 (3.3%) |
| NEOPLASMS BENIGN, MALIGNANT AND UNSPECIFIED (INCL CYSTS AND POLYPS) | 1 (1.6%) | 0 | 1 (0.8%) | 0 | 0 | 0 |
| HLGT: Gastrointestinal neoplasms malignant and unspecified | 1 (1.6%) | 0 | 1 (0.8%) | 0 | 0 | 0 |
| HLT: Colonic neoplasms malignant | 1 (1.6%) | 0 | 1 (0.8%) | 0 | 0 | 0 |
| Colon cancer stage III | 1 (1.6%) | 0 | 1 (0.8%) | 0 | 0 | 0 |

TABLE 19-continued

Number (%) of patients experiencing TEAE(s) leading to permanent
treatment discontinuation by primary SOC, HLGT, HLT, and PT
during on-treatment period - Safety population

| PRIMARY SYSTEM ORGAN CLASS HLGT: High Level Group | Placebo | | | Lixisenatide | | |
|---|---|---|---|---|---|---|
| Term HLT: High Level Term Preferred Term n (%) | Two-step Titration (N = 61) | One-step Titration (N = 61) | Combined (N = 122) | Two-step Titration (N = 120) | One-step Titration (N = 119) | Combined (N = 239) |
| METABOLISM AND NUTRITION DISORDERS | 0 | 0 | 0 | 1 (0.8%) | 0 | 1 (0.4%) |
| HLGT: Appetite and general nutritional disorders | 0 | 0 | 0 | 1 (0.8%) | 0 | 1 (0.4%) |
| HLT: Appetite disorders | 0 | 0 | 0 | 1 (0.8%) | 0 | 1 (0.4%) |
| Decreased appetite | 0 | 0 | 0 | 1 (0.8%) | 0 | 1 (0.4%) |
| VASCULAR DISORDERS | 0 | 0 | 0 | 0 | 1 (0.8%) | 1 (0.4%) |
| HLGT: Vascular hypertensive disorders | 0 | 0 | 0 | 0 | 1 (0.8%) | 1 (0.4%) |
| HLT: Vascular hypertensive disorders NEC | 0 | 0 | 0 | 0 | 1 (0.8%) | 1 (0.4%) |
| Hypertension | 0 | 0 | 0 | 0 | 1 (0.8%) | 1 (0.4%) |
| GASTROINTESTINAL DISORDERS | 0 | 0 | 0 | 5 (4.2%) | 3 (2.5%) | 8 (3.3%) |
| HLGT: Gastrointestinal haemorrhages NEC | 0 | 0 | 0 | 1 (0.8%) | 0 | 1 (0.4%) |
| HLT: Non-site specific gastrointestinal haemorrhages | 0 | 0 | 0 | 1 (0.8%) | 0 | 1 (0.4%) |
| Haematochezia | 0 | 0 | 0 | 1 (0.8%) | 0 | 1 (0.4%) |
| HLGT: Gastrointestinal inflammatory conditions | 0 | 0 | 0 | 1 (0.8%) | 0 | 1 (0.4%) |
| HLT: Colitis (excl infective) | 0 | 0 | 0 | 1 (0.8%) | 0 | 1 (0.4%) |
| Colitis | 0 | 0 | 0 | 1 (0.8%) | 0 | 1 (0.4%) |
| HLGT: Gastrointestinal signs and symptoms | 0 | 0 | 0 | 3 (2.5%) | 3 (2.5%) | 6 (2.5%) |
| HLT: Gastrointestinal and abdominal pains (excl oral and throat) | 0 | 0 | 0 | 0 | 1 (0.8%) | 1 (0.4%) |
| Abdominal pain upper | 0 | 0 | 0 | 0 | 1 (0.8%) | 1 (0.4%) |
| HLT: Nausea and vomiting symptoms | 0 | 0 | 0 | 3 (2.5%) | 3 (2.5%) | 6 (2.5%) |
| Nausea | 0 | 0 | 0 | 3 (2.5%) | 3 (2.5%) | 6 (2.5%) |
| Vomiting | 0 | 0 | 0 | 1 (0.8%) | 1 (0.8%) | 2 (0.8%) |

TEAE: Treatment Emergent Adverse Event,
SOC: System Organ Class,
HLGT: High Level Group Term,
HLT: High Level term,
PT: Preferred Term.
On-treatment period = the time from the first dose of double-blind study medication up to 3 days after the last dose administration.
MedDRA version: 12.1
n (%) = number and percentage of patients with at least one TEAE leading to permanent treatment discontinuation.
Note:
Table sorted by SOC internationally agreed order and HLGT, HLT, PT alphabetic order.

As shown in Table 20 below, a total of 6 cases of symptomatic hypoglycemia per protocol definition were observed (3 [2.5%] in the lixisenatide two-step titration group, 1 [0.8%] in the lixisenatide one-step titration group, and 2 [1.6%] in the placebo group), and none of them was severe.

TABLE 20

Summary of symptomatic hypoglycemia - Safety population

| Type | Placebo | | | Lixisenatide | | |
|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) |
| Exposure in patient years | 13.80 | 13.37 | 27.17 | 26.66 | 26.64 | 53.30 |
| Any symptomatic hypoglycemia | | | | | | |
| Number of patients with events, n (%)[1] | 1 (1.6%) | 1 (1.6%) | 2 (1.6%) | 3 (2.5%) | 1 (0.8%) | 4 (1.7%) |
| Number of patients with events per 100 patient years of exposure[2] | 7.2 | 7.5 | 7.4 | 11.3 | 3.8 | 7.5 |
| <60 mg/dL | | | | | | |
| Number of patients with events, n (%)[1] | 1 (1.6%) | 1 (1.6%) | 2 (1.6%) | 2 (1.7%) | 0 | 2 (0.8%) |
| Number of patients with events per 100 patient years of exposure[2] | 7.2 | 7.5 | 7.4 | 7.5 | 0 | 3.8 |
| No blood glucose reported | | | | | | |
| Number of patients with events, n (%)[1] | 0 | 0 | 0 | 1 (0.8%) | 1 (0.8%) | 2 (0.8%) |
| Number of patients with events per 100 patient years of exposure[2] | 0 | 0 | 0 | 3.8 | 3.8 | 3.8 |

Symptomatic hypoglycemia = symptomatic hypoglycemia as defined per protocol.
[1]Percents are calculated using the number of safety patients as the denominator.
[2]Number of patients with events per 100 patient years of exposure = 100 * (number of patients with events/exposure in patient years).

A total of 11 patients, all lixisenatide-treated patients (4 [3.3%] in two-step titration group and 7 [5.9%] in one-step titration group), reported injection site reactions. None of the reactions was serious or severe.

TABLE 21

Number (%) of patients experiencing injection site reactions during on-treatment period - Safety population

| Preferred Term n (%) | Placebo | | | Lixisenatide | | |
|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) |
| Any injection site reactions | 0 | 0 | 0 | 4 (3.3%) | 7 (5.9%) | 11 (4.6%) |
| Injection site pruritus | 0 | 0 | 0 | 2 (1.7%) | 4 (3.4%) | 6 (2.5%) |
| Injection site pain | 0 | 0 | 0 | 1 (0.8%) | 2 (1.7%) | 3 (1.3%) |
| Injection site haematoma | 0 | 0 | 0 | 1 (0.8%) | 1 (0.8%) | 2 (0.8%) |
| Injection site erythema | 0 | 0 | 0 | 0 | 2 (1.7%) | 2 (0.8%) |
| Injection site haemorrhage | 0 | 0 | 0 | 1 (0.8%) | 0 | 1 (0.4%) |
| Injection site rash | 0 | 0 | 0 | 1 (0.8%) | 0 | 1 (0.4%) |

On-treatment period = the time from the first dose of double-blind study medication up to 3 days after the last dose administration.

A total of 3 cases of allergic reactions were reported by investigators in the lixisenatide one-step titration group during double-blind treatment period and 2 of them were confirmed by the allergic reaction assessment committee (ARAC).

TABLE 22

Number (%) of patients with allergic reaction as adjudicated and confirmed by ARAC - Safety population

| Relationship to study treatment (by ARAC) | MedDRA coded term (PT) for ARAC diagnosis | ARAC diagnosis | Placebo | | | Lixisenatide | | |
|---|---|---|---|---|---|---|---|---|
| | | | Two-step Titration (N = 61) | One-step Titration (N = 61) | Combined (N = 122) | Two-step Titration (N = 120) | One-step Titration (N = 119) | Combined (N = 239) |
| All | Allergic reaction as adjudicated and confirmed by ARAC | | 0 | 0 | 0 | 0 | 2 (1.7%) | 2 (0.8%) |
| | Angioedema | ANGIOEDEMA | 0 | 0 | 0 | 0 | 1 (0.8%) | 1 (0.4%) |
| | Urticaria | URTICARIA (HIVES) | 0 | 0 | 0 | 0 | 1 (0.8%) | 1 (0.4%) |
| Related | Allergic reaction as adjudicated and confirmed by ARAC | | 0 | 0 | 0 | 0 | 2 (1.7%) | 2 (0.8%) |
| | Angioedema | ANGIOEDEMA | 0 | 0 | 0 | 0 | 1 (0.8%) | 1 (0.4%) |
| | Urticaria | URTICARIA (HIVES) | 0 | 0 | 0 | 0 | 1 (0.8%) | 1 (0.4%) |

ARAC = Allergic Reaction Assessment Committee.

The adverse event "lipase increased" reported in one patient in the placebo group Table 23 occurred on study Day 1 and presumably prior to the first injection of double-blind treatment according to the study protocol. No incidence of elevated lipase or amylase (≥3 ULN) was observed in any treatment group (Table 24) during the double-double treatment period.

TABLE 23

Number (%) of patients with suspected pancreatitis - Safety population

| | Placebo | | | Lixisenatide | | |
|---|---|---|---|---|---|---|
| Preferred Term | Two-step Titration (N = 61) | One-step Titration (N = 61) | Combined (N = 122) | Two-step Titration (N = 120) | One-step Titration (N = 119) | Combined (N = 239) |
| Any | 0 | 1 (1.6%) | 1 (0.8%) | 0 | 0 | 0 |
| Lipase increased | 0 | 1 (1.6%) | 1 (0.8%) | 0 | 0 | 0 | n (%) = number and percentage of patients with any cases reported on the AE form for suspected pancreatits along with complementary form.

TABLE 24

Pancreatic enzymes: Number of patients with abnormalities (PCSA) in the on-treatment period according to baseline status - Safety population

| Laboratory criteria | Placebo | | | Lixisenatide | | |
|---|---|---|---|---|---|---|
| Baseline by PCSA criteria n/N1 (%) | Two-step Titration (N = 61) | One-step Titration (N = 61) | Combined (N = 122) | Two-step Titration (N = 120) | One-step Titration (N = 119) | Combined (N = 239) |
| Amylase Total* | | | | | | |
| ≥3 ULN Normal/Missing | 0/61 | 0/59 | 0/120 | 0/119 | 0/118 | 0/237 |
| ≥3 ULN | 0/61 | 0/59 | 0/120 | 0/119 | 0/118 | 0/237 |

TABLE 24-continued

Pancreatic enzymes: Number of patients with abnormalities (PCSA) in the on-treatment period according to baseline status - Safety population

| Laboratory criteria | Placebo | | | Lixisenatide | | |
|---|---|---|---|---|---|---|
| Baseline by PCSA criteria n/N1 (%) | Two-step Titration (N = 61) | One-step Titration (N = 61) | Combined (N = 122) | Two-step Titration (N = 120) | One-step Titration (N = 119) | Combined (N = 239) |
| >=3 ULN | | | | | | |
| ≥3 ULN | 0/0 | 0/0 | 0/0 | 0/0 | 0/0 | 0/0 |
| Lipase Total* | | | | | | |
| ≥3 ULN Normal/Missing | 0/61 | 0/59 | 0/120 | 0/119 | 0/118 | 0/237 |
| ≥3 ULN >=3 ULN | 0/61 | 0/59 | 0/120 | 0/119 | 0/118 | 0/237 |
| ≥3 ULN | 0/0 | 0/0 | 0/0 | 0/0 | 0/0 | 0/0 |

PCSA: Potentially Clinically Significant Abnormalities.
On-treatment period = the time from the first dose of double-blind study medication up to 3 days after the last dose administration.
*Regardless of baseline.
Note:
The number (n) represents the subset of the total number who met the criterion in question at least once during treatment.
The denominator (/N1) for each parameter within a treatment group is the number of patients for the treatment group who had that parameter assessed post-baseline by baseline PCSA status.
For PCSA including condition based only on change from baseline, the denominator is restricted on patients having a baseline and a post-baseline values.

TABLE 25

Number (%) of patients experiencing common TEAE(s) (PT ≥1% in the placebo combined group or any individual lixisenatide group) by primary SOC and HLGT, HLT and PT - Safety population

| Primary System Organ Class HLGT: High Level Group Term HLT: High Level Term Preferred Term n (%) | Placebo | | | Lixisenatide | | |
|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) |
| Any class | 25 (41.0%) | 30 (49.2%) | 55 (45.1%) | 63 (52.5%) | 65 (54.6%) | 128 (53.6%) |
| INFECTIONS AND INFESTATIONS | 7 (11.5%) | 10 (16.4%) | 17 (13.9%) | 17 (14.2%) | 15 (12.6%) | 32 (13.4%) |
| HLGT: Infections - pathogen unspecified | 7 (11.5%) | 8 (13.1%) | 15 (12.3%) | 16 (13.3%) | 14 (11.8%) | 30 (12.6%) |
| HLT: Abdominal and gastrointestinal infections | 1 (1.6%) | 2 (3.3%) | 3 (2.5%) | 1 (0.8%) | 0 | 1 (0.4%) |
| Gastroenteritis | 1 (1.6%) | 2 (3.3%) | 3 (2.5%) | 1 (0.8%) | 0 | 1 (0.4%) |
| HLT: Upper respiratory tract infections | 5 (8.2%) | 3 (4.9%) | 8 (6.6%) | 12 (10.0%) | 12 (10.1%) | 24 (10.0%) |
| Nasopharyngitis | 3 (4.9%) | 1 (1.6%) | 4 (3.3%) | 6 (5.0%) | 5 (4.2%) | 11 (4.6%) |
| Pharyngitis | 2 (3.3%) | 1 (1.6%) | 3 (2.5%) | 2 (1.7%) | 0 | 2 (0.8%) |
| Upper respiratory tract infection | 0 | 0 | 0 | 2 (1.7%) | 4 (3.4%) | 6 (2.5%) |
| HLT: Urinary tract infections | 0 | 2 (3.3%) | 2 (1.6%) | 2 (1.7%) | 0 | 2 (0.8%) |
| Urinary tract infection | 0 | 2 (3.3%) | 2 (1.6%) | 2 (1.7%) | 0 | 2 (0.8%) |
| METABOLISM AND NUTRITION DISORDERS | 1 (1.6%) | 1 (1.6%) | 2 (1.6%) | 6 (5.0%) | 6 (5.0%) | 12 (5.0%) |

TABLE 25-continued

Number (%) of patients experiencing common TEAE(s) (PT ≥1% in the placebo combined group or any individual lixisenatide group) by primary SOC and HLGT, HLT and PT - Safety population

| Primary System Organ Class HLGT: High Level Group Term | Placebo | | | Lixisenatide | | |
|---|---|---|---|---|---|---|
| HLT: High Level Term Preferred Term n (%) | Two-step Titration (N = 61) | One-step Titration (N = 61) | Combined (N = 122) | Two-step Titration (N = 120) | One-step Titration (N = 119) | Combined (N = 239) |
| HLGT: Appetite and general nutritional disorders | 1 (1.6%) | 0 | 1 (0.8%) | 3 (2.5%) | 5 (4.2%) | 8 (3.3%) |
| HLT: Appetite disorders | 1 (1.6%) | 0 | 1 (0.8%) | 3 (2.5%) | 5 (4.2%) | 8 (3.3%) |
| Decreased appetite | 1 (1.6%) | 0 | 1 (0.8%) | 3 (2.5%) | 5 (4.2%) | 8 (3.3%) |
| HLGT: Glucose metabolism disorders (incl diabetes mellitus) | 1 (1.6%) | 1 (1.6%) | 2 (1.6%) | 4 (3.3%) | 1 (0.8%) | 5 (2.1%) |
| HLT: Hypoglycaemic conditions NEC | 1 (1.6%) | 1 (1.6%) | 2 (1.6%) | 4 (3.3%) | 1 (0.8%) | 5 (2.1%) |
| Hypoglycaemia | 1 (1.6%) | 1 (1.6%) | 2 (1.6%) | 4 (3.3%) | 1 (0.8%) | 5 (2.1%) |
| NERVOUS SYSTEM DISORDERS | 9 (14.8%) | 8 (13.1%) | 17 (13.9%) | 22 (18.3%) | 15 (12.6%) | 37 (15.5%) |
| HLGT: Headaches | 9 (14.8%) | 5 (8.2%) | 14 (11.5%) | 10 (8.3%) | 9 (7.6%) | 19 (7.9%) |
| HLT: Headaches NEC | 9 (14.8%) | 5 (8.2%) | 14 (11.5%) | 10 (8.3%) | 9 (7.6%) | 19 (7.9%) |
| Headache | 9 (14.8%) | 5 (8.2%) | 14 (11.5%) | 10 (8.3%) | 9 (7.6%) | 19 (7.9%) |
| HLGT: Neurological disorders NEC | 1 (1.6%) | 3 (4.9%) | 4 (3.3%) | 12 (10.0%) | 6 (5.0%) | 18 (7.5%) |
| HLT: Disturbances in consciousness NEC | 0 | 0 | 0 | 2 (1.7%) | 1 (0.8%) | 3 (1.3%) |
| Somnolence | 0 | 0 | 0 | 2 (1.7%) | 1 (0.8%) | 3 (1.3%) |
| HLT: Neurological signs and symptoms NEC | 1 (1.6%) | 2 (3.3%) | 3 (2.5%) | 9 (7.5%) | 4 (3.4%) | 13 (5.4%) |
| Dizziness | 1 (1.6%) | 2 (3.3%) | 3 (2.5%) | 9 (7.5%) | 4 (3.4%) | 13 (5.4%) |
| CARDIAC DISORDERS | 1 (1.6%) | 1 (1.6%) | 2 (1.6%) | 2 (1.7%) | 5 (4.2%) | 7 (2.9%) |
| HLGT: Cardiac disorder signs and symptoms | 0 | 0 | 0 | 1 (0.8%) | 3 (2.5%) | 4 (1.7%) |
| HLT: Cardiac signs and symptoms NEC | 0 | 0 | 0 | 1 (0.8%) | 3 (2.5%) | 4 (1.7%) |
| Palpitations | 0 | 0 | 0 | 1 (0.8%) | 3 (2.5%) | 4 (1.7%) |
| RESPIRATORY, THORACIC AND MEDIASTINAL DISORDERS | 1 (1.6%) | 4 (6.6%) | 5 (4.1%) | 3 (2.5%) | 5 (4.2%) | 8 (3.3%) |
| HLGT: Respiratory disorders NEC | 1 (1.6%) | 3 (4.9%) | 4 (3.3%) | 3 (2.5%) | 5 (4.2%) | 8 (3.3%) |
| HLT: Coughing and associated symptoms | 1 (1.6%) | 1 (1.6%) | 2 (1.6%) | 1 (0.8%) | 2 (1.7%) | 3 (1.3%) |
| Cough | 1 (1.6%) | 1 (1.6%) | 2 (1.6%) | 1 (0.8%) | 2 (1.7%) | 3 (1.3%) |
| HLT: Upper respiratory tract signs and symptoms | 0 | 3 (4.9%) | 3 (2.5%) | 2 (1.7%) | 3 (2.5%) | 5 (2.1%) |
| Oropharyngeal pain | 0 | 3 (4.9%) | 3 (2.5%) | 1 (0.8%) | 2 (1.7%) | 3 (1.3%) |
| GASTROINTESTINAL DISORDERS | 7 (11.5%) | 10 (16.4%) | 17 (13.9%) | 39 (32.5%) | 37 (31.1%) | 76 (31.8%) |
| HLGT: Dental and gingival conditions | 1 (1.6%) | 2 (3.3%) | 3 (2.5%) | 1 (0.8%) | 1 (0.8%) | 2 (0.8%) |
| HLT: Dental pain and sensation disorders | 1 (1.6%) | 1 (1.6%) | 2 (1.6%) | 1 (0.8%) | 1 (0.8%) | 2 (0.8%) |

TABLE 25-continued

Number (%) of patients experiencing common TEAE(s) (PT ≥1% in the placebo combined group or any individual lixisenatide group) by primary SOC and HLGT, HLT and PT - Safety population

| Primary System Organ Class HLGT: High Level Group Term HLT: High Level Term Preferred Term n (%) | Placebo | | | Lixisenatide | | |
|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) |
| Toothache | 1 (1.6%) | 1 (1.6%) | 2 (1.6%) | 1 (0.8%) | 1 (0.8%) | 2 (0.8%) |
| HLGT: Gastrointestinal motility and defaecation conditions | 2 (3.3%) | 2 (3.3%) | 4 (3.3%) | 7 (5.8%) | 6 (5.0%) | 13 (5.4%) |
| HLT: Diarrhoea (excl infective) | 1 (1.6%) | 2 (3.3%) | 3 (2.5%) | 3 (2.5%) | 4 (3.4%) | 7 (2.9%) |
| Diarrhoea | 1 (1.6%) | 2 (3.3%) | 3 (2.5%) | 3 (2.5%) | 4 (3.4%) | 7 (2.9%) |
| HLT: Gastrointestinal atonic and hypomotility disorders NEC | 1 (1.6%) | 0 | 1 (0.8%) | 4 (3.3%) | 2 (1.7%) | 6 (2.5%) |
| Constipation | 1 (1.6%) | 0 | 1 (0.8%) | 4 (3.3%) | 2 (1.7%) | 6 (2.5%) |
| HLGT: Gastrointestinal signs and symptoms | 4 (6.6%) | 4 (6.6%) | 8 (6.6%) | 33 (27.5%) | 29 (24.4%) | 62 (25.9%) |
| HLT: Dyspeptic signs and symptoms | 1 (1.6%) | 0 | 1 (0.8%) | 2 (1.7%) | 2 (1.7%) | 4 (1.7%) |
| Dyspepsia | 1 (1.6%) | 0 | 1 (0.8%) | 2 (1.7%) | 2 (1.7%) | 4 (1.7%) |
| Eructation | 0 | 0 | 0 | 0 | 2 (1.7%) | 2 (0.8%) |
| HLT: Flatulence, bloating and distension | 0 | 0 | 0 | 2 (1.7%) | 3 (2.5%) | 5 (2.1%) |
| Abdominal distension | 0 | 0 | 0 | 1 (0.8%) | 3 (2.5%) | 4 (1.7%) |
| HLT: Gastrointestinal and abdominal pains (excl oral and throat) | 0 | 2 (3.3%) | 2 (1.6%) | 5 (4.2%) | 2 (1.7%) | 7 (2.9%) |
| Abdominal pain | 0 | 2 (3.3%) | 2 (1.6%) | 2 (1.7%) | 0 | 2 (0.8%) |
| Abdominal pain upper | 0 | 0 | 0 | 4 (3.3%) | 2 (1.7%) | 6 (2.5%) |
| HLT: Gastrointestinal signs and symptoms NEC | 0 | 0 | 0 | 0 | 2 (1.7%) | 2 (0.8%) |
| Abdominal discomfort | 0 | 0 | 0 | 0 | 2 (1.7%) | 2 (0.8%) |
| HLT: Nausea and vomiting symptoms | 3 (4.9%) | 2 (3.3%) | 5 (4.1%) | 29 (24.2%) | 25 (21.0%) | 54 (22.6%) |
| Nausea | 3 (4.9%) | 2 (3.3%) | 5 (4.1%) | 29 (24.2%) | 24 (20.2%) | 53 (22.2%) |
| Vomiting | 0 | 0 | 0 | 9 (7.5%) | 8 (6.7%) | 17 (7.1%) |
| SKIN AND SUBCUTANEOUS TISSUE DISORDERS | 1 (1.6%) | 0 | 1 (0.8%) | 3 (2.5%) | 5 (4.2%) | 8 (3.3%) |
| HLGT: Epidermal and dermal conditions | 0 | 0 | 0 | 1 (0.8%) | 4 (3.4%) | 5 (2.1%) |
| HLT: Rashes, eruptions and exanthems NEC | 0 | 0 | 0 | 0 | 2 (1.7%) | 2 (0.8%) |
| Rash | 0 | 0 | 0 | 0 | 2 (1.7%) | 2 (0.8%) |

TABLE 25-continued

Number (%) of patients experiencing common TEAE(s) (PT ≥1% in the placebo combined group or any individual lixisenatide group) by primary SOC and HLGT, HLT and PT - Safety population

| Primary System Organ Class HLGT: High Level Group Term HLT: High Level Term Preferred Term n (%) | Placebo | | | Lixisenatide | | |
|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) |
| HLGT: Skin appendage conditions | 1 (1.6%) | 0 | 1 (0.8%) | 2 (1.7%) | 0 | 2 (0.8%) |
| HLT: Apocrine and eccrine gland disorders | 1 (1.6%) | 0 | 1 (0.8%) | 2 (1.7%) | 0 | 2 (0.8%) |
| Hyperhidrosis | 1 (1.6%) | 0 | 1 (0.8%) | 2 (1.7%) | 0 | 2 (0.8%) |
| MUSCULOSKELETAL AND CONNECTIVE TISSUE DISORDERS | 1 (1.6%) | 5 (8.2%) | 6 (4.9%) | 8 (6.7%) | 4 (3.4%) | 12 (5.0%) |
| HLGT: Muscle disorders | 0 | 0 | 0 | 3 (2.5%) | 1 (0.8%) | 4 (1.7%) |
| HLT: Muscle related signs and symptoms NEC | 0 | 0 | 0 | 2 (1.7%) | 0 | 2 (0.8%) |
| Muscle spasms | 0 | 0 | 0 | 2 (1.7%) | 0 | 2 (0.8%) |
| HLGT: Musculoskeletal and connective tissue disorders NEC | 1 (1.6%) | 5 (8.2%) | 6 (4.9%) | 4 (3.3%) | 2 (1.7%) | 6 (2.5%) |
| HLT: Musculoskeletal and connective tissue pain and discomfort | 1 (1.6%) | 5 (8.2%) | 6 (4.9%) | 4 (3.3%) | 2 (1.7%) | 6 (2.5%) |
| Back pain | 0 | 2 (3.3%) | 2 (1.6%) | 4 (3.3%) | 1 (0.8%) | 5 (2.1%) |
| Musculoskeletal chest pain | 0 | 2 (3.3%) | 2 (1.6%) | 0 | 0 | 0 |
| GENERAL DISORDERS AND ADMINISTRATION SITE CONDITIONS | 1 (1.6%) | 1 (1.6%) | 2 (1.6%) | 9 (7.5%) | 11 (9.2%) | 20 (8.4%) |
| HLGT: Administration site reactions | 0 | 0 | 0 | 4 (3.3%) | 7 (5.9%) | 11 (4.6%) |
| HLT: Injection site reactions | 0 | 0 | 0 | 4 (3.3%) | 7 (5.9%) | 11 (4.6%) |
| Injection site erythema | 0 | 0 | 0 | 0 | 2 (1.7%) | 2 (0.8%) |
| Injection site pain | 0 | 0 | 0 | 1 (0.8%) | 2 (1.7%) | 3 (1.3%) |
| Injection site pruritus | 0 | 0 | 0 | 2 (1.7%) | 4 (3.4%) | 6 (2.5%) |
| HLGT: General system disorders NEC | 1 (1.6%) | 1 (1.6%) | 2 (1.6%) | 5 (4.2%) | 6 (5.0%) | 11 (4.6%) |
| HLT: Asthenic conditions | 1 (1.6%) | 1 (1.6%) | 2 (1.6%) | 5 (4.2%) | 5 (4.2%) | 10 (4.2%) |
| Asthenia | 0 | 1 (1.6%) | 1 (0.8%) | 1 (0.8%) | 3 (2.5%) | 4 (1.7%) |
| Fatigue | 1 (1.6%) | 0 | 1 (0.8%) | 4 (3.3%) | 1 (0.8%) | 5 (2.1%) |
| HLT: Feelings and sensations NEC | 0 | 0 | 0 | 0 | 2 (1.7%) | 2 (0.8%) |
| Chills | 0 | 0 | 0 | 0 | 2 (1.7%) | 2 (0.8%) |
| INJURY, POISONING AND PROCEDURAL COMPLICATIONS | 2 (3.3%) | 2 (3.3%) | 4 (3.3%) | 3 (2.5%) | 2 (1.7%) | 5 (2.1%) |

TABLE 25-continued

Number (%) of patients experiencing common TEAE(s) (PT ≥1% in the placebo combined group or any individual lixisenatide group) by primary SOC and HLGT, HLT and PT - Safety population

| Primary System Organ Class HLGT: High Level Group Term HLT: High Level Term Preferred Term n (%) | Placebo | | | Lixisenatide | | |
|---|---|---|---|---|---|---|
| | Two-step Titration (N = 61) | One-step Titration (N = 61) | Combined (N = 122) | Two-step Titration (N = 120) | One-step Titration (N = 119) | Combined (N = 239) |
| HLGT: Injuries NEC | 2 (3.3%) | 2 (3.3%) | 4 (3.3%) | 1 (0.8%) | 1 (0.8%) | 2 (0.8%) |
| HLT: Non-site specific injuries NEC | 1 (1.6%) | 2 (3.3%) | 3 (2.5%) | 0 | 1 (0.8%) | 1 (0.4%) |
| Fall | 1 (1.6%) | 2 (3.3%) | 3 (2.5%) | 0 | 0 | 0 |

TEAE: Treatment emergent adverse event,
SOC: System organ class,
HLGT: High level group term,
HLT: High level term,
PT: Preferred term
On-treatment period = the time from the first dose of double-blind study medication up to 3 days after the last dose administration.
MedDRA version: 12.1
n (%) = number and percentage of patients with at least one TEAE.
Note:
Table sorted by SOC internationally agreed order and HLGT, HLT, PT by alphabetic order.
Only SOC with at least one PT ≥1% in the placebo combined group or any lixisenatide one-or two-step titration group are presented.

---

The invention claimed is:

1. A method of improving glycemic control in a patient with type 2 diabetes mellitus comprising:
   administering a dose of 10 μg lixisenatide to the patient once daily for 14 days, and
   administering a dose of 20 μg lixisenatide to the patient once daily starting on day 15 of lixisenatide treatment.

2. The method of claim 1, wherein the patient is an adult.

3. The method of claim 1, wherein the patient has an HbA1c value of about 7% to about 10%.

4. The method of claim 1, wherein the patient is not currently receiving treatment with antidiabetic agents.

5. The method of claim 1, wherein the patient is inadequately controlled on the patient's current antidiabetic treatment.

6. The method of claim 5, wherein the patient's current antidiabetic treatment does not include an antidiabetic agent.

7. The method of claim 1, wherein the lixisenatide is administered as a pharmaceutical composition comprising lixisenatide, methionine, a suitable preservative, and a tonicity agent.

8. The method of claim 1, wherein the lixisenatide is administered as a pharmaceutical composition comprising lixisenatide, methionine, m-cresol, and glycerol.

* * * * *

SEQUENCE LISTING

<160> NUMBER OF SEQ ID NOS: 2

<210> SEQ ID NO 1
<211> LENGTH: 44
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (44)..(44)
<223> OTHER INFORMATION: Lys is C-terminally amidated

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 2
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (39)..(39)
<223> OTHER INFORMATION: Ser is C-terminally amidated

<400> SEQUENCE: 2

His Gly Glu Gly Thr Phe Thr Ser Asp Leu Ser Lys Gln Met Glu Glu

```
                1               5                    10                   15
Glu Ala Val Arg Leu Phe Ile Glu Trp Leu Lys Asn Gly Gly Pro Ser
                20                   25                   30
Ser Gly Ala Pro Pro Ser
            35
```